(12) United States Patent
Hwang et al.

(10) Patent No.: US 8,394,511 B2
(45) Date of Patent: Mar. 12, 2013

(54) COMPOUND FOR FORMING ORGANIC FILM, AND ORGANIC LIGHT EMITTING DEVICE AND FLAT PANEL DISPLAY DEVICE INCLUDING THE SAME

(75) Inventors: Seok-Hwan Hwang, Suwon-si (KR);
Young-Kook Kim, Suwon-si (KR);
Yoon-Hyun Kwak, Suwon-si (KR);
Jeoung-In Yi, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 401 days.

(21) Appl. No.: 12/336,459

(22) Filed: Dec. 16, 2008

(65) Prior Publication Data

US 2009/0200928 A1 Aug. 13, 2009

(30) Foreign Application Priority Data

Feb. 11, 2008 (KR) ........................ 10-2008-0012206

(51) Int. Cl.
*H01L 51/54* (2006.01)
*C09K 11/06* (2006.01)

(52) U.S. Cl. ........ 428/690; 428/917; 313/502; 313/504; 548/442; 564/427

(58) Field of Classification Search ........................ None
See application file for complete search history.

(56) References Cited

U.S. PATENT DOCUMENTS

| | | | |
|---|---|---|---|
| 4,356,429 A | 10/1982 | Tang | |
| 5,550,066 A | 8/1996 | Tang et al. | |
| 6,008,588 A | 12/1999 | Fujii | |
| 6,124,024 A | 9/2000 | Hosokawa et al. | |
| 6,465,115 B2 | 10/2002 | Shi et al. | |
| 6,485,847 B1 * | 11/2002 | Uchida et al. | 428/690 |
| 6,517,957 B1 * | 2/2003 | Senoo et al. | 428/690 |
| 6,596,415 B2 | 7/2003 | Shi et al. | |
| 7,431,997 B2 | 10/2008 | Hwang et al. | |
| 7,737,627 B2 * | 6/2010 | Hwang et al. | 313/504 |
| 2001/0010374 A1 | 8/2001 | Takayama | |
| 2003/0157364 A1 | 8/2003 | Senoo et al. | |
| 2003/0224207 A1 | 12/2003 | Song et al. | |
| 2004/0140757 A1 | 7/2004 | Tyan et al. | |
| 2005/0062406 A1 | 3/2005 | Kinoshita | |
| 2005/0067951 A1 | 3/2005 | Richter et al. | |
| 2005/0162074 A1 | 7/2005 | Madathil et al. | |
| 2005/0221124 A1 | 10/2005 | Hwang et al. | |
| 2006/0017377 A1 | 1/2006 | Ryu | |
| 2006/0020136 A1 | 1/2006 | Hwang et al. | |
| 2006/0115680 A1 * | 6/2006 | Hwang et al. | 428/690 |
| 2006/0251924 A1 | 11/2006 | Lu et al. | |
| 2007/0134512 A1 | 6/2007 | Klubek et al. | |
| 2007/0231503 A1 * | 10/2007 | Hwang et al. | 428/1.1 |
| 2008/0107919 A1 | 5/2008 | Hwang et al. | |
| 2008/0124572 A1 | 5/2008 | Mizuki et al. | |
| 2009/0167161 A1 | 7/2009 | Yabunouchi et al. | |

FOREIGN PATENT DOCUMENTS

| | | |
|---|---|---|
| CN | 1702065 A | 11/2005 |
| CN | 1978441 A | 6/2007 |
| DE | 102 03 328 A1 | 8/2003 |
| EP | 1 661 888 A1 | 5/2006 |
| EP | 1 862 524 A1 | 12/2007 |
| EP | 0 879 868 A2 | 11/2008 |
| JP | 09268284 A * | 10/1997 |
| JP | 11-035532 | 2/1999 |
| JP | 11-144875 | 5/1999 |
| JP | 11-329734 | 11/1999 |
| JP | 2000-302756 | 10/2000 |
| JP | 2002-252089 | 9/2002 |
| JP | 2003-073343 | 3/2003 |
| JP | 2004-087393 | 3/2004 |
| JP | 2004-087395 | 3/2004 |
| JP | 2004-103467 | 4/2004 |
| JP | 2004-345960 | 12/2004 |
| JP | 2005-029000 | 10/2005 |
| JP | 2005-289914 | 10/2005 |
| JP | 2005-294504 | 10/2005 |
| JP | 2006-028176 | 2/2006 |
| JP | 2006-041471 | 2/2006 |
| JP | 2006-151979 | 6/2006 |
| JP | 2007-036188 | 2/2007 |
| JP | 2007-055996 | 3/2007 |
| JP | 2007-126439 | 5/2007 |

(Continued)

OTHER PUBLICATIONS

Machine translation of JP09-268284. Date of publication: Oct. 14, 1997.*
English translation of JP09-268284. Date of publication: Oct. 14, 1997.*
KIPO Office action dated Oct. 27, 2009, for priority Korean application 10-2008-0012206.
KIPO Registration Determination Certificate dated May 31, 2010, for priority Korean Patent application 10-2008-0012206, as well as KR 10-2006-0059613 and JP 2004-087395.
European Search Report dated May 8, 2009, for corresponding European Application 09250339.0.

(Continued)

*Primary Examiner* — Lynda Salvatore
*Assistant Examiner* — Andrew K Bohaty
(74) *Attorney, Agent, or Firm* — Christie, Parker & Hale, LLP

(57) ABSTRACT

A compound for use in an organic light emitting device is represented by

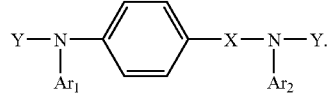

Formula 1

The compound has excellent electrical properties and charge transporting characteristics, and is therefore useful as a material for a hole injection layer, a hole transport layer, and an emission layer of phosphorescent and fluorescent devices for emitting light of all colors, including red, green, blue, and white. Organic light emitting devices using the compounds have high efficiency, low driving voltages, and high brightness.

19 Claims, 2 Drawing Sheets

FOREIGN PATENT DOCUMENTS

| | | |
|---|---|---|
| JP | 2007-318101 | 12/2007 |
| KR | 10-2005-0078472 A | 8/2005 |
| KR | 10-2006-0059613 | 6/2006 |
| WO | WO 03/008515 A1 | 1/2003 |
| WO | WO 2006/033492 A1 | 3/2006 |
| WO | WO 2007/007885 | 1/2007 |
| WO | WO 2007/043484 | 4/2007 |
| WO | WO 2008/010377 A1 | 1/2008 |
| WO | WO 2008/062636 | 5/2008 |
| WO | WO 2009/084268 | 7/2009 |

OTHER PUBLICATIONS

Korean Patent Abstracts, Publication No. 10-2005-0078472, dated Aug. 5, 2005, in the name of Seok Jong Lee et al.

Kuwabara, Y., et al., *Thermally Stable Multilayered Organic Electroluminescent Devices Using Novel Starburst Molecules, 4,4',4"-Tri(N-carbazoly)triphenylamine (TCTA) and 4,4',4"—Tris (3-methylphenylphenyl-amino)triphenylamine (m-MTDATA), as Hole-Transport Materials*, Advanced Materials, vol. 6, No. 9, (1994), pp. 677-679.

Adachi, C., et al., *Endothermic energy transfer: A mechanism for generating very efficient high-energy phosphorescent emisssion in organic materials*, Applied Physics Letters, vol. 79, No. 13, Sep. 24, 2001, pp. 2082-2084.

SIPO Office action dated Nov. 24, 2011, for corresponding Chinese Patent application 200910005168.0, 7 pages.

Japanese Office action dated Nov. 29, 2011, for corresponding Japanese Patent application 2009-027510, 2 pages.

European Search Report dated Sep. 25, 2009, for European Patent application 09251918.0, 5 pages.

U.S. Office action dated Sep. 23, 2011, for cross reference U.S. Appl. No. 12/511,412, 10 pages.

European Office action dated Aug. 2, 2012, for corresponding European Patent application 09250339.0, (4 pages).

European Search Report dated Jul. 24, 2007, for European Application 07109066.6.

European Search Report dated Nov. 7, 2007, for European Application 07109066.6.

KIPO Registration Determination Certificate dated May 28, 2008, for Korean Patent application 10-2007-0047850.

KIPO Office action dated Nov. 27, 2007, for Korean application 2006-0048306.

Japanese Office action dated Jun. 1, 2010, for Japanese Patent application 2007-110746.

U.S. Office action dated Jul. 8, 2008, for cross reference U.S. Appl. No. 11/097,182, (now U.S. Patent 7,737,627), 3 pages.

U.S. Office action dated Jan. 15, 2008, for cross reference U.S. Appl. No. 11/097,182, (now U.S. Patent 7,737,627), 7 pages.

U.S. Office action dated Apr. 1, 2011, for cross reference U.S. Appl. No. 12/122,143, 14 pages.

U.S. Office action dated Feb. 8, 2010, for cross reference U.S. Appl. No. 11/806,039, 27 pages.

U.S. Office action dated May 10, 2011, for cross reference U.S. Appl. No. 11/806,039, 32 pages.

Shen, et al., *High $T_g$ blue emitting materials for electroluminescent devices*, Journal of Materials Chemistry, (2005), Issue 15, pp. 2455-2463.

Thomas, K., et al., *Light-Emitting Carbazole Derivatives: Potential Electroluminescent Materials*, Journal of American Chemical Society, (2001), vol. 123, No. 23, pp. 9404-9411.

Thomas, K., et al., *Green and Yellow Electroluminescent Dipolar Carbazole Derivatives: Features and Benefits of Electron-Withdrawing Segments*, Chemistry of Materials, (2002), vol. 14, No. 9, pp. 3852-3859.

Derwent English machine translation of German Publication 102 03 328, 7 pages, Aug. 7, 2003.

English machine translation of Japanese Publication 11-144875, 25 pages, May 29, 1999.

SIPO Office action dated Dec. 26, 2008, for Chinese Patent application 200510069765.1, with English translation.

\* cited by examiner

COMPOUND FOR FORMING ORGANIC FILM, AND ORGANIC LIGHT EMITTING DEVICE AND FLAT PANEL DISPLAY DEVICE INCLUDING THE SAME

CROSS-REFERENCE TO RELATED PATENT APPLICATION

This application claims priority to and the benefit of Korean Patent Application No. 10-2008-0012206, filed on Feb. 11, 2008 in the Korean Intellectual Property Office, the entire content of which is incorporated herein by reference.

BACKGROUND OF THE INVENTION

1. Field of the Invention

The present invention relates to compounds for forming organic films, to organic light emitting devices including the organic films, and to flat panel display devices including the organic light emitting devices.

2. Description of the Related Art

Organic light emitting diodes are self light emitting devices which have wide viewing angles, excellent contrast, and quick response times. As such, organic light emitting diodes are receiving a lot of attention. Moreover, organic light emitting diodes have excellent driving voltage characteristics and response speeds, and can emit light of many colors.

A conventional organic light emitting diode has an anode/emissive layer/cathode structure. The organic light emitting diode may further include at least one of a hole injection layer, a hole transport layer, and an electron injection layer between the anode and the emissive layer, or between the emissive layer and the cathode, to form an anode/hole transport layer/emissive layer/cathode structure, or an anode/hole transport layer/emissive layer/cathode structure.

As materials for forming the hole transport layer, polyphenyl compounds or anthracene derivatives have been used. However, organic light emitting devices including hole injection layers and/or hole transport layers formed of these conventional materials do not have satisfactory life spans, efficiency, and power consumption.

SUMMARY OF THE INVENTION

In one embodiment of the present invention, a compound for forming an organic film has high electrical stability, good charge transporting characteristics, and a high glass transition temperature, thereby preventing crystallization. The compound is suitable for use in phosphorescent and fluorescent organic light emitting devices for emitting light of all colors including red, green, blue, and white.

According to another embodiment of the present invention, an organic light emitting device includes the organic film, has high efficiency, low voltage, and high brightness.

In yet another embodiment of the present invention, a flat-panel display device includes the organic light-emitting device.

According to one embodiment of the present invention, a compound is represented by Formula 1 below.

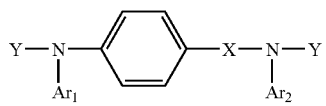

Formula 1

In Formula 1, X is selected from substituted and unsubstituted $C_6$-$C_{20}$ aryl groups, and substituted and unsubstituted $C_4$-$C_{20}$ condensed polycyclic groups. Each of $Ar_1$ and $Ar_2$ is independently selected from substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups. Y is selected from substituents represented by Formulae 2 and 3 below.

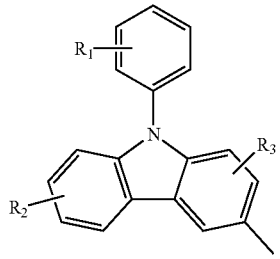

Formula 2

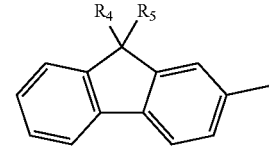

Formula 3

In Formulae 2 and 3, each of $R_1$, $R_2$, $R_3$, $R_4$ and $R_5$ is independently selected from hydrogen, substituted or unsubstituted $C_1$-$C_{10}$ alkyl groups, a substituted or nonsubstituted $C_6$-$C_{20}$ aryl group, substituted or unsubstituted $C_1$-$C_{10}$ alkoxy groups, fluorine, cyano groups, and amine groups. In some embodiments, adjacent R groups among $R_1$, $R_2$, $R_3$, $R_4$ and $R_5$ may bond with one another to form a saturated or unsaturated carbon ring.

According to another embodiment of the present invention, an organic light-emitting device includes a first electrode, a second electrode, and an organic film between the first and second electrodes, the organic film including the compound of Formula 1.

In one embodiment, the organic film may be a hole injection layer, a hole transport layer, or an emissive layer.

The organic light emitting device including the organic film including the compound of Formula 1 may have a low driving voltage, high brightness, high efficiency, high current density and the like.

According to another embodiment of the present invention, a flat-panel display device includes the organic light emitting device, and the first electrode of the organic light emitting device is electrically connected to a source electrode or a drain electrode of a thin film transistor.

BRIEF DESCRIPTION OF THE DRAWINGS

The above and other features and advantages of the present invention will become more apparent by reference to the following detailed description when considered in conjunction with the attached drawings in which.

DETAILED DESCRIPTION OF THE INVENTION

Figure 1:
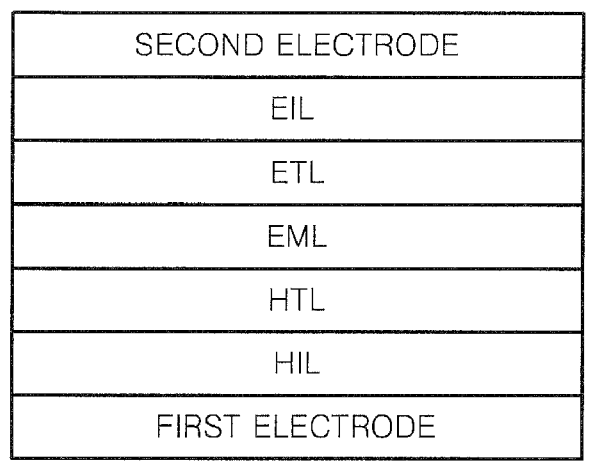
FIG. 1 is a diagram of a structure of an organic light emitting device according to an embodiment of the present invention.

According to an embodiment of the present invention, a compound is represented by Formula 1 below.

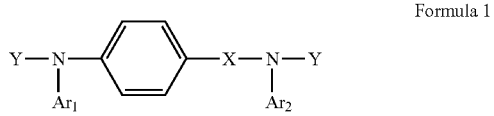

Formula 1

In Formula 1, X is selected from substituted and unsubstituted $C_6$-$C_{20}$ aryl groups, and substituted and unsubstituted $C_4$-$C_{20}$ condensed polycyclic groups. Each of $Ar_1$ and $Ar_2$ is independently selected from substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups. Y is selected from substituents represented by the below structures.

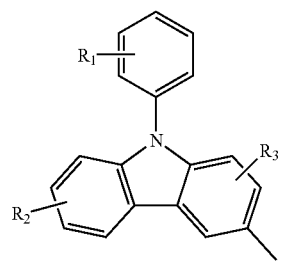

Formula 2

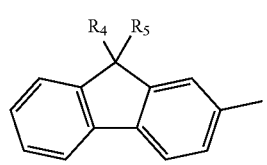

Formula 3

In Formula 2 and 3, each of $R_1$, $R_2$, $R_3$, $R_4$ and $R_5$ is independently selected from hydrogen, substituted and unsubstituted $C_1$-$C_{10}$ alkyl groups, a substituted or nonsubstituted $C_6$-$C_{20}$ aryl group, substituted and unsubstituted $C_1$-$C_{10}$ alkoxy groups, fluorine, cyano groups, and amine groups. In some embodiments, adjacent R groups among $R_1$, $R_2$, $R_3$, $R_4$ and $R_5$ may bond with one another to form a saturated or unsaturated carbon ring.

When any one of $R_1$, $R_2$, $R_3$, $R_4$, $R_5$, $Ar_1$, $Ar_2$, X, and Y is an aryl group or a condensed polycyclic group with 21 or more carbon atoms, the molecular weight of the compound may be too large for easy deposition.

According to some embodiments of the present invention, the compound of Formula 1 may have a hole injection, hole transport, and/or emission function. In particular, if Y is a phenylcarbazole structure, the compound of Formula 1 will include at least two rigid phenylcarbazole structures, thereby increasing the glass transition temperature (Tg) or melting point. Moreover, if Y is a fluorene compound, and in particular, if a naphthalene group or an anthracene group is introduced, the glass transition temperature (Tg) or melting point increases, which is desirable.

According to embodiments of the present invention, the glass transition temperature (Tg) or melting point of the compound of Formula 1 is high. As a result, during field-emission, heat resistance is increased against Joule's heat produced inside the organic layers, between organic layers or between an organic layer and a metal electrode, and resistance is increased against a high temperature environment. Such organic light emitting devices manufactured using the compounds of Formula 1 are highly durable under both storing and operating conditions.

In some embodiments, X of Formula 1 is selected from substituents represented by the below structures.

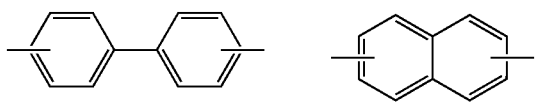

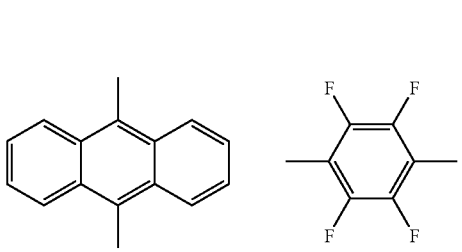

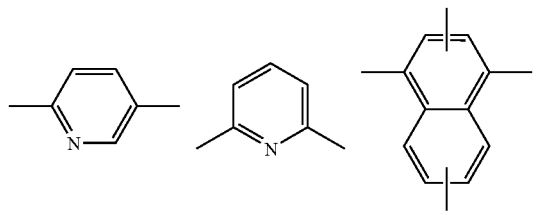

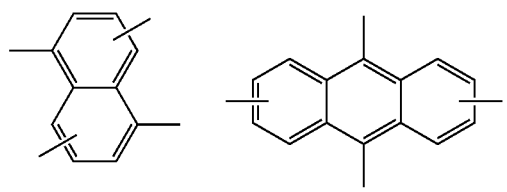

In one embodiment, the compound of Formula 1 may be a phenylcarbazole compound represented by Formula 4 or Formula 5 below.

Formula 4

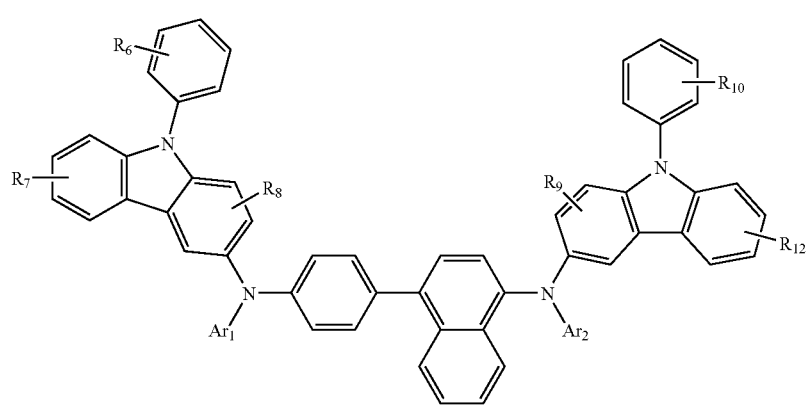

Formula 5

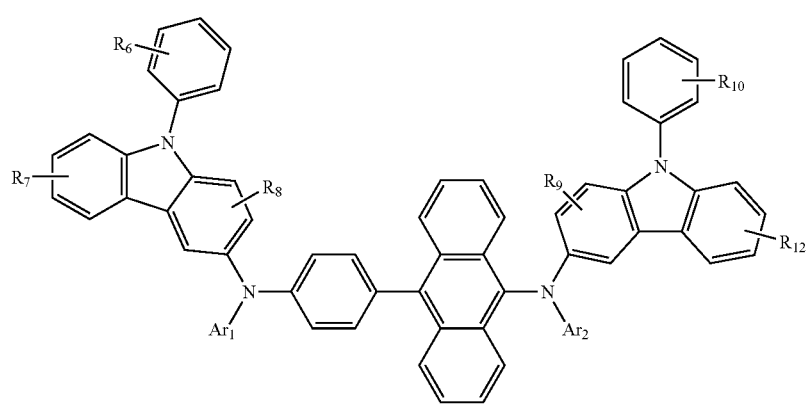

In Formulae 4 and 5, each of $R_6$, $R_7$, $R_8$, $R_9$, $R_{10}$, $R_{11}$ and $R_{12}$ is independently selected from hydrogen, substituted and unsubstituted $C_1$-$C_{10}$ alkyl groups, a substituted or nonsubstituted $C_6$-$C_{20}$ aryl group, substituted and unsubstituted $C_1$-$C_{10}$ alkoxy groups, fluorine, cyano groups, and amine groups. In some embodiments, adjacent R groups among $R_6$, $R_7$, $R_8$, $R_9$, $R_{10}$, $R_{11}$ and $R_{12}$ may bond with one another to form a saturated or unsaturated carbon ring. Each of $Ar_1$ and $Ar_2$ is independently selected from substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups.

In some embodiments, the compound of Formula 1 may be a fluorene compound represented by one of Formulae 6 to 8 below.

Formula 6

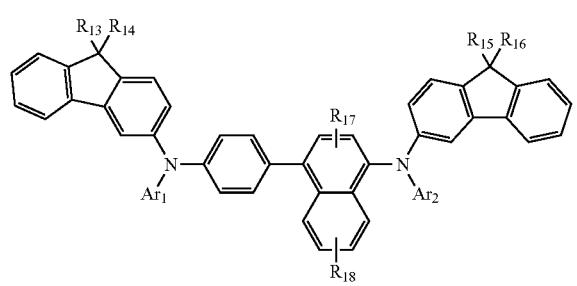

Formula 7

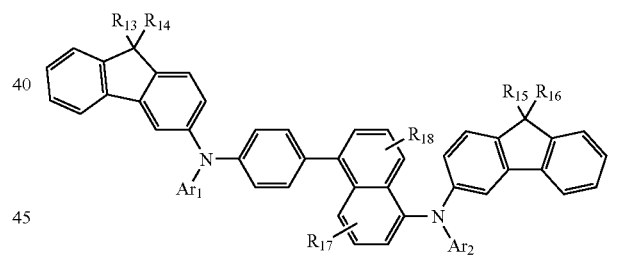

Formula 8

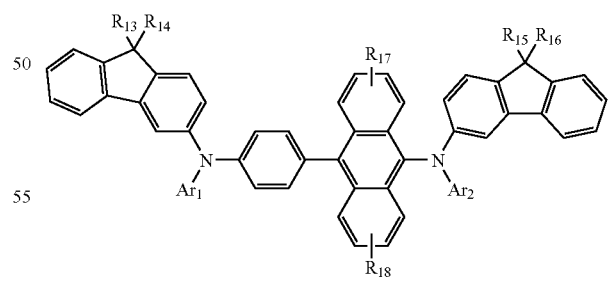

In Formula 6 through 8, each of $R_{13}$, $R_{14}$, $R_{15}$, $R_{16}$, $R_{17}$ and $R_{18}$ is independently selected from hydrogen, substituted and unsubstituted $C_1$-$C_{10}$ alkyl groups, a substituted or nonsubstituted $C_6$-$C_{20}$ aryl group, substituted and unsubstituted $C_1$-$C_{10}$ alkoxy groups, fluorine, cyano groups, and amine groups. In some embodiments, adjacent R groups among $R_{13}$, $R_{14}$, $R_{15}$, $R_{16}$, $R_{17}$ and $R_{18}$ may bond with one another to form a saturated or unsaturated carbon ring. Each of $Ar_1$ and $Ar_2$ is independently selected from substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups.

In one embodiment, each of $Ar_1$ and $Ar_2$ is independently selected from substituted and unsubstituted $C_6$-$C_{20}$ aryl groups, and substituted and unsubstituted $C_4$-$C_{20}$ heteroaryl groups. In another embodiment, each of $Ar_1$ and $Ar_2$ is independently selected from phenyl groups, $C_1$-$C_5$ alkylphenyl groups, $C_1$-$C_5$ alkoxyphenyl groups, cyanophenyl groups, phenoxyphenyl groups, fluorophenyl groups, naphthyl groups, $C_1$-$C_5$ alkylnaphthyl groups, $C_1$-$C_5$ alkoxynaphthyl groups, cyanonaphthyl groups, halonaphthyl groups, fluorenyl groups, carbazolyl groups, $C_1$-$C_5$ alkyl carbazolyl groups, biphenyl groups, $C_1$-$C_5$ alkyl biphenyl groups, $C_1$-$C_5$ alkoxy biphenyl groups and pyridyl groups.

Nonlimiting examples of suitable substituents for $Ar_1$ or $Ar_2$ include phenyl groups, ethylphenyl groups, ethylbiphenyl groups, o-, m-, or p-fluorophenyl groups, dichlorophenyl groups, dicyano groups, trifluorophenyl groups, methoxyphenyl groups, o-, m-, or p-toryl groups, mesityl groups, phenoxyphenyl groups, ($\alpha$, $\alpha$-dimethyl benzene)phenyl groups, (N,N'-dimethyl)aminophenyl groups, (N,N'-diphenyl)aminophenyl groups, pentalenyl groups, naphthyl groups, methylnaphthyl groups, anthracenyl groups, azulenyl groups, heptalenyl groups, acenaphthylenyl groups, fluorenyl groups, anthraquinolyl groups, phenanthryl groups, triphenylene groups, pentaphenyl groups, hexaphenyl groups, carbazolyl groups, and the like.

In another embodiment, each of $Ar_1$ and $Ar_2$ may be independently selected from aryl groups including from 1 to 3 rings selected from fluorenyl groups, carbazolyl groups, phenyl groups, naphthyl groups and biphenyl groups. Alternatively, the aryl group may be an aromatic ring substituted with one to three substituents selected from $C_1$-$C_4$ alkyl groups, $C_1$-$C_5$ alkoxy groups, cyano group, amine groups, phenoxy groups, phenyl groups, and halogen atoms.

Nonlimiting examples of suitable unsubstituted alkyl groups for use in the Formulae according to embodiments of the present invention include methyl groups, ethyl groups, propyl groups, isobutyl groups, sec-butyl groups, pentyl groups, iso-amyl groups, and hexyl groups. In some embodiments, at least one hydrogen of the alkyl group may be substituted with a substituent selected from halogen atoms, hydroxyl groups, nitro groups, cyano groups, amino groups, amidino groups, hydrazine groups, hydrazone groups, carboxylic acid groups and salts thereof, sulfonic acid groups and salts thereof, phosphoric acid groups and salts thereof, $C_1$-$C_{10}$ alkyl groups, $C_1$-$C_{10}$ alkenyl groups, $C_1$-$C_{10}$ alkynyl groups, $C_6$-$C_{10}$ aryl groups, $C_7$-$C_{10}$ arylalkyl groups, $C_4$-$C_{10}$ heteroaryl groups, and $C_5$-$C_{10}$ heteroarylalkyl groups.

Nonlimiting examples of suitable unsubstituted alkoxy groups for use in the Formulae according to embodiments of the present invention include methoxy groups, ethoxy groups, phenyloxy groups, cyclohexyloxy groups, naphthyloxy groups, isopropyloxy groups, and diphenyloxy groups. In some embodiments, at least one hydrogen atom of the alkoxy group may be substituted with the same substituent groups as previously described with respect to the alkyl groups.

The unsubstituted aryl group, either by itself or in combination, refers to an aromatic carbon ring including at least one ring, wherein the rings may be attached in a pendant configuration, or may be fused. At least one hydrogen atom of the aryl group may be substituted with the same substituent groups as previously described with respect to the alkyl groups.

Nonlimiting examples of suitable unsubstituted aryloxy groups for use in the Formulae according to embodiments of the present invention include phenyloxy groups, naphthyloxy groups, and diphenyloxy groups. In some embodiments, at least one hydrogen atom of the aryloxy group may be substituted with the same substituent groups as previously described with respect to the alkyl groups.

The unsubstituted heteroaryl group refers to a monovalent monocyclic or divalent bicyclic aromatic organic compound with from 4 to 30 ring atoms including 1, 2, or 3 heteroatoms selected from N, O, P, and S, and wherein the remaining ring atoms are C. In some embodiments, at least one hydrogen atom of the heteroaryl group may be substituted with the same substituent groups as previously described with respect to the alkyl groups.

Nonlimiting examples of suitable heteroaryl groups include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, and indolyl groups.

Nonlimiting examples of suitable compounds satisfying Formula 1 included Compounds 1 to 242 below.

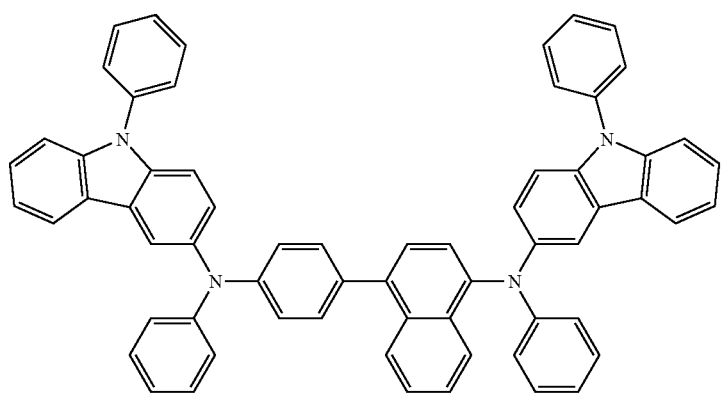

1

2
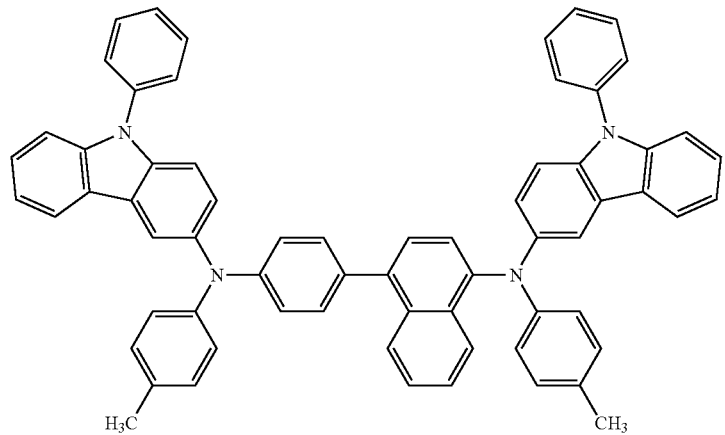
3
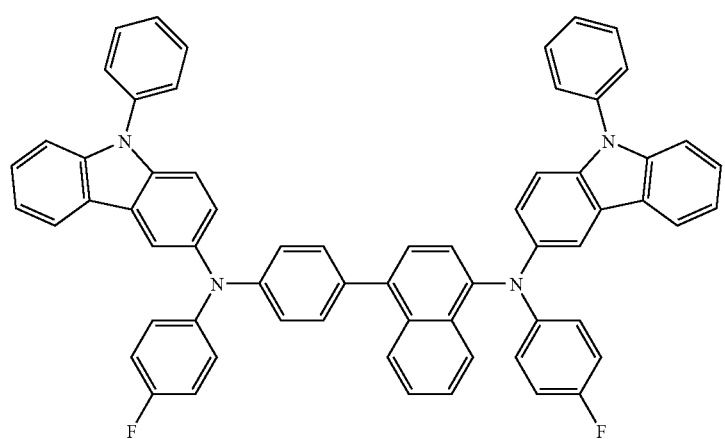
4
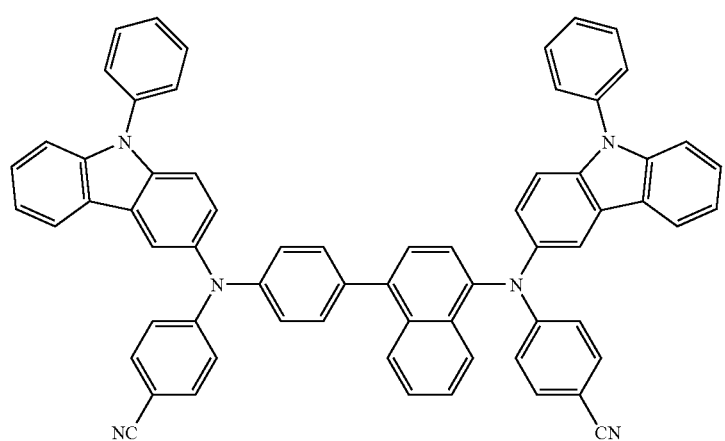

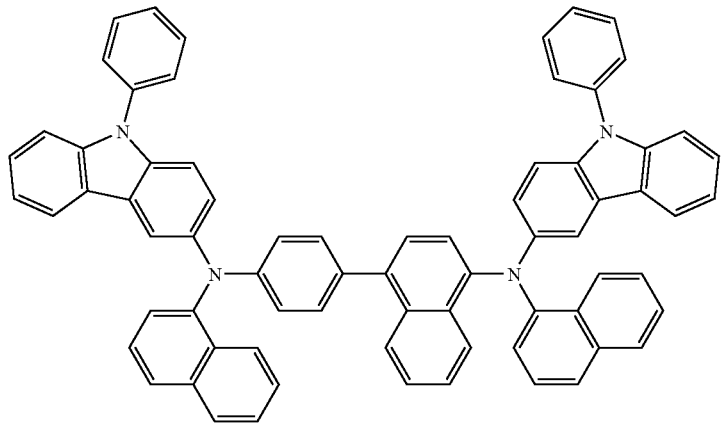
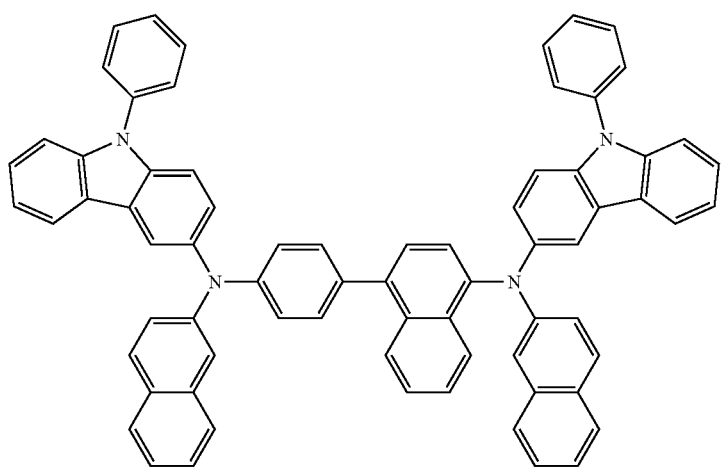
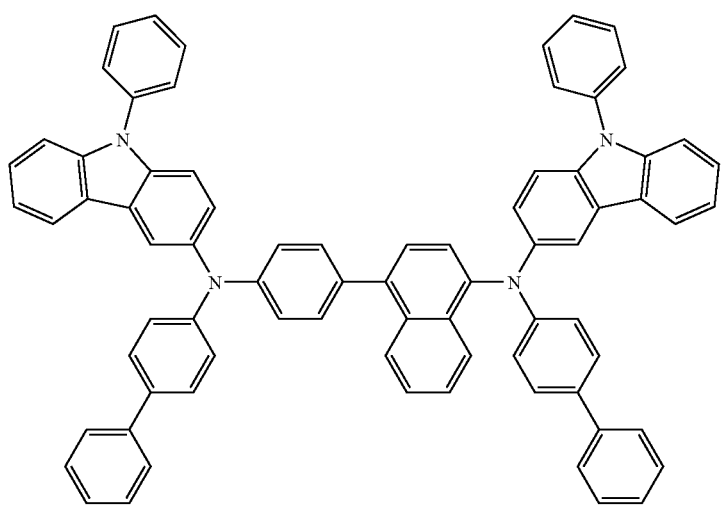

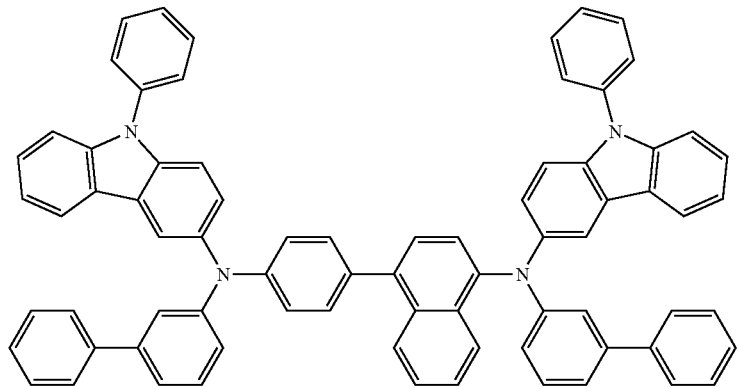
8
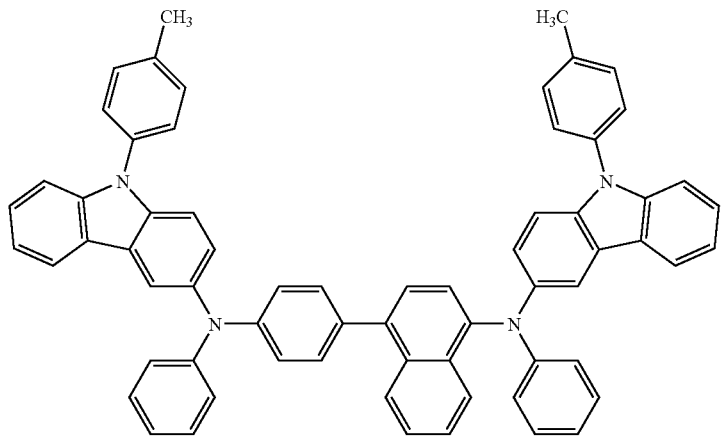
9
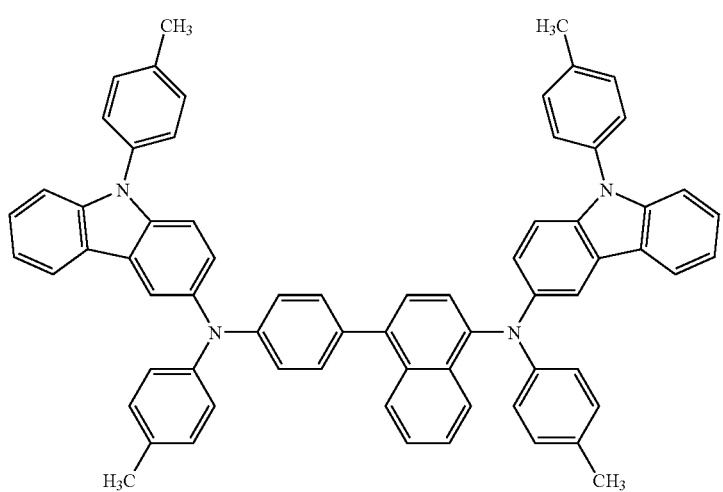
10

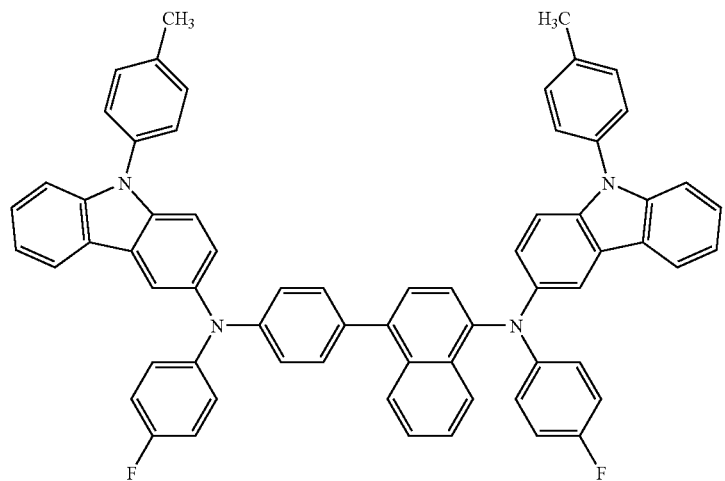
11
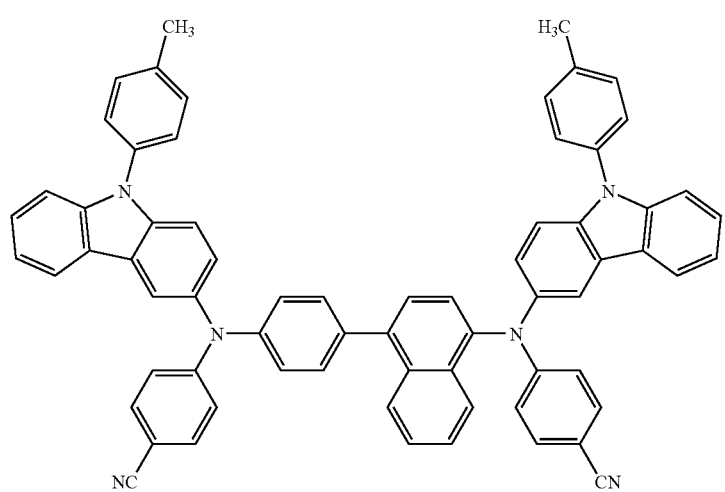
12
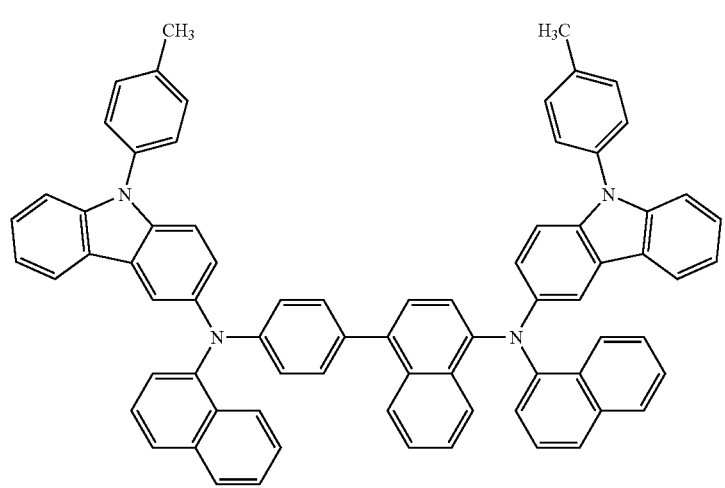
13

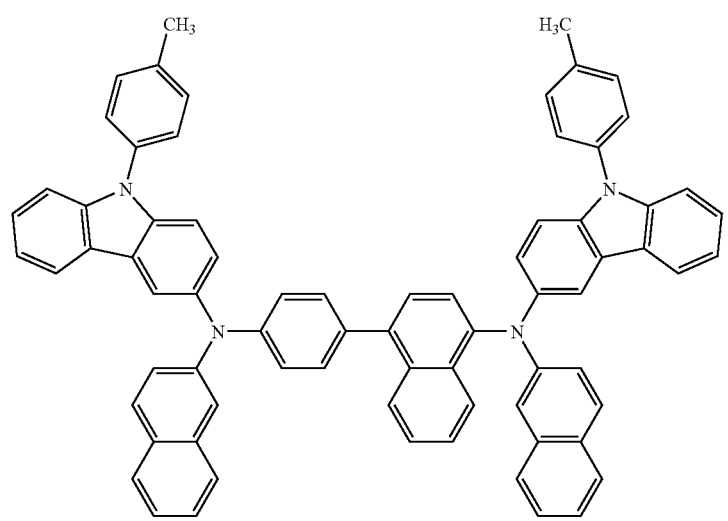
14
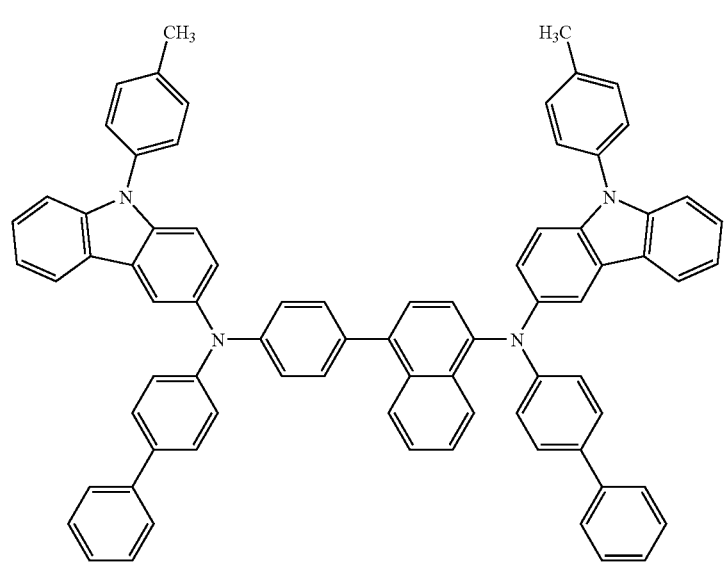
15
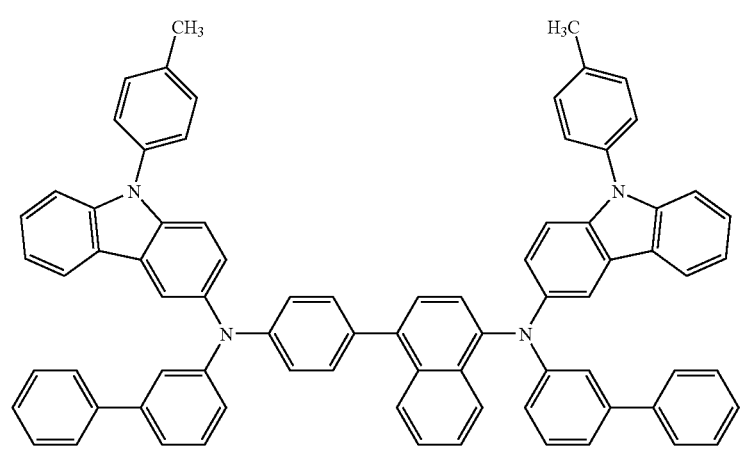
16

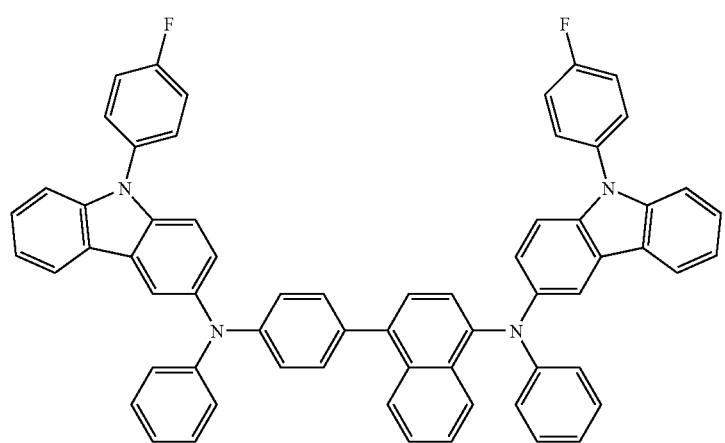
17
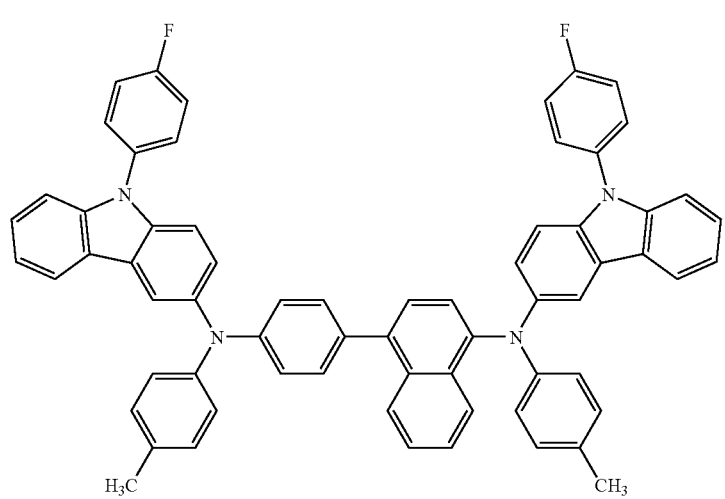
18
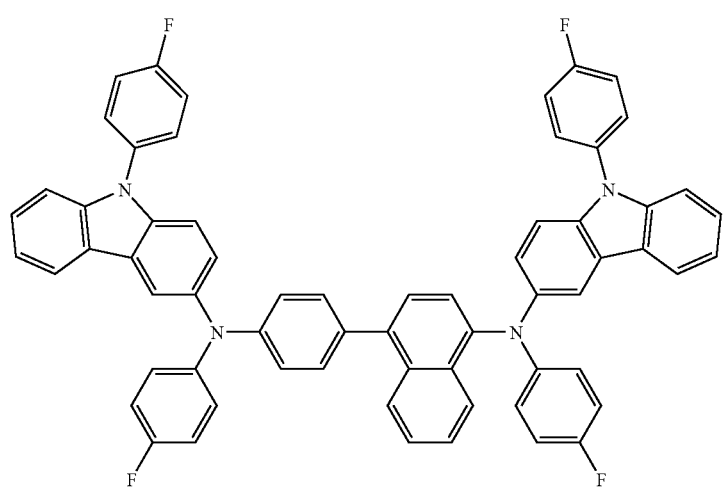
19

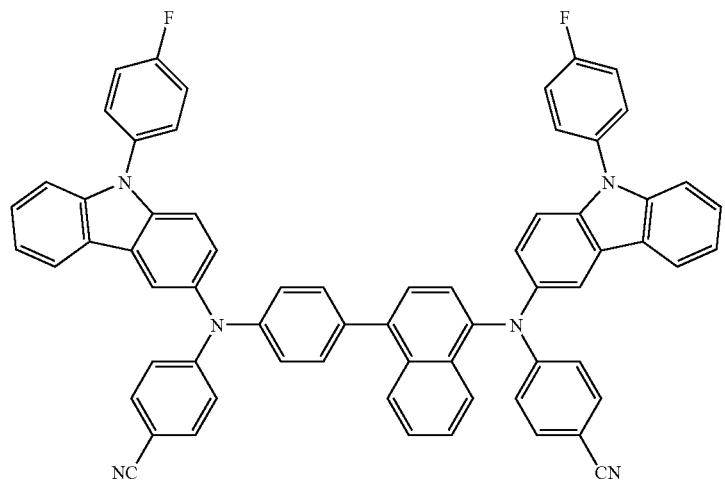
20
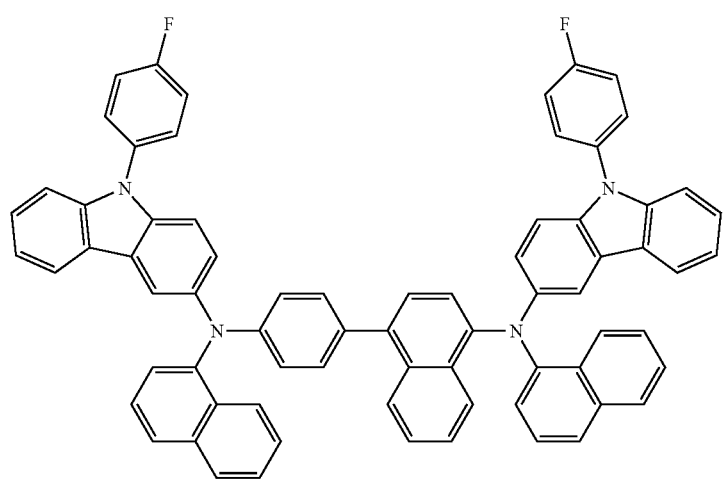
21
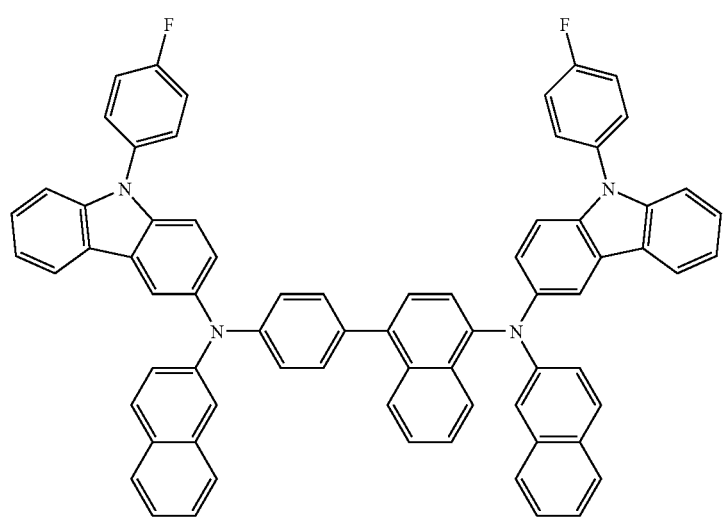
22

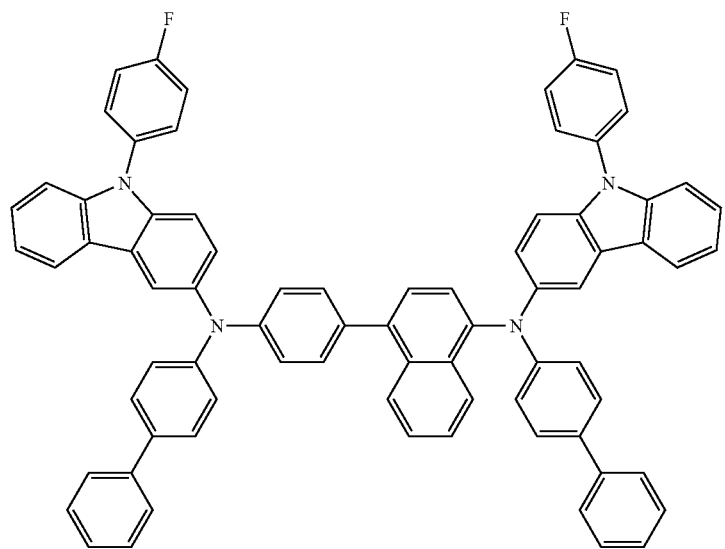
23
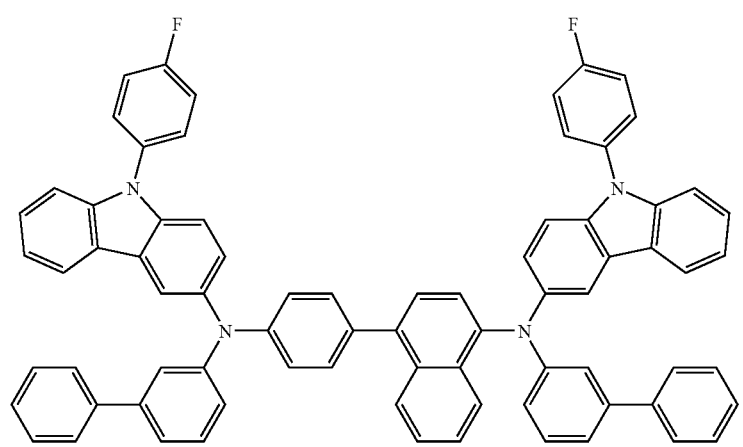
24
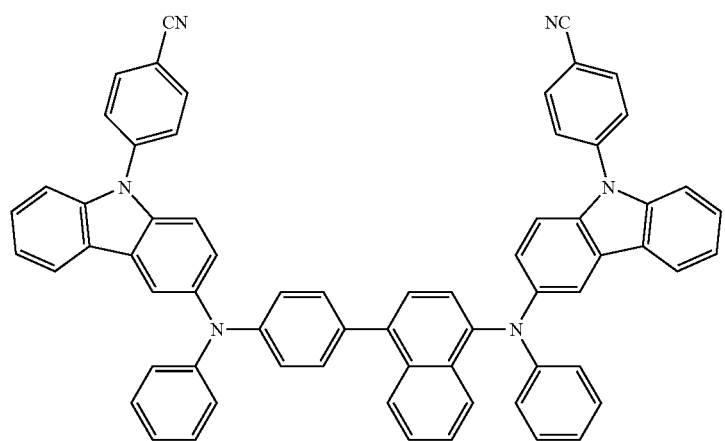
25

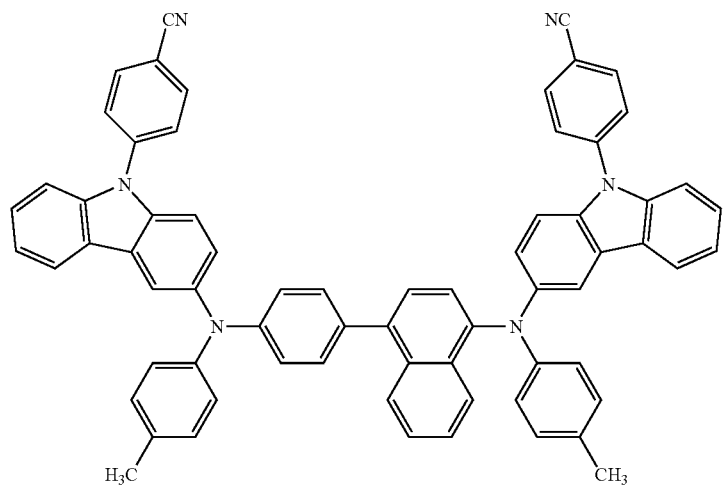
26
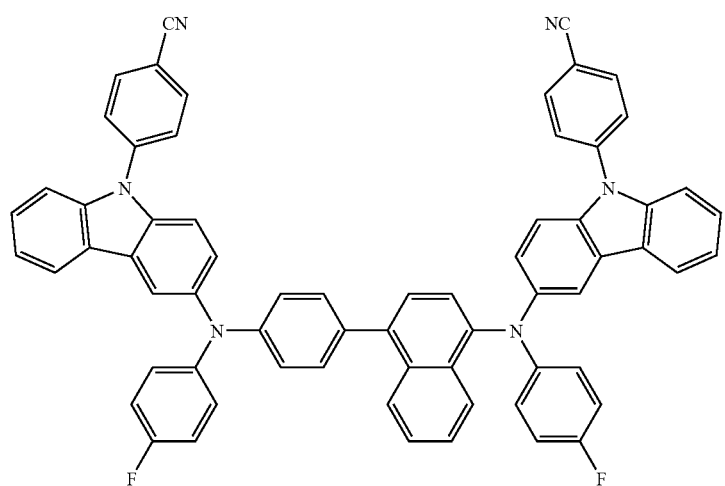
27
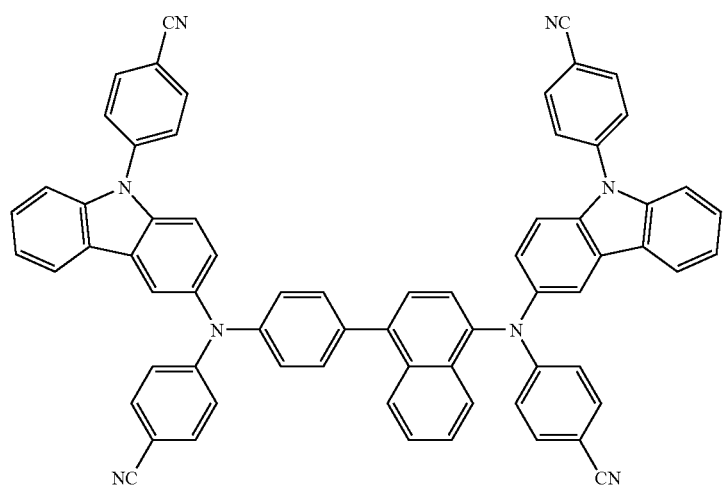
28

29
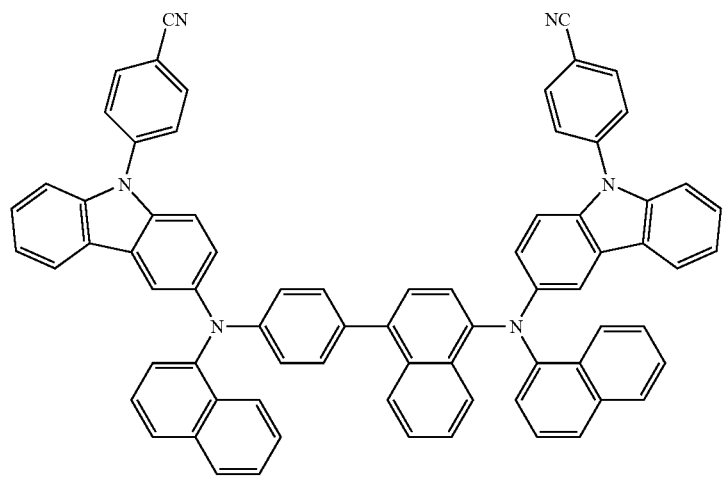
30
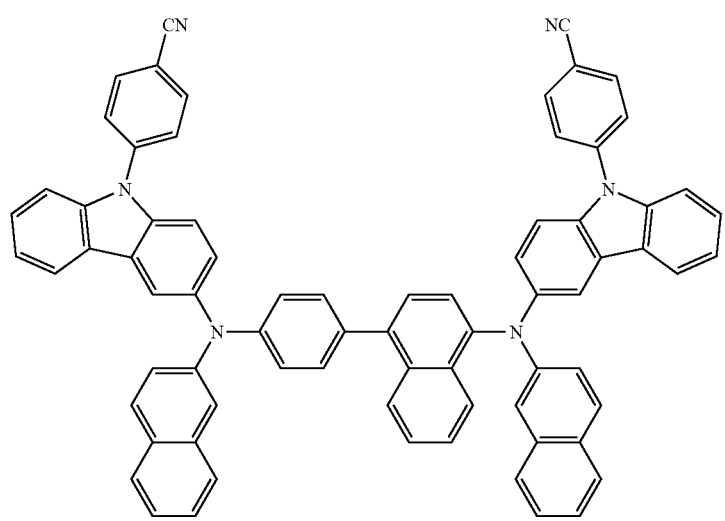
31
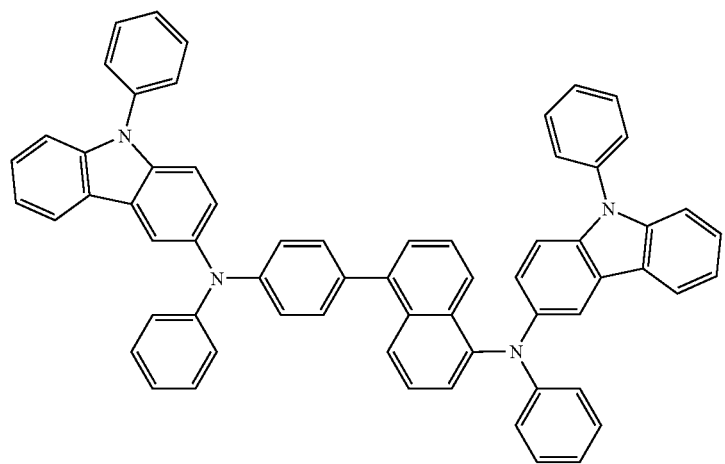

32
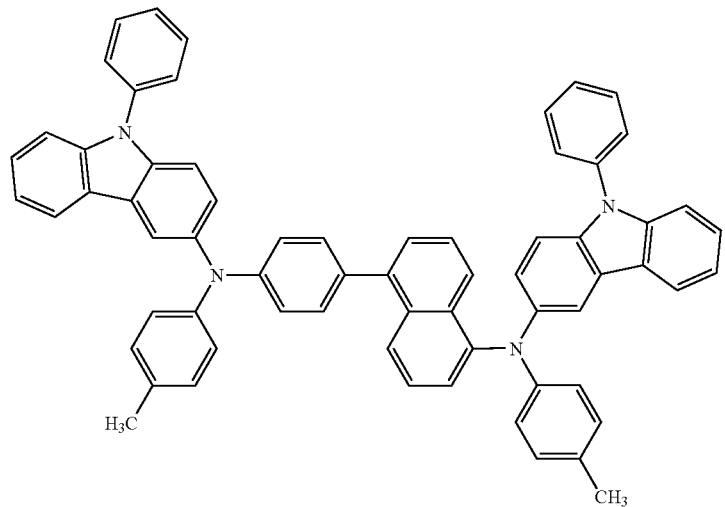
33
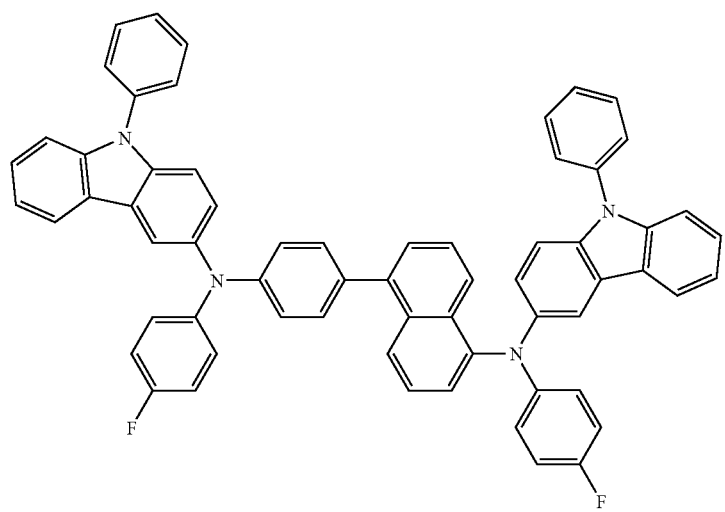
34
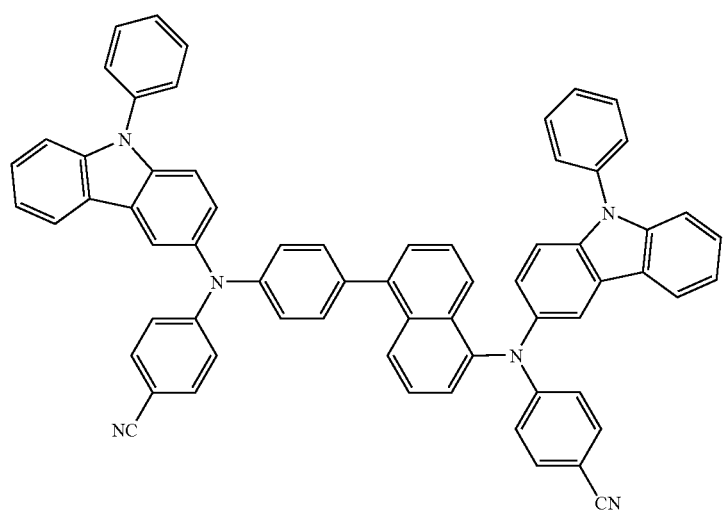

35
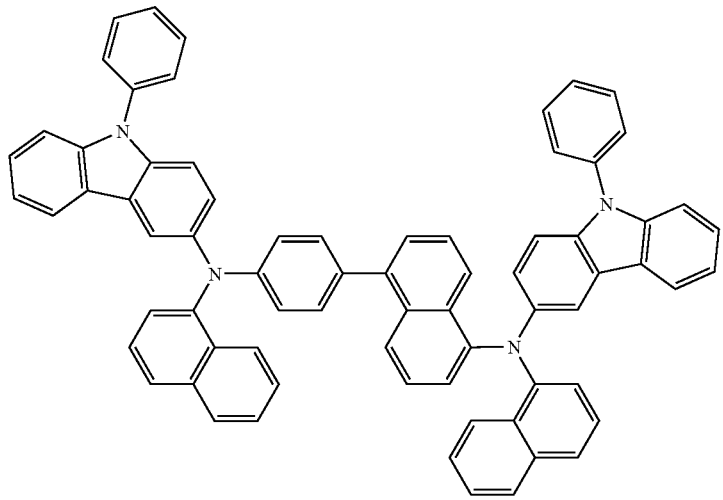
36
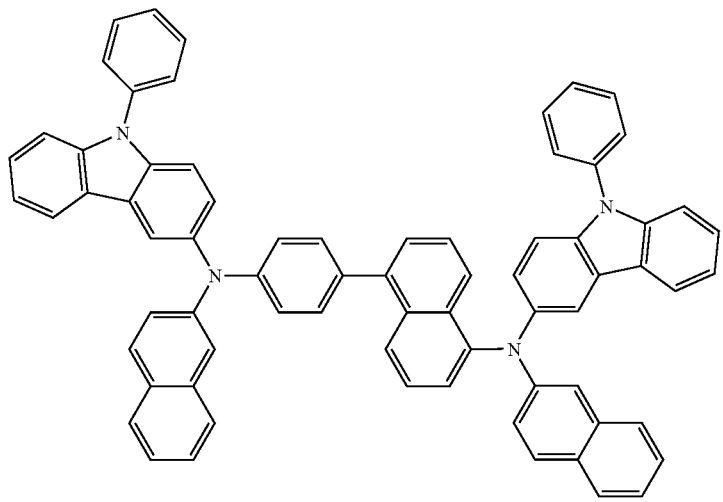
37
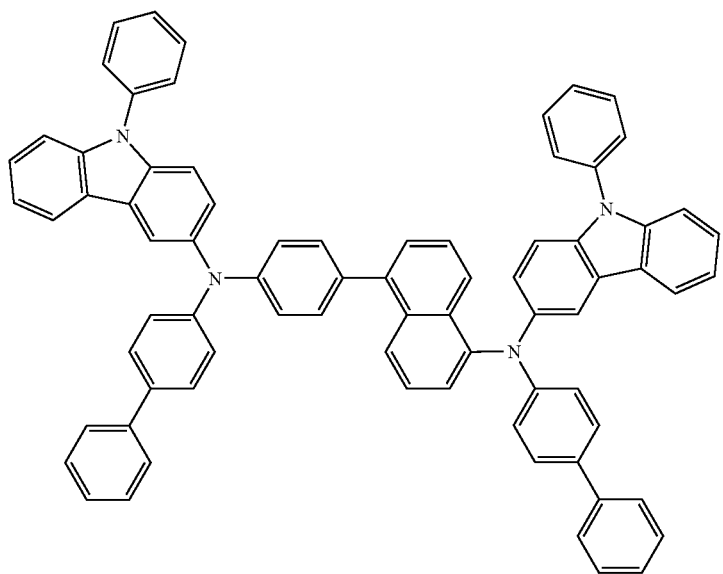

38
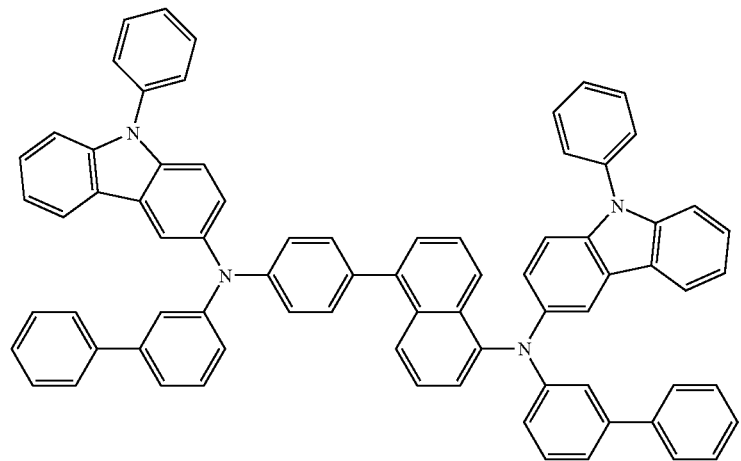
39
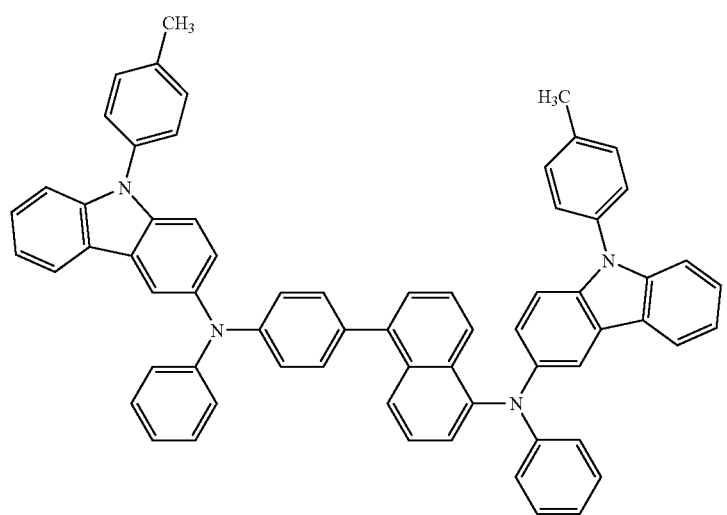
40
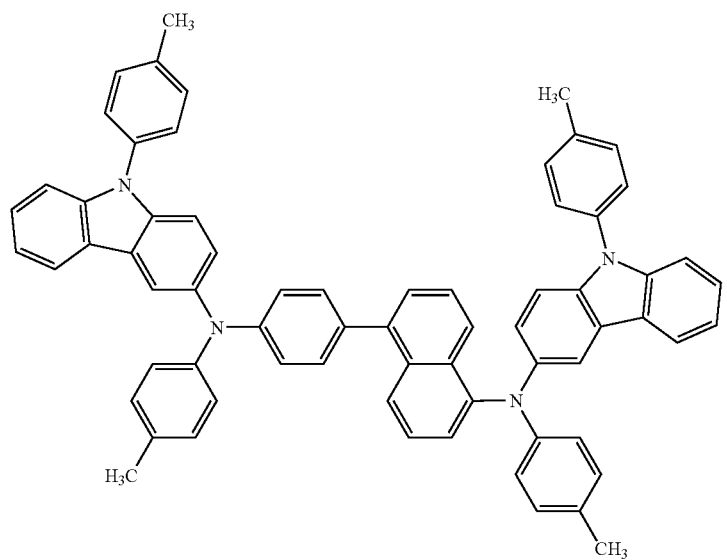

41
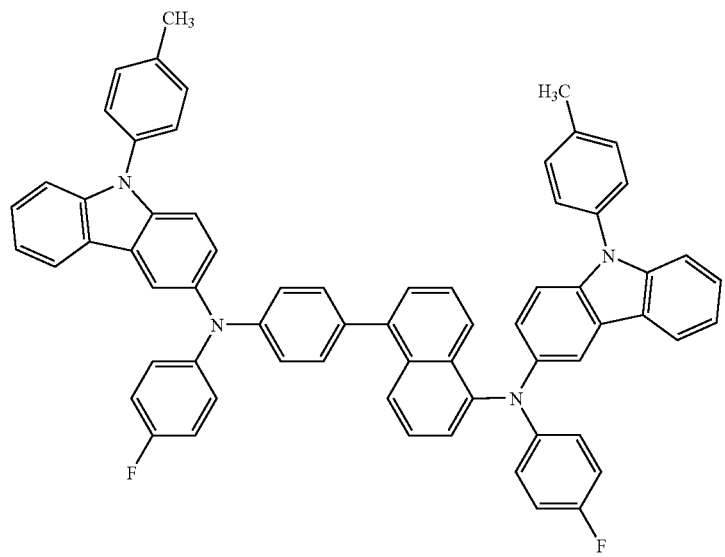
42
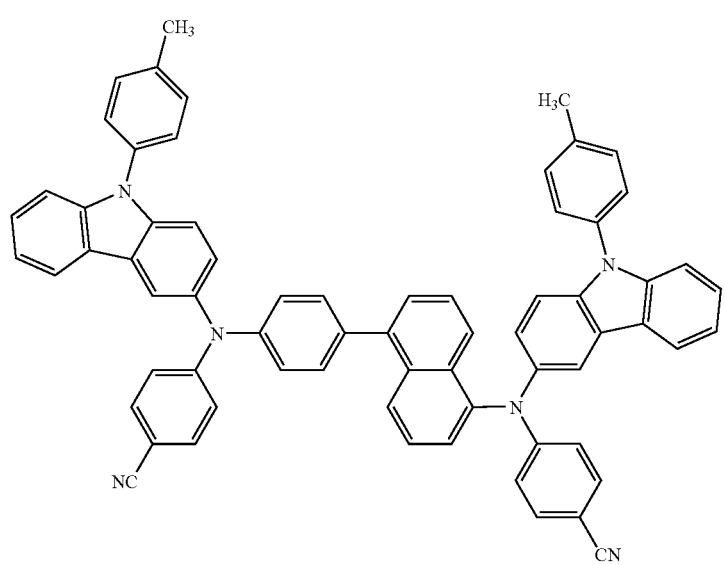
43
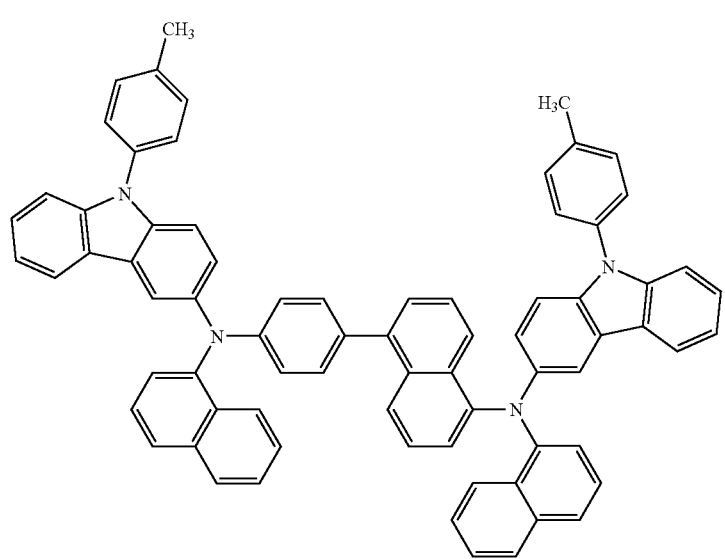

44
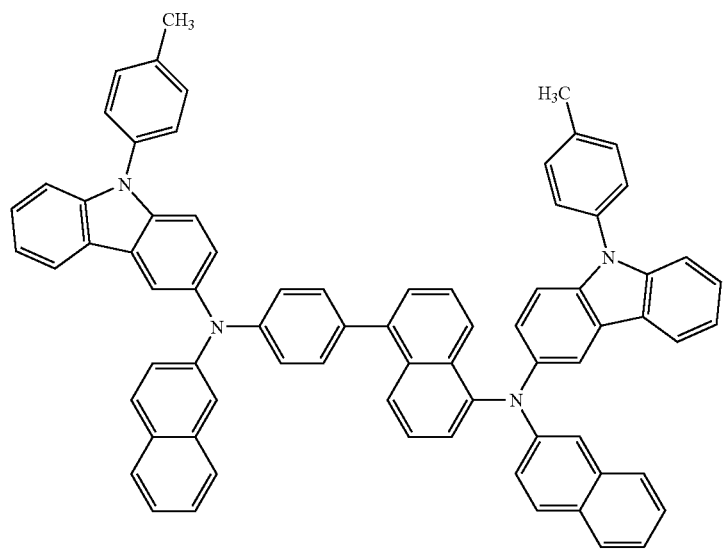
45
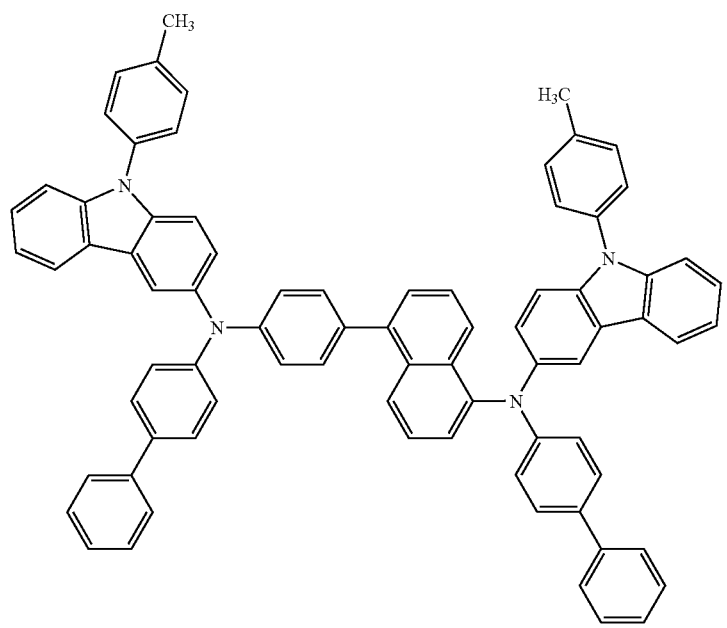
46
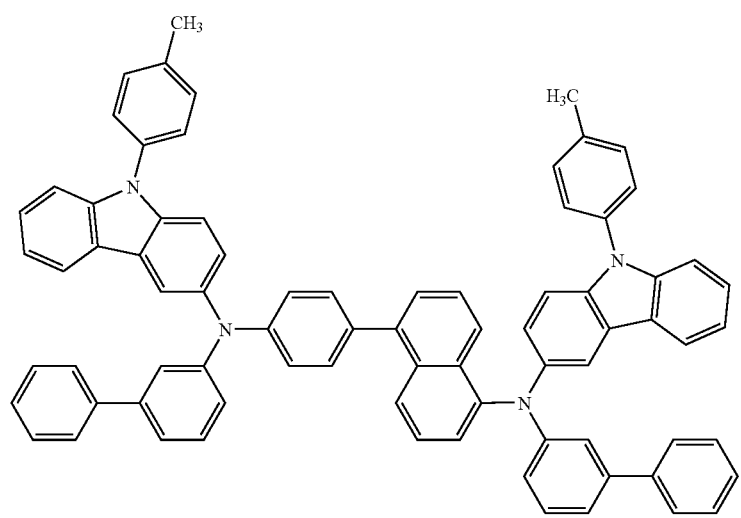

47
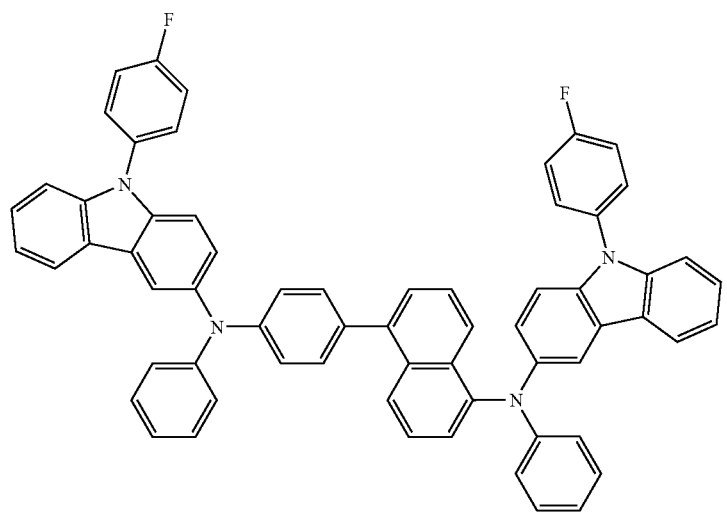
48
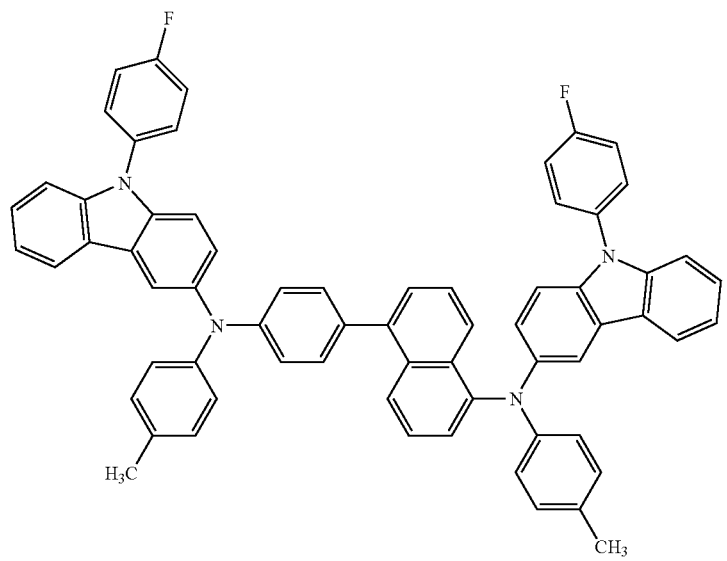
49
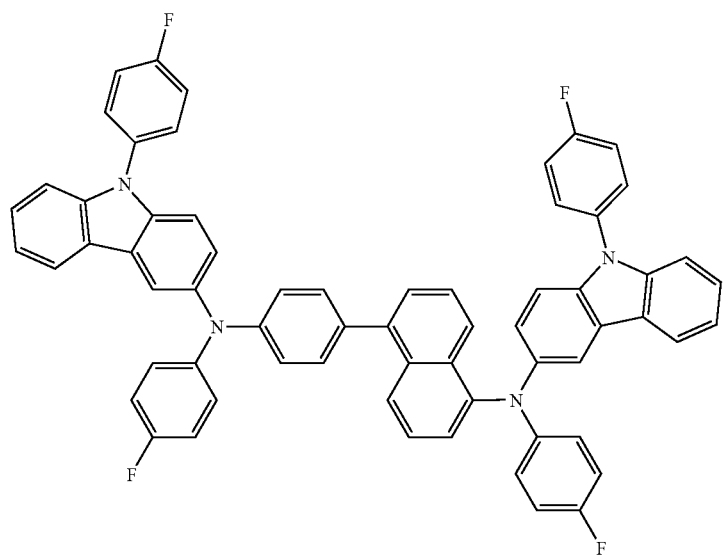

50
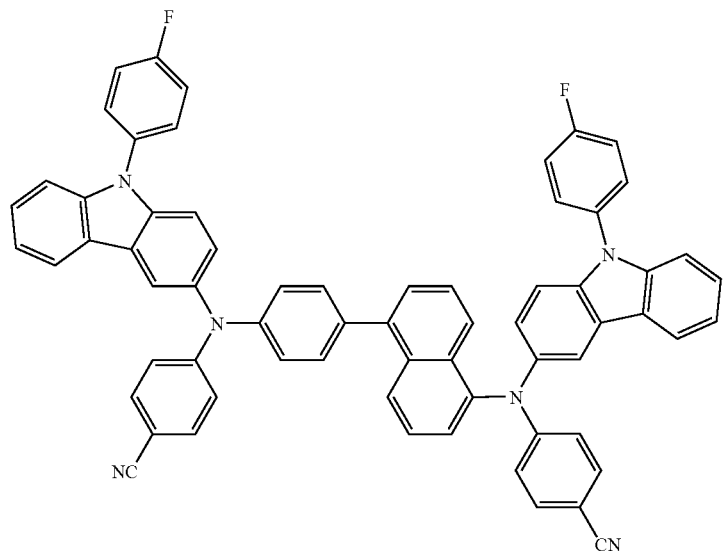
51
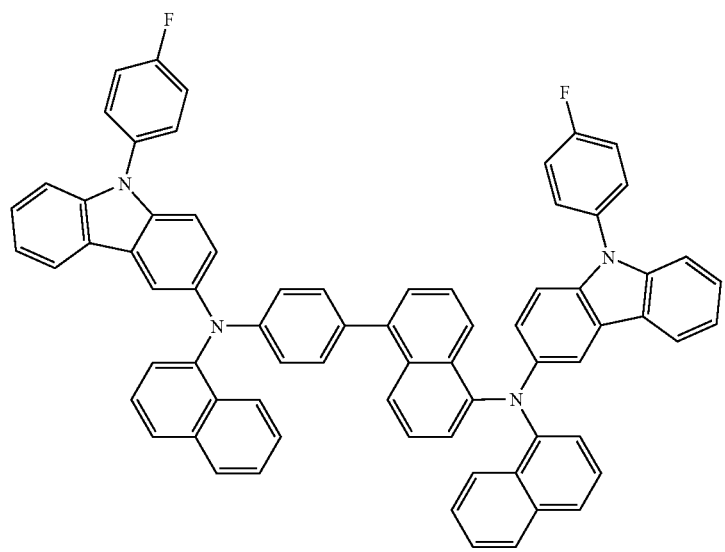
52
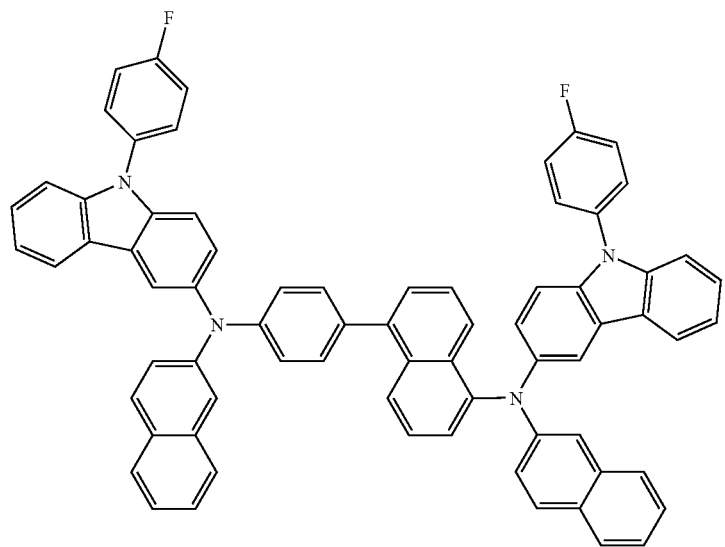

53
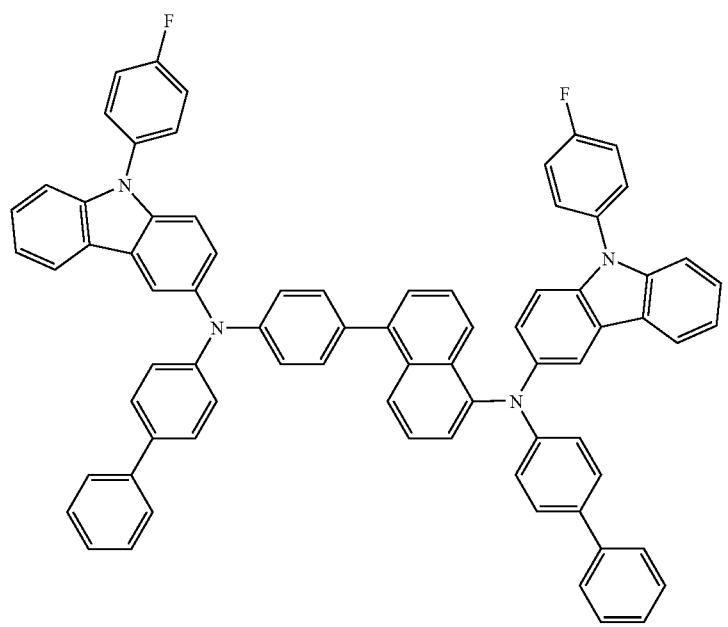
54
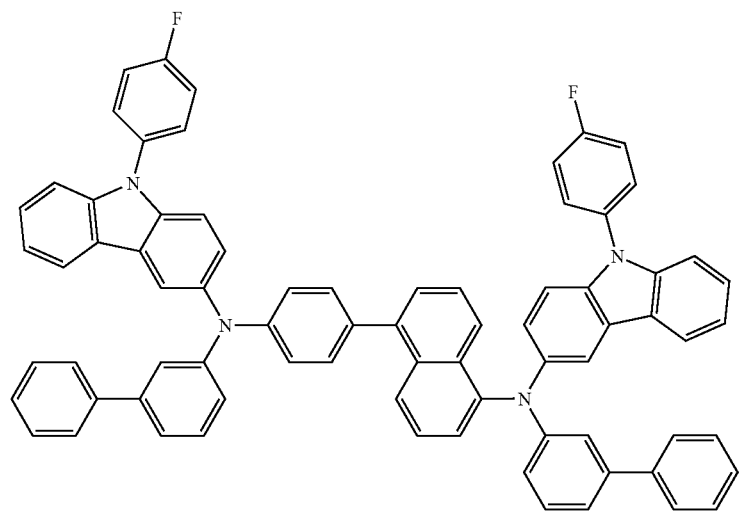
55
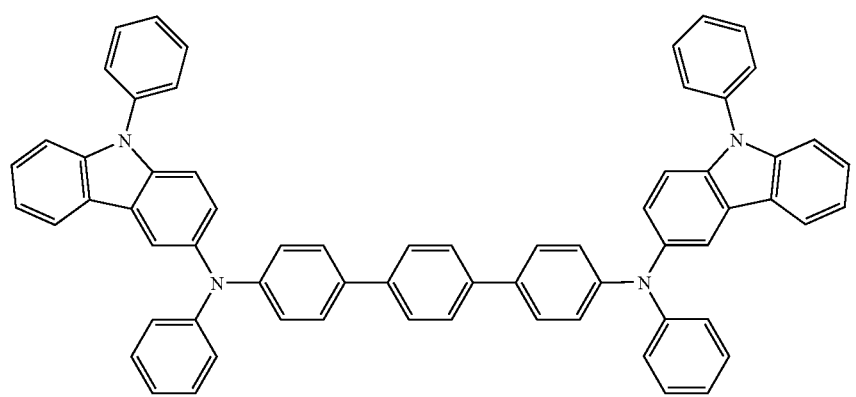

-continued
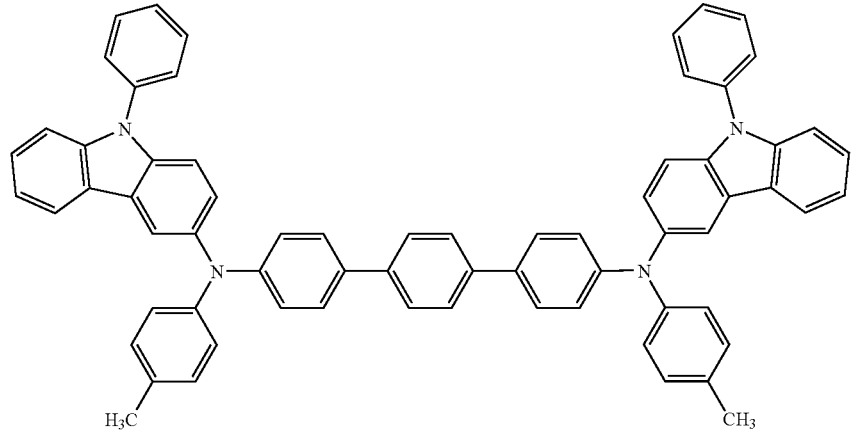
56
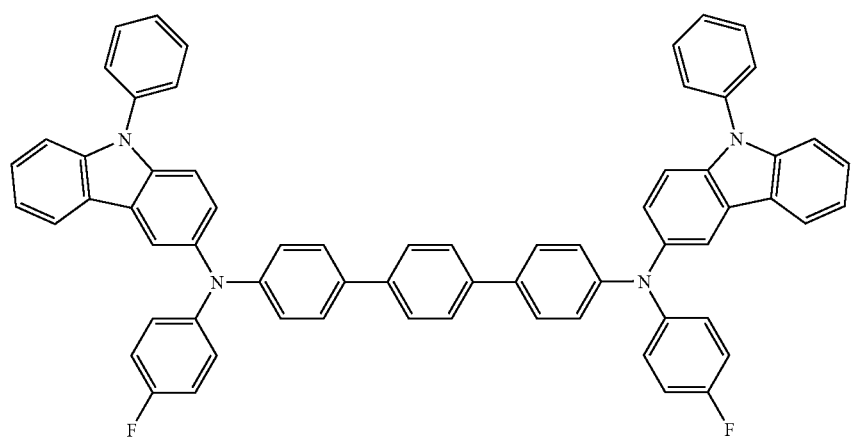
57
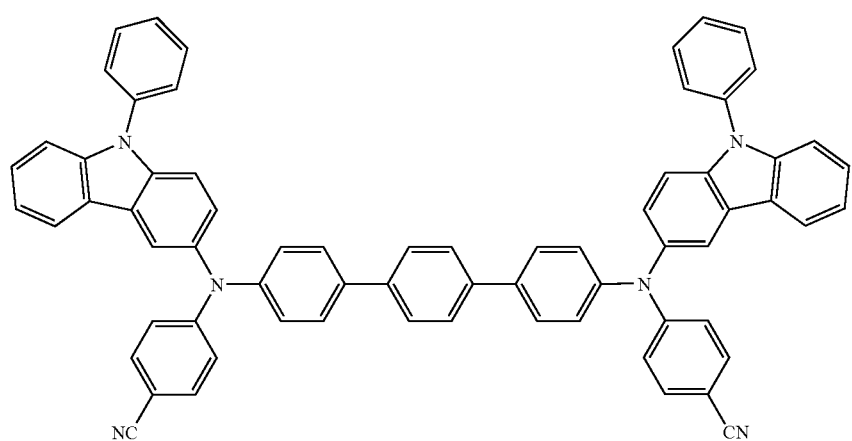
58

-continued
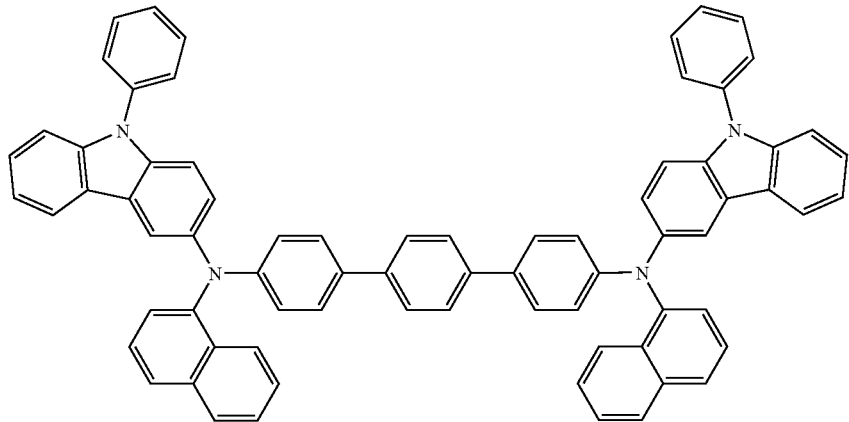
59
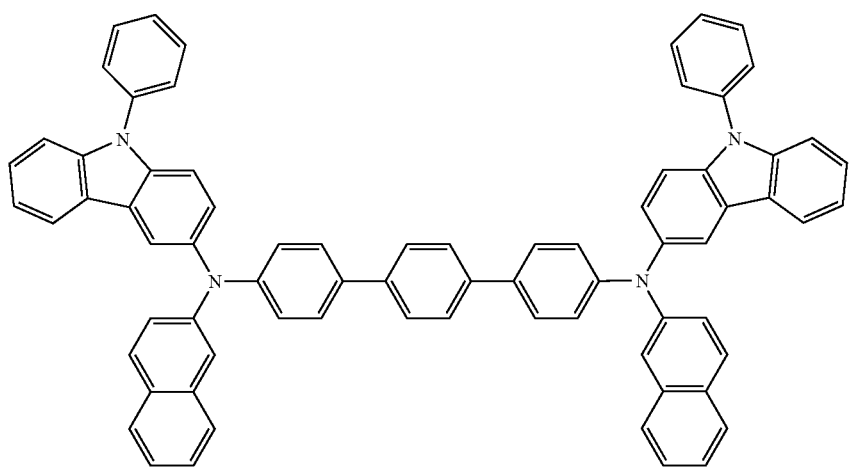
60
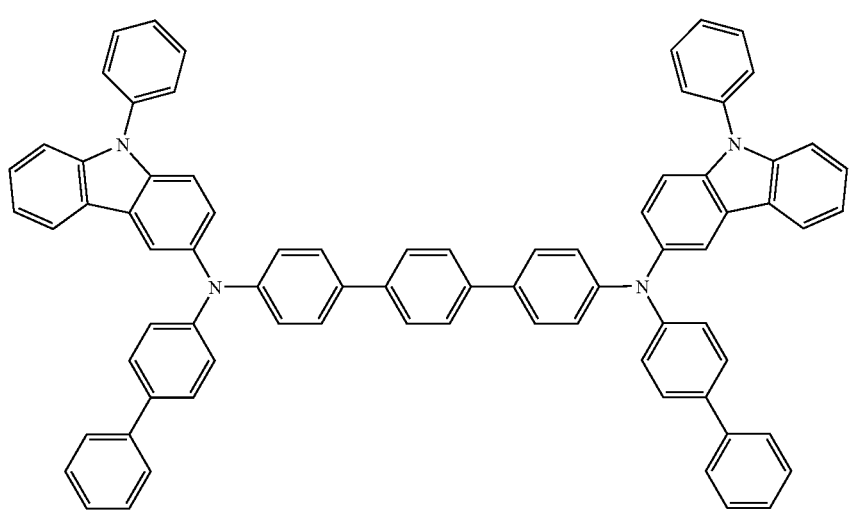
61

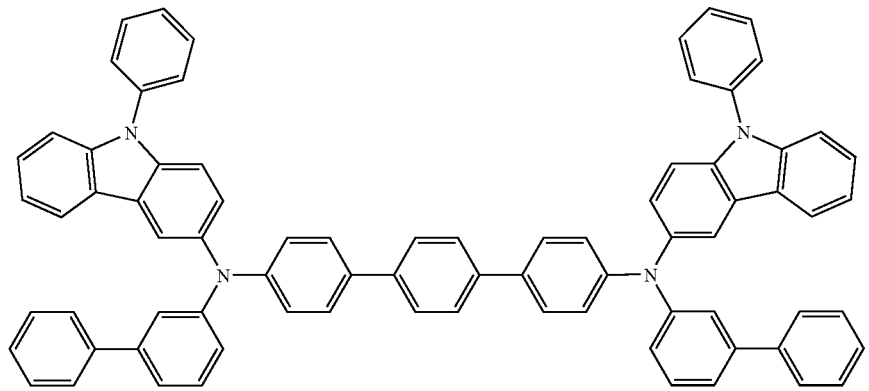
62
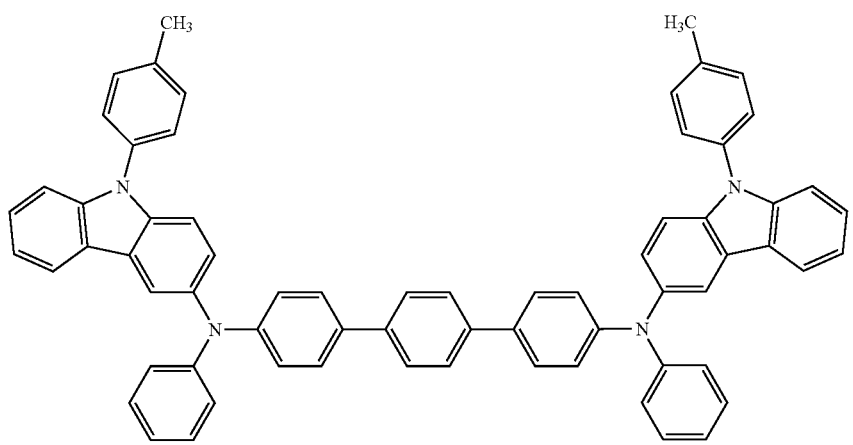
63
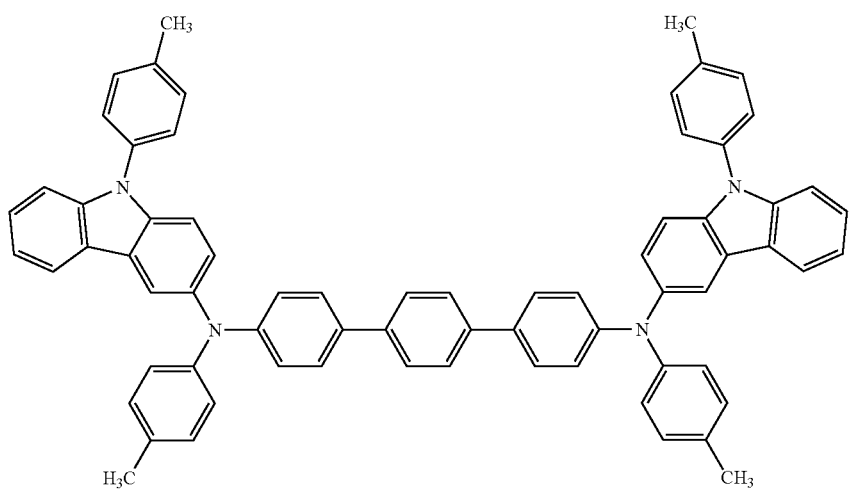
64

65
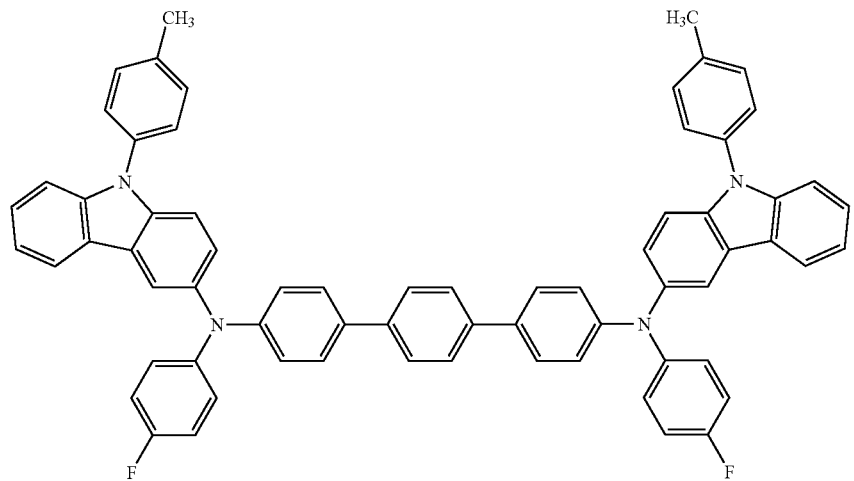
66
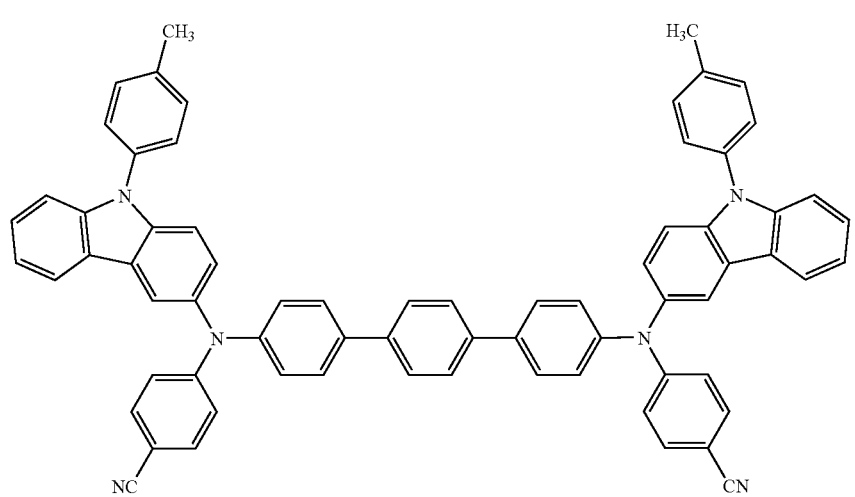
67
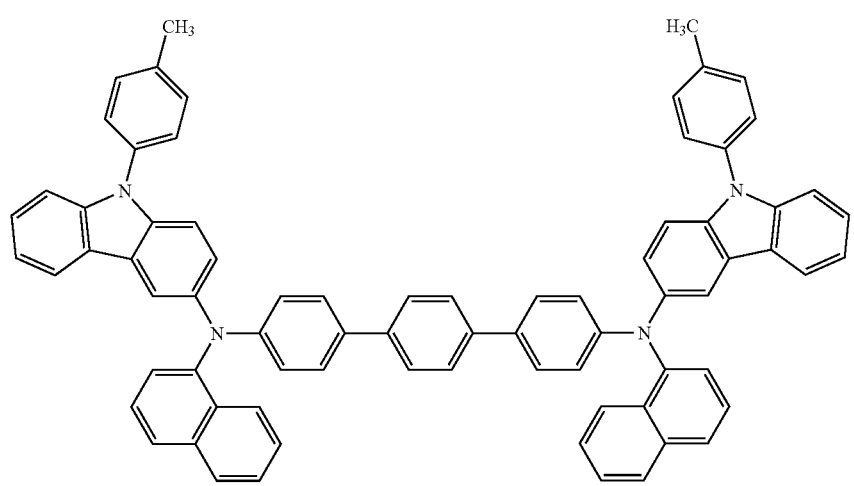

68
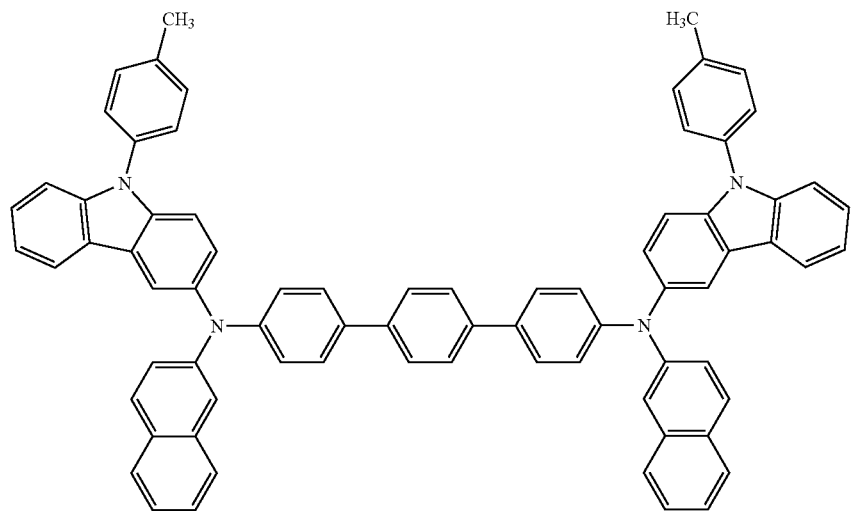
69
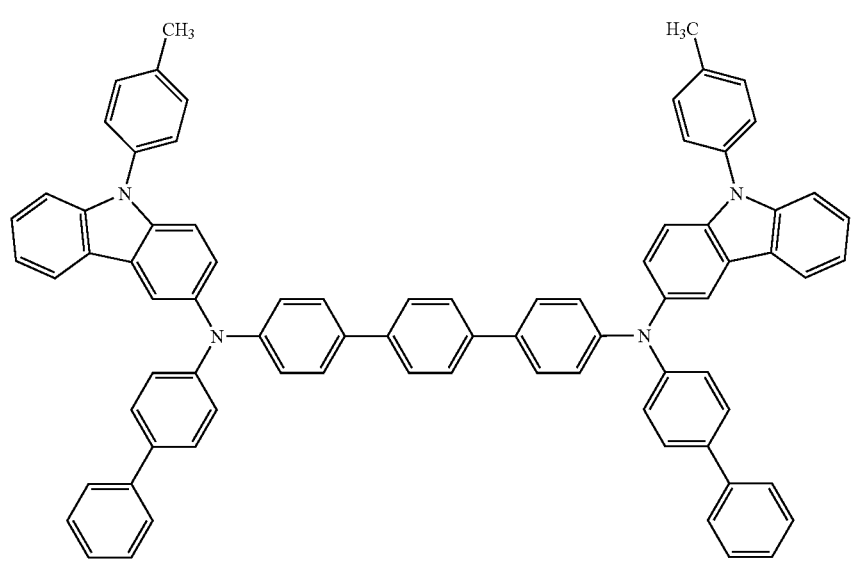
70
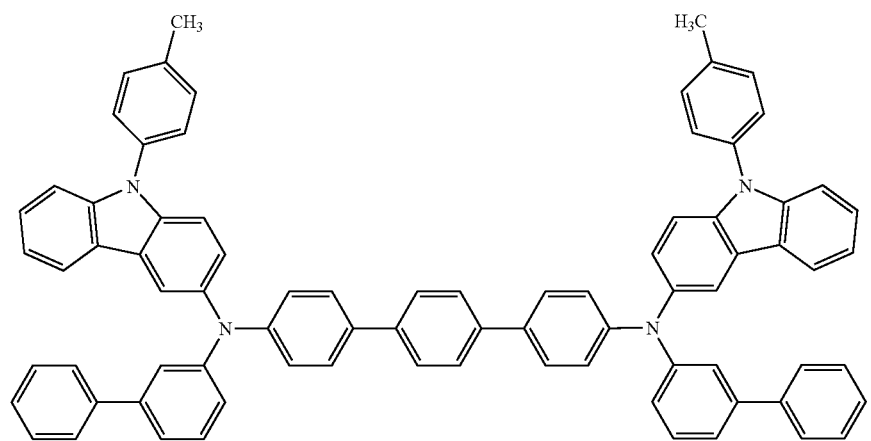

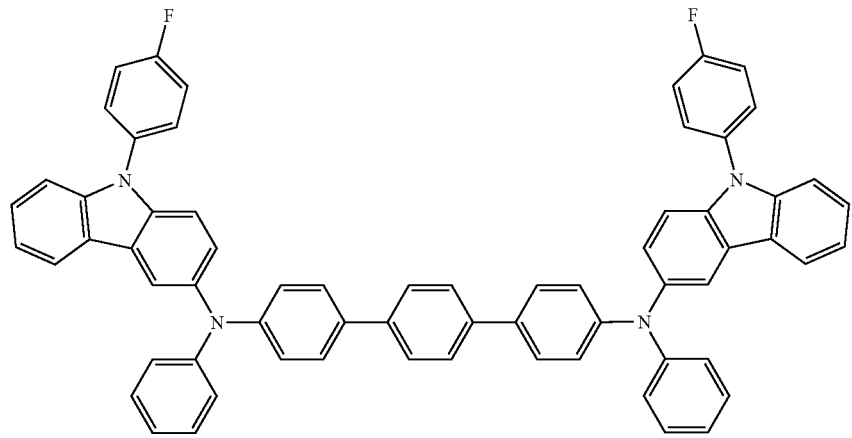
71
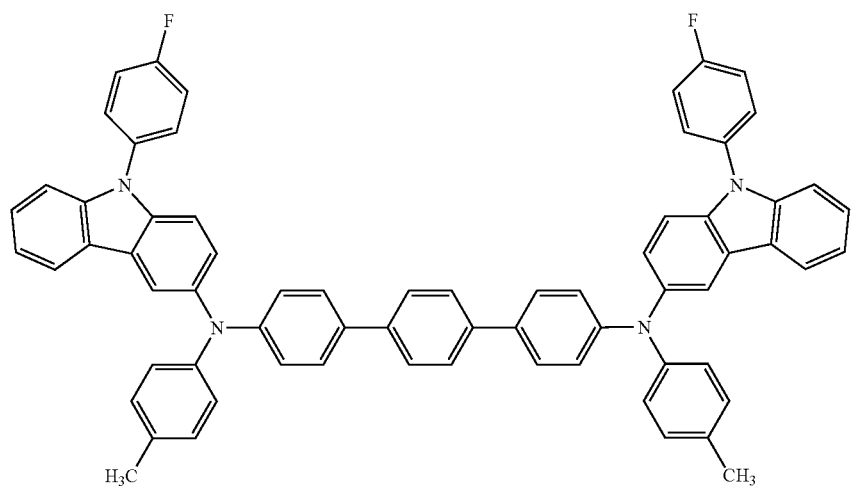
72
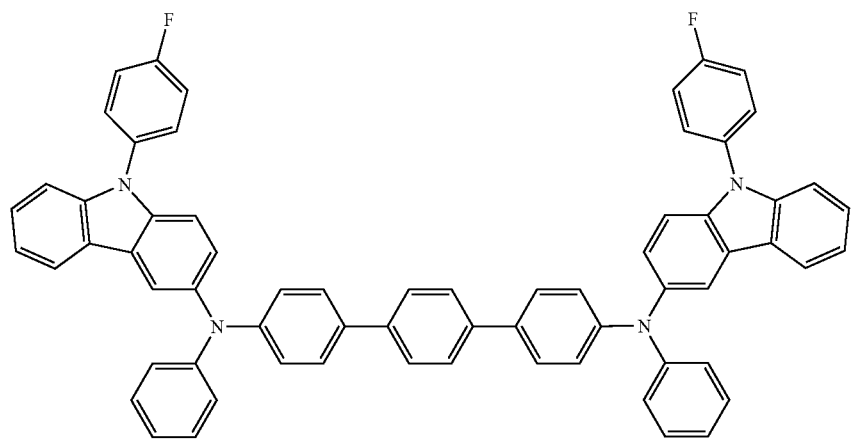
73

74
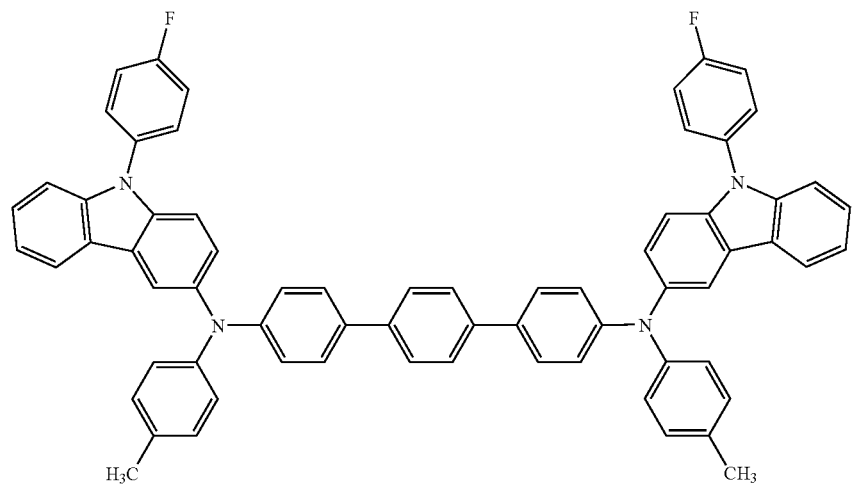
75
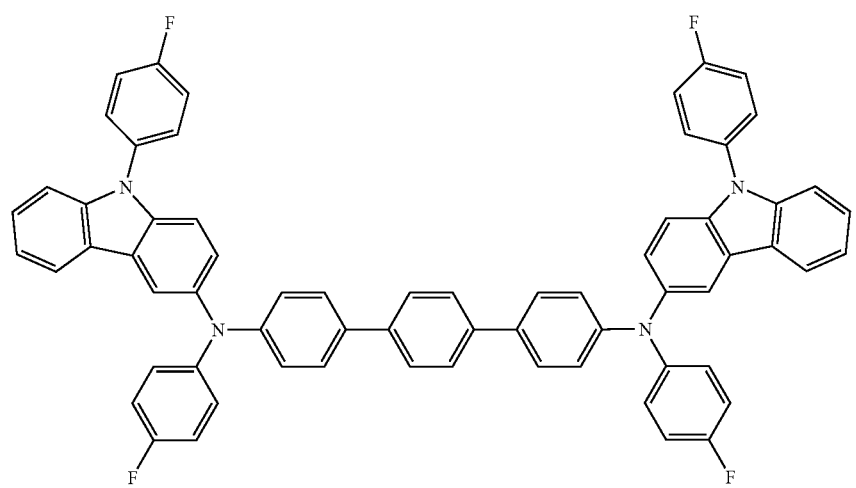
76
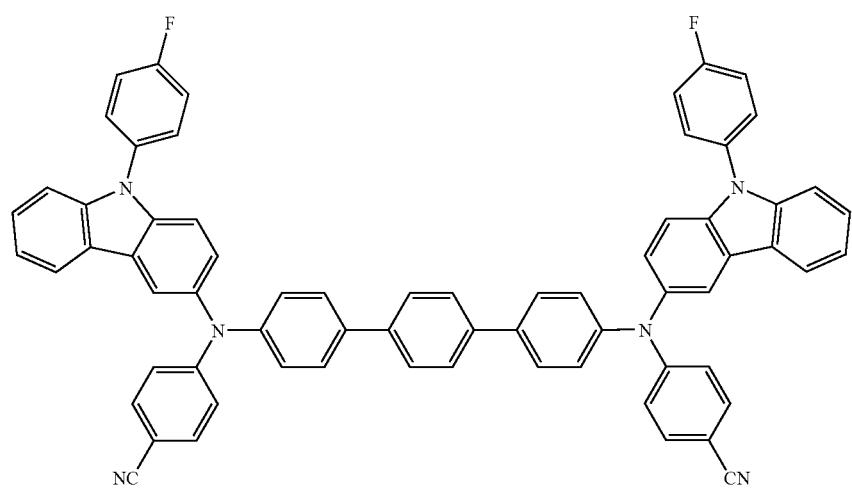

77
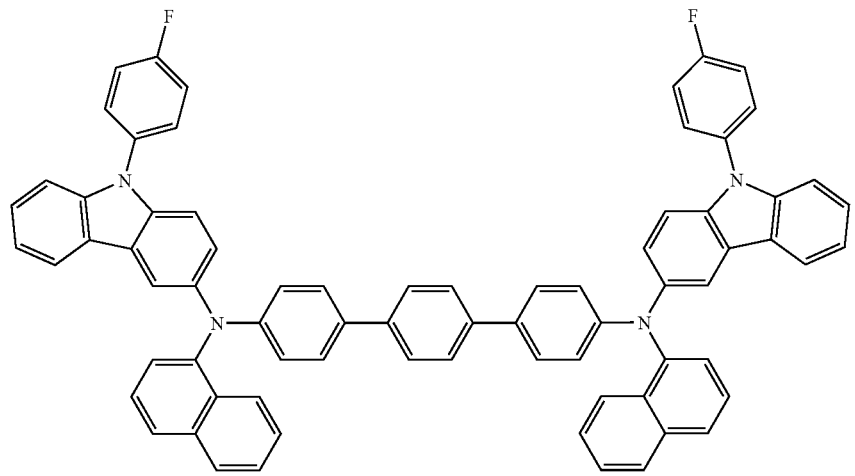
78
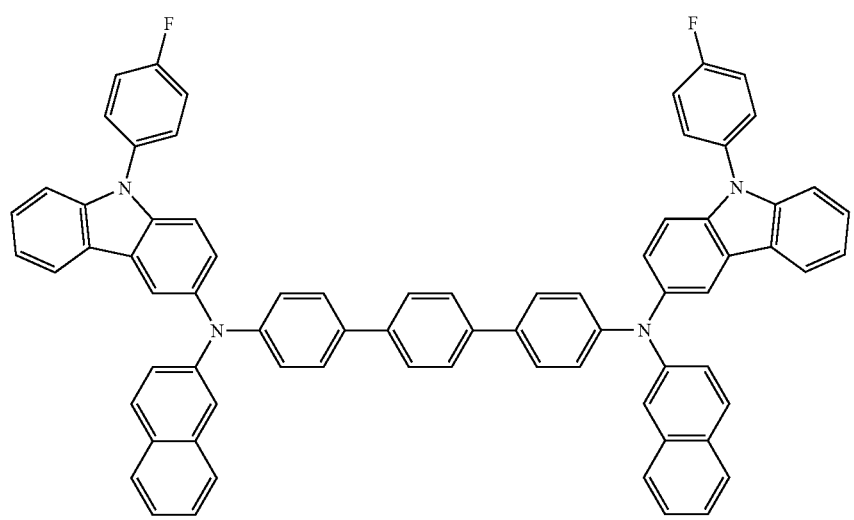
79
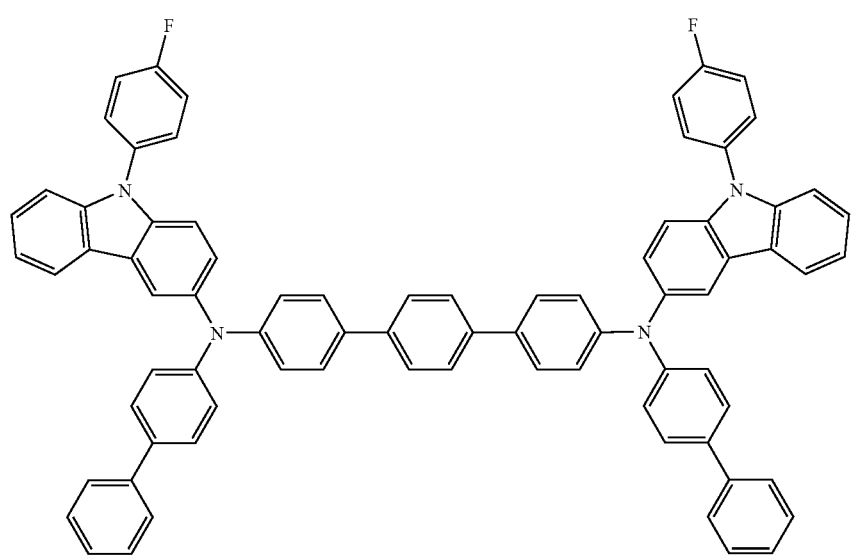

80
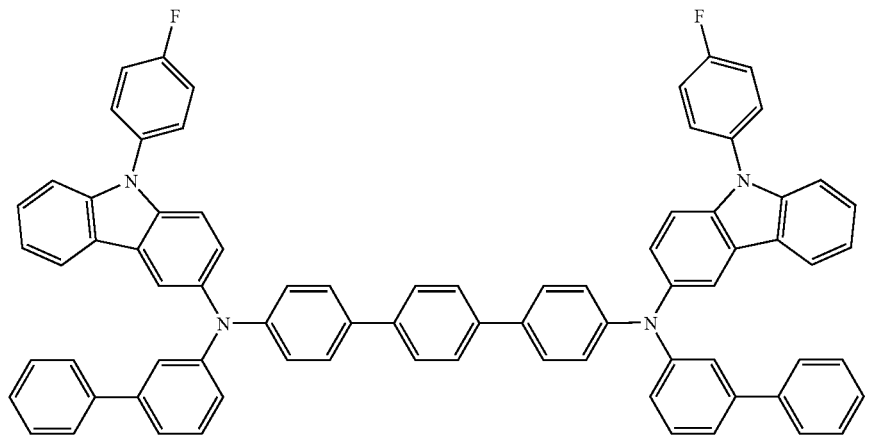
81
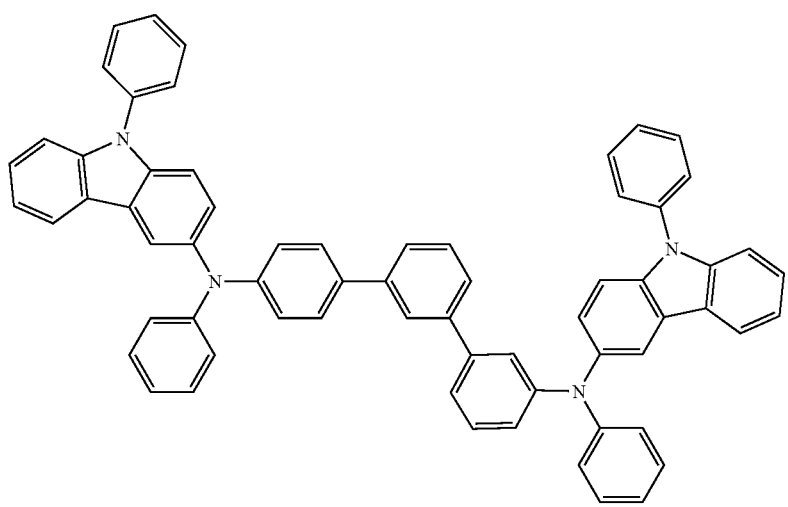
82
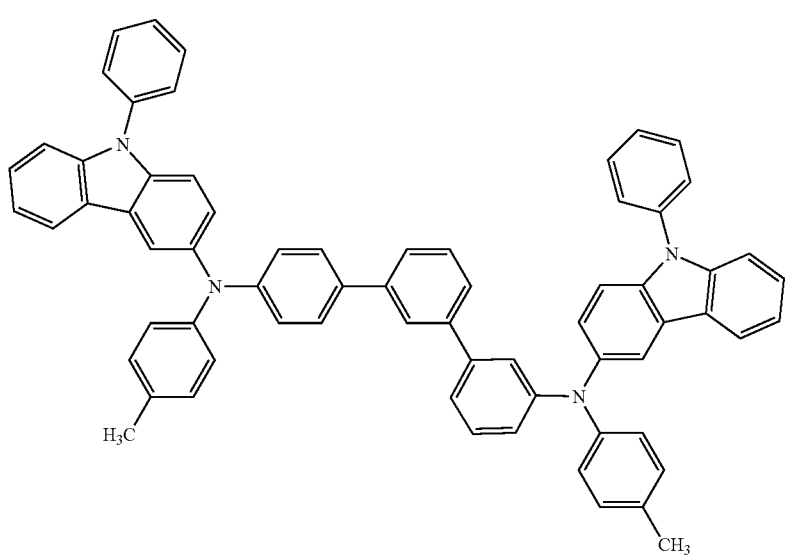

83
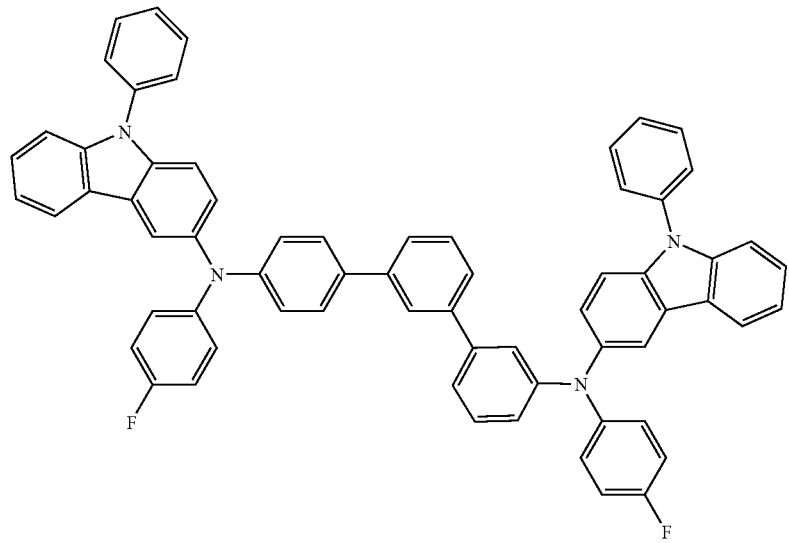
84
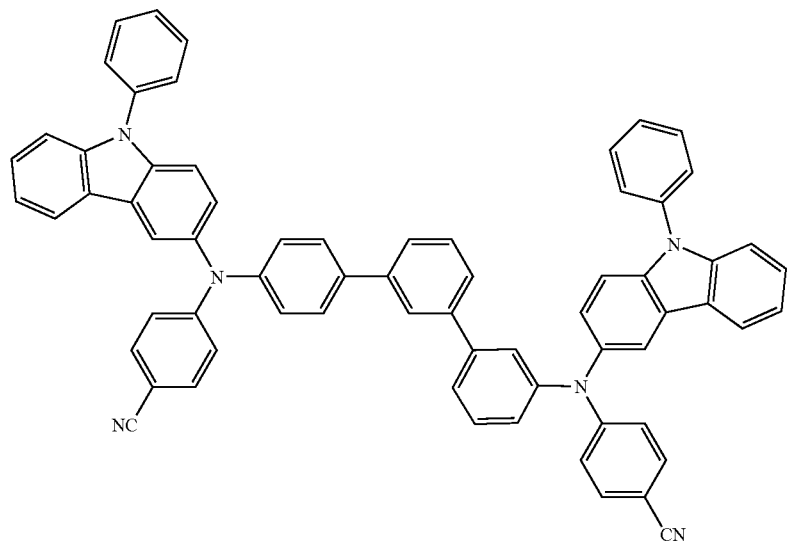
85
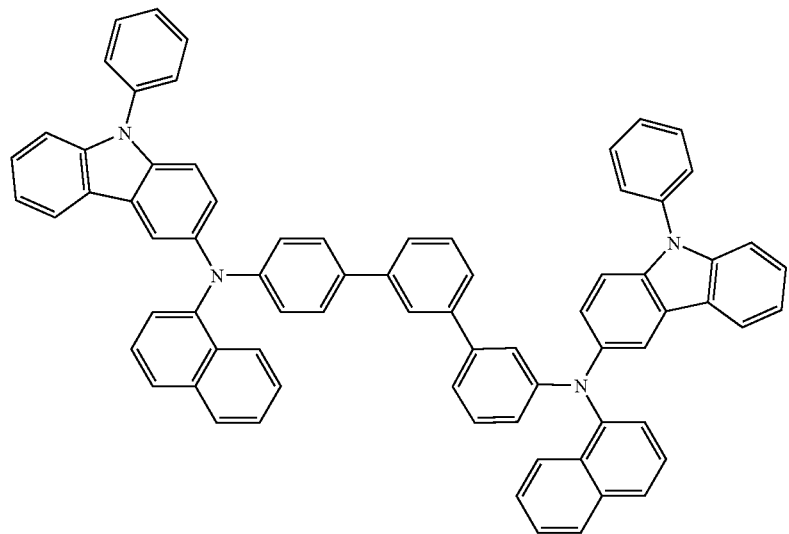

86
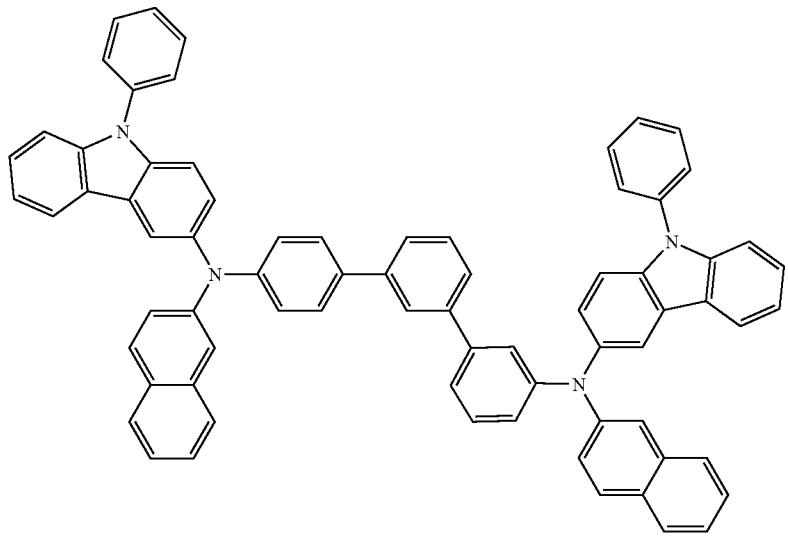
87
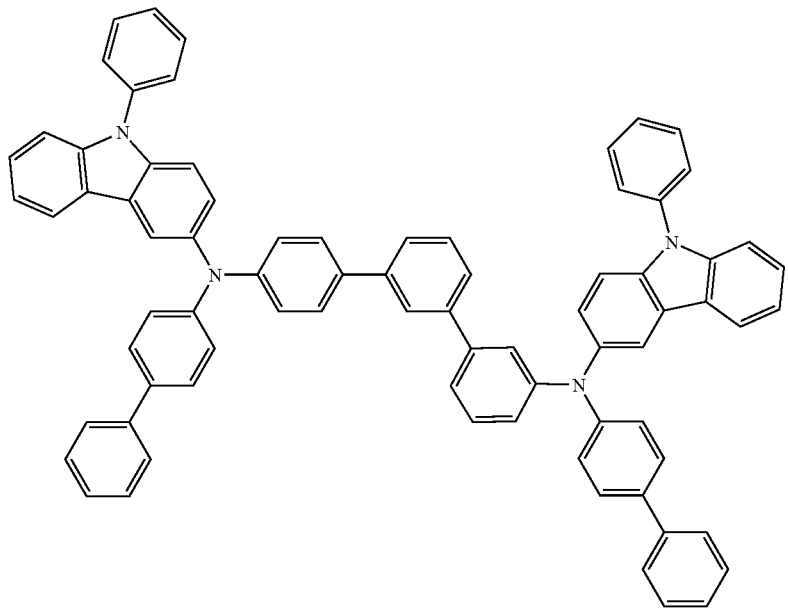
88
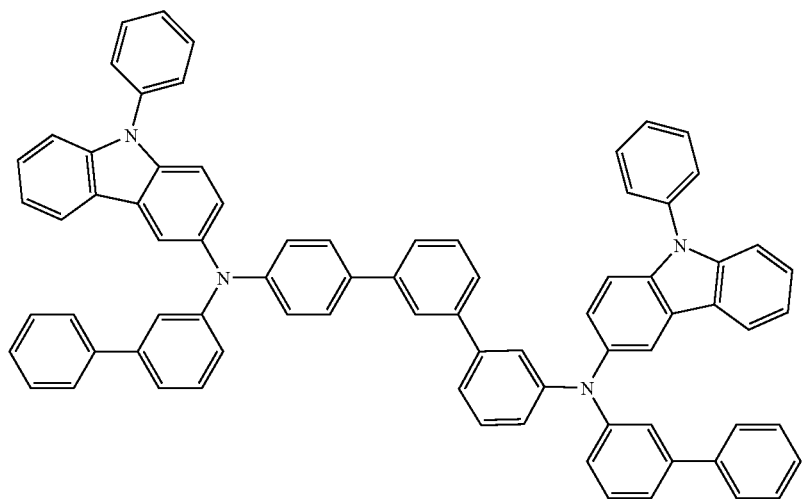

89
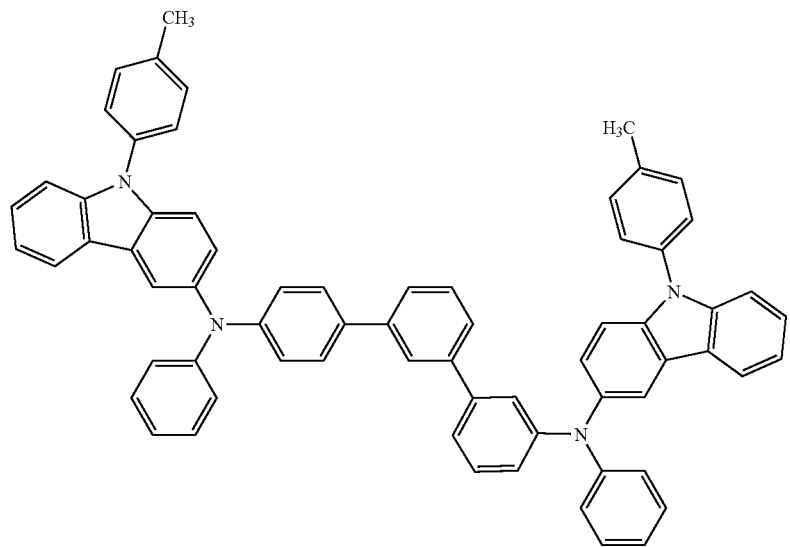
90
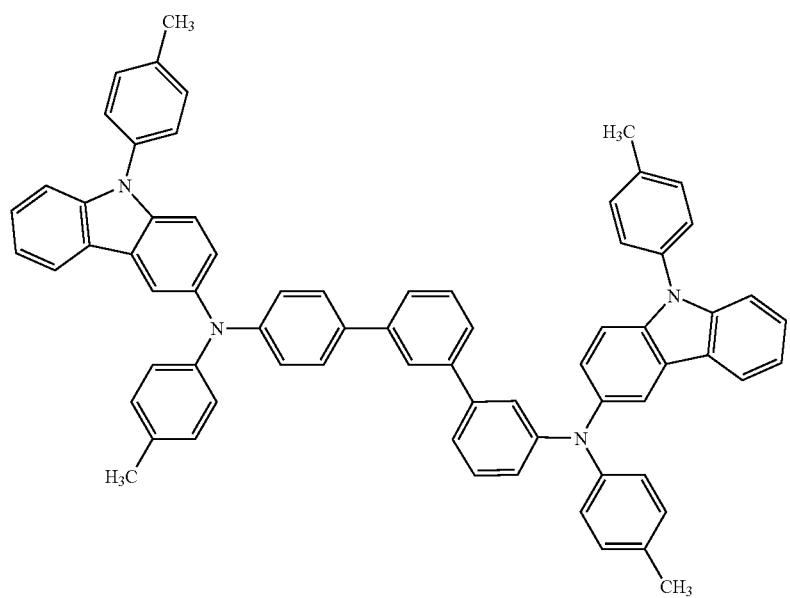

91
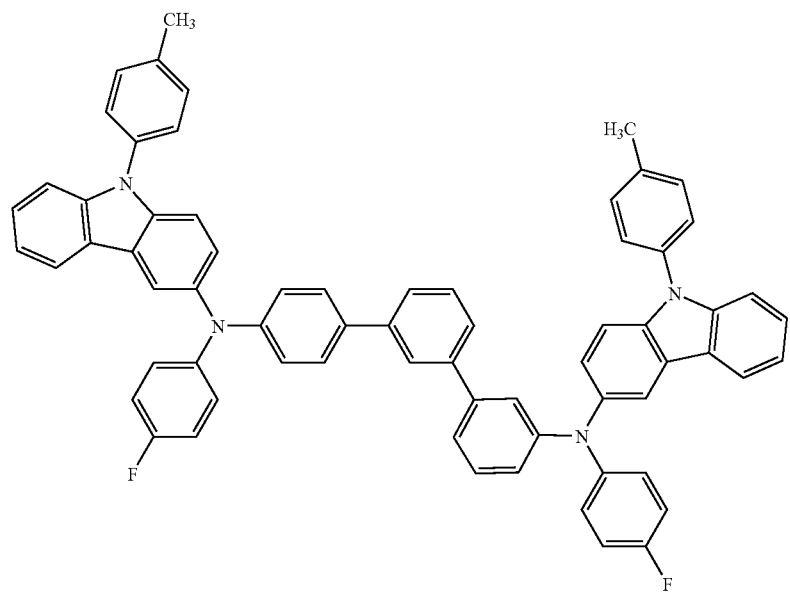
92
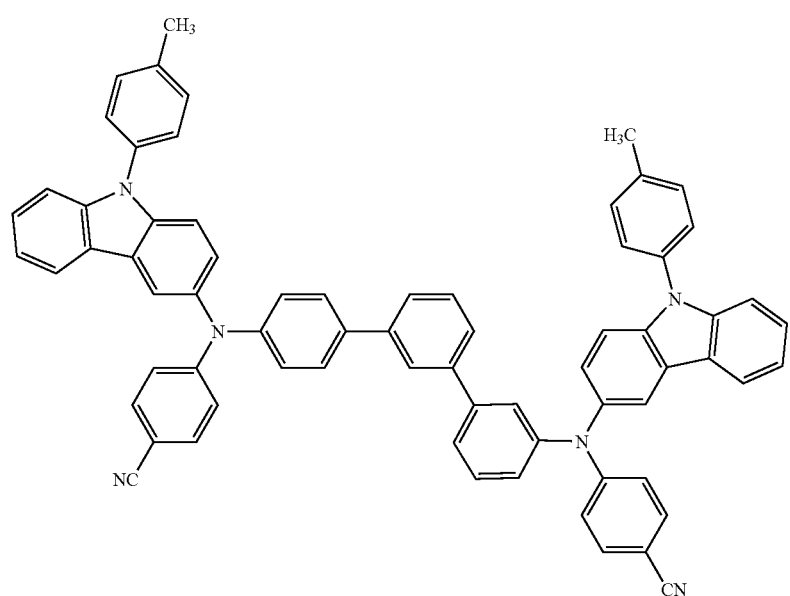

93
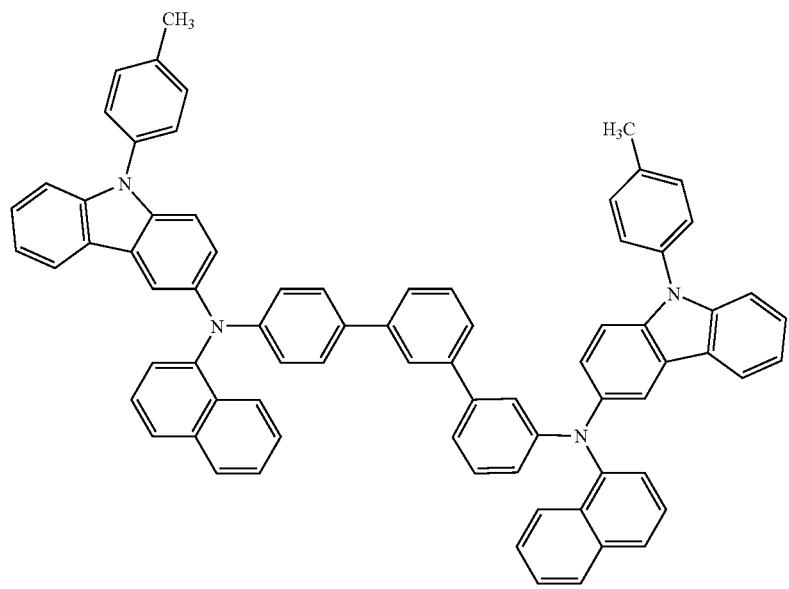
94
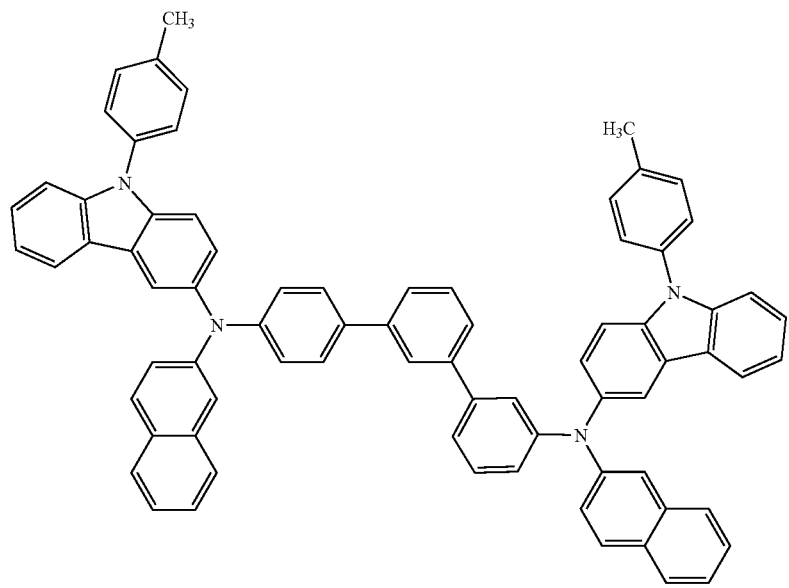

95
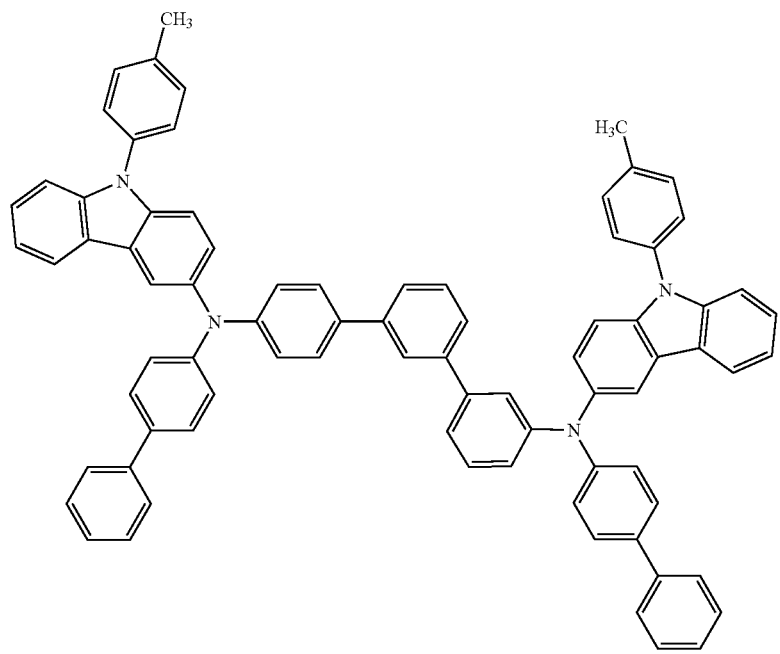
96
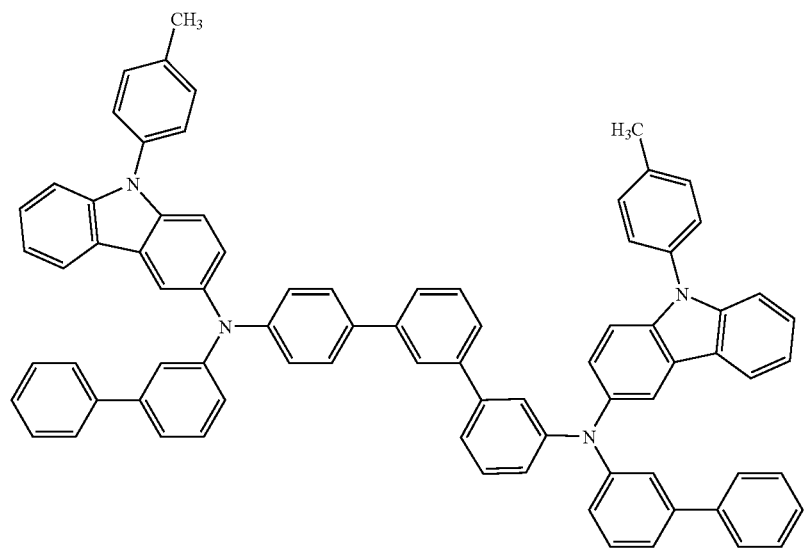

97
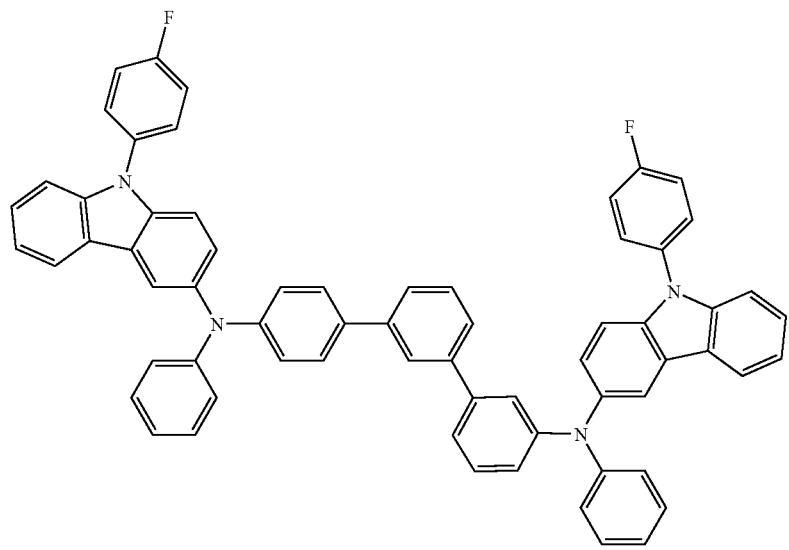
98
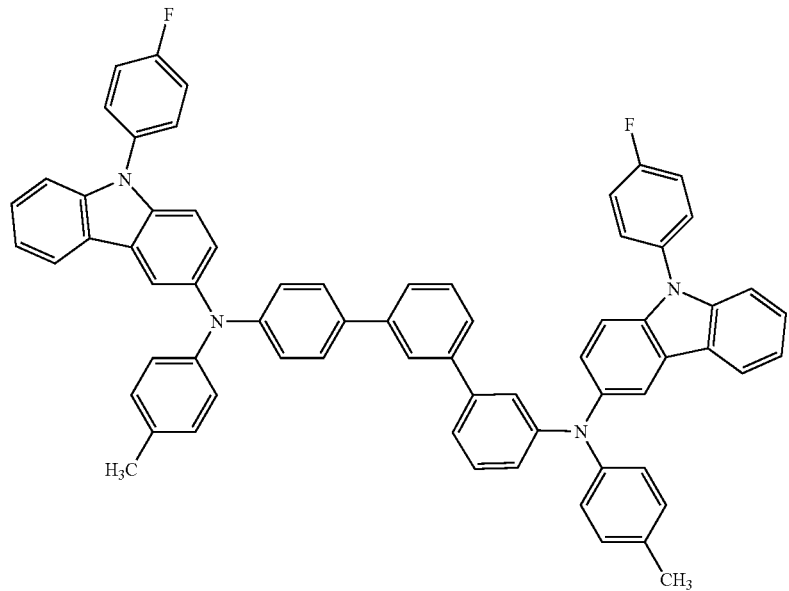

99
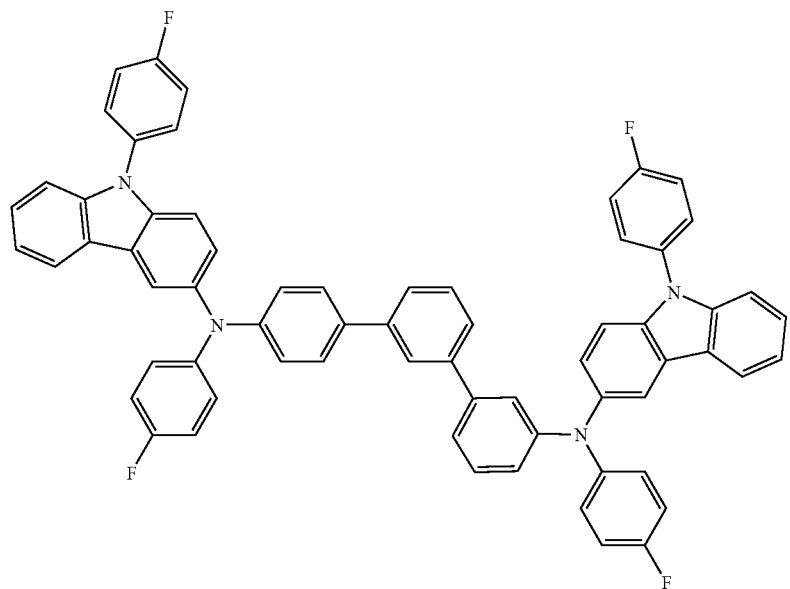
100
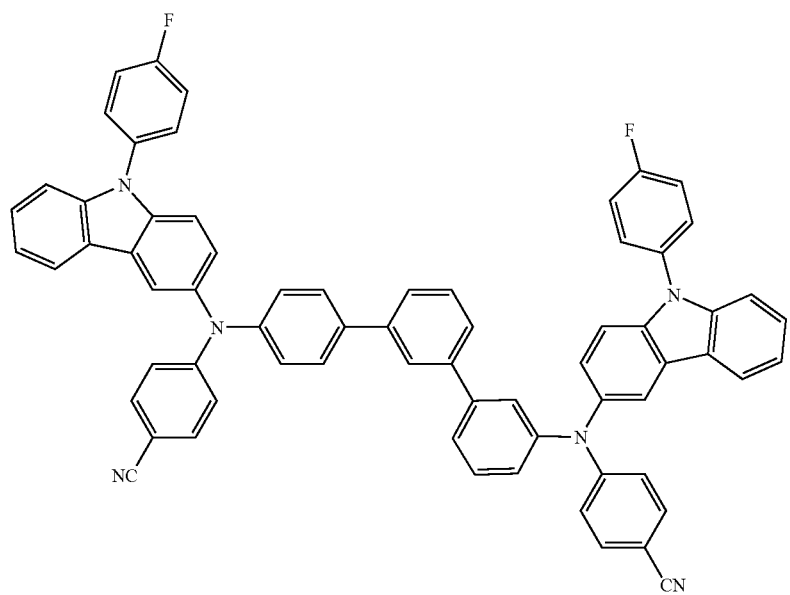

-continued
101
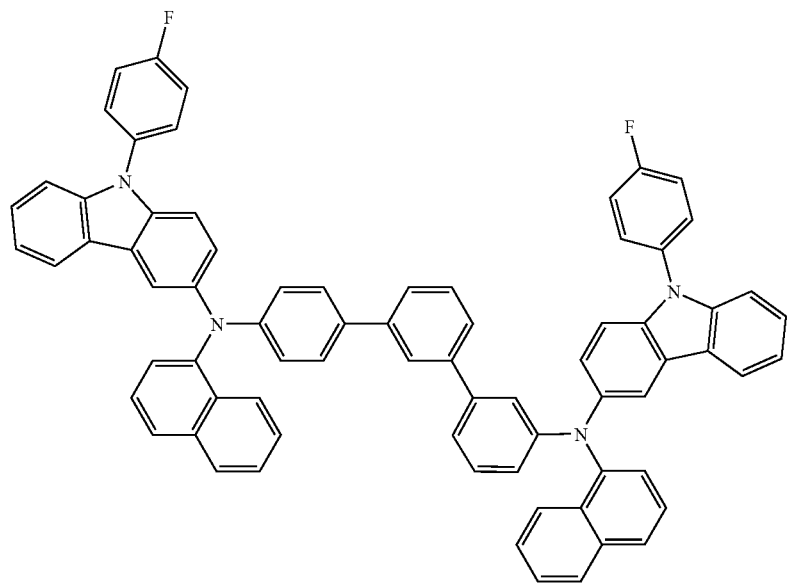
102
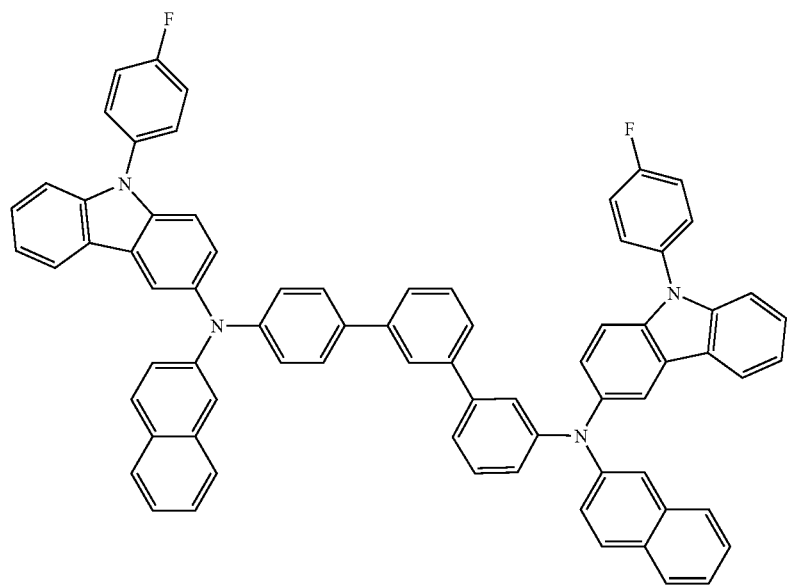

103
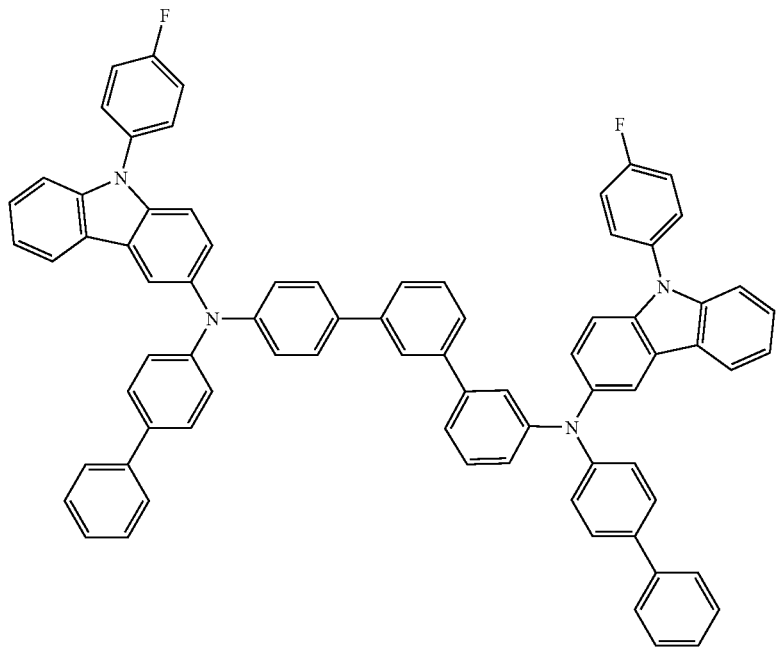
104
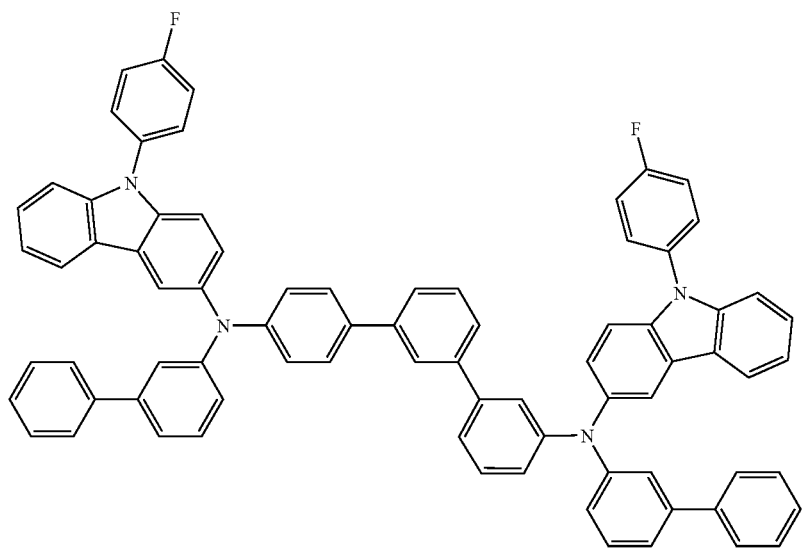
105
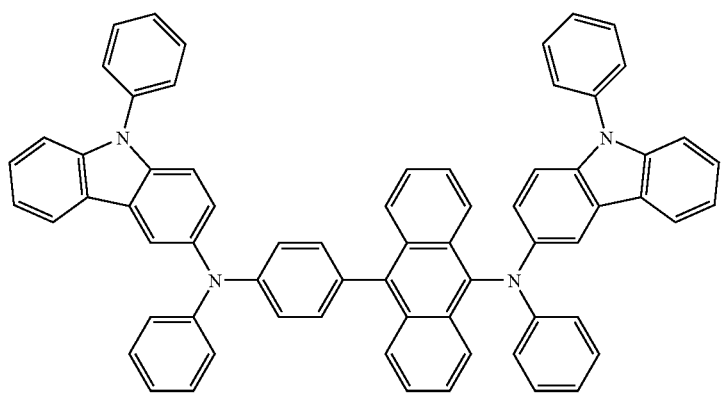

106
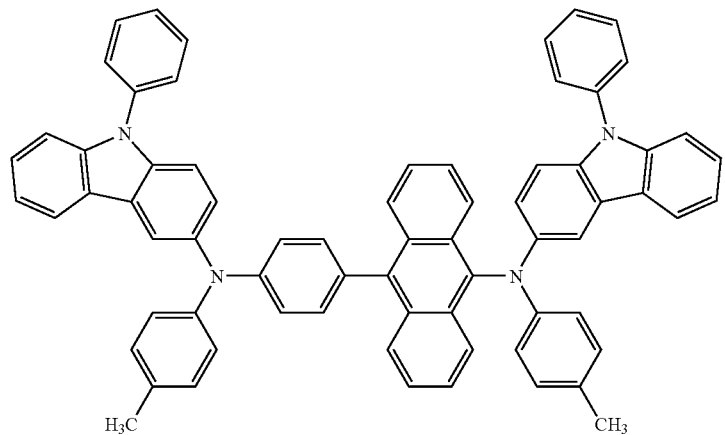
107
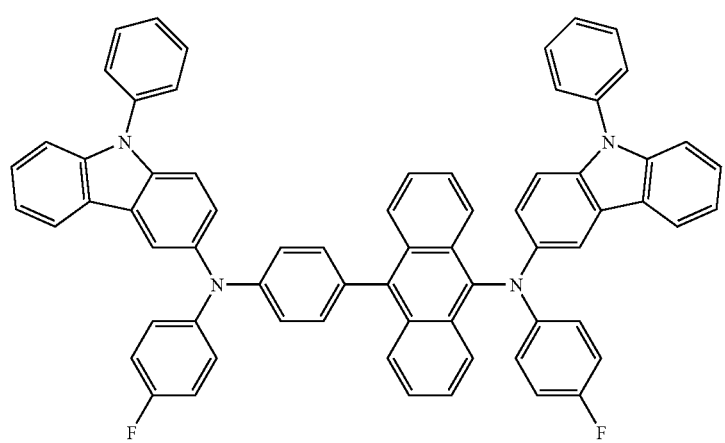
108
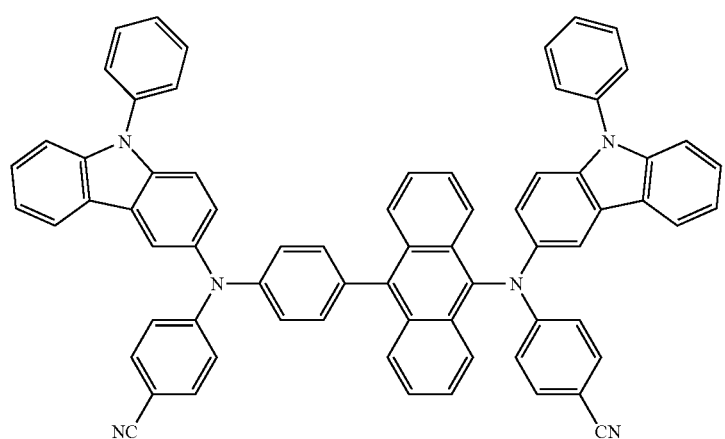

109
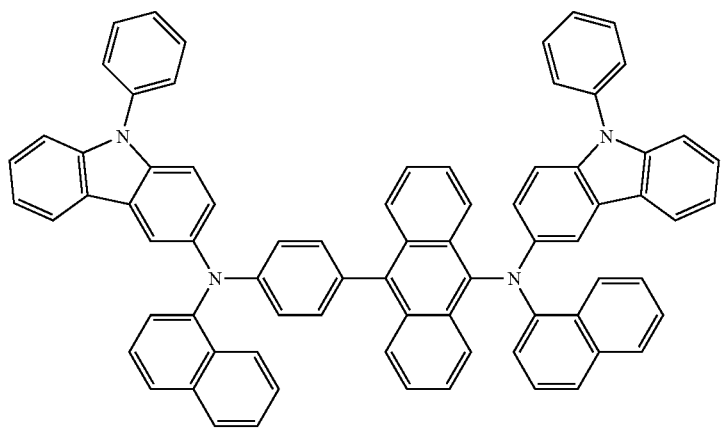
110
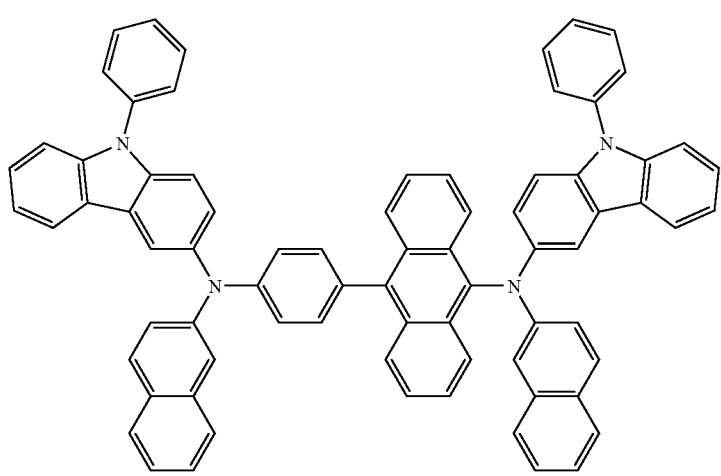
111
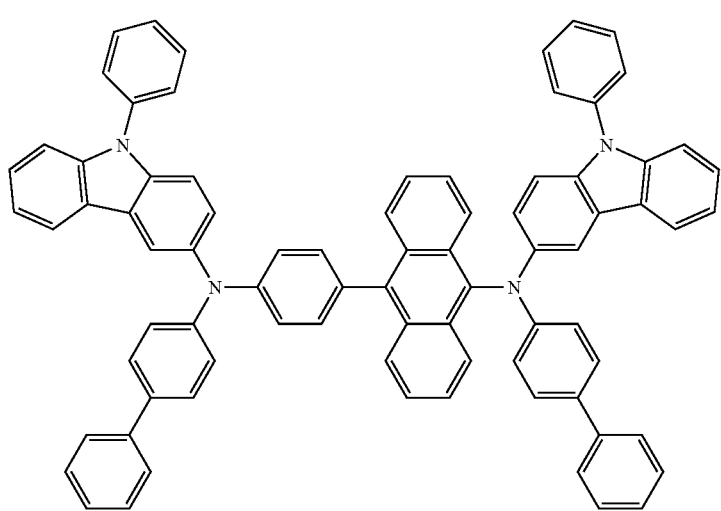

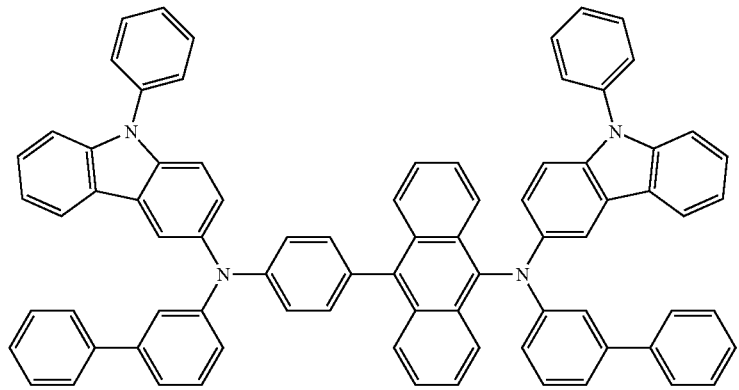
112
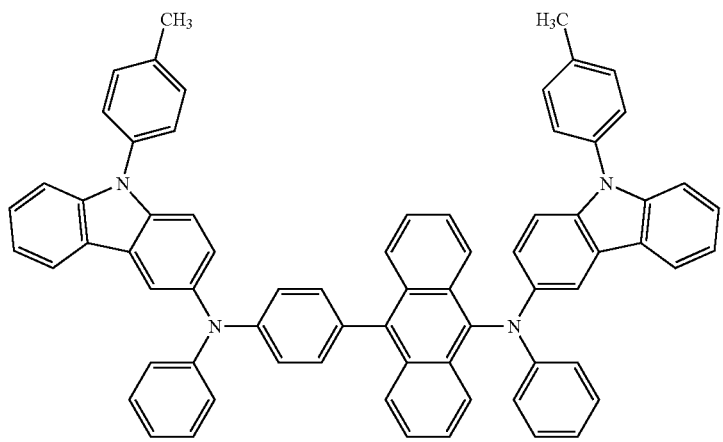
113
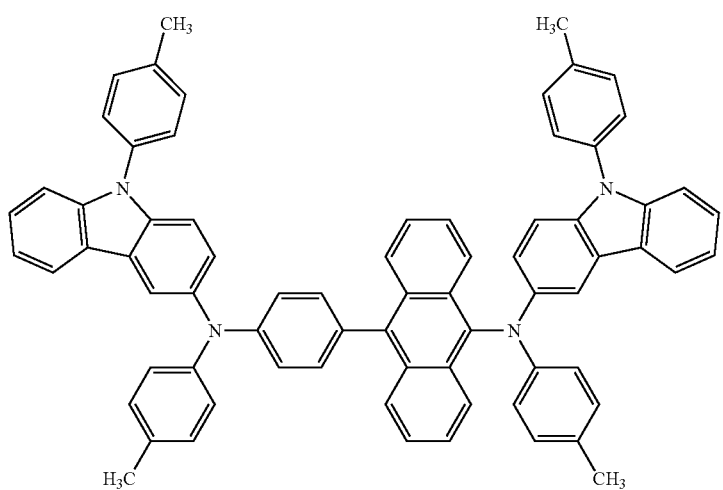
114

-continued
115
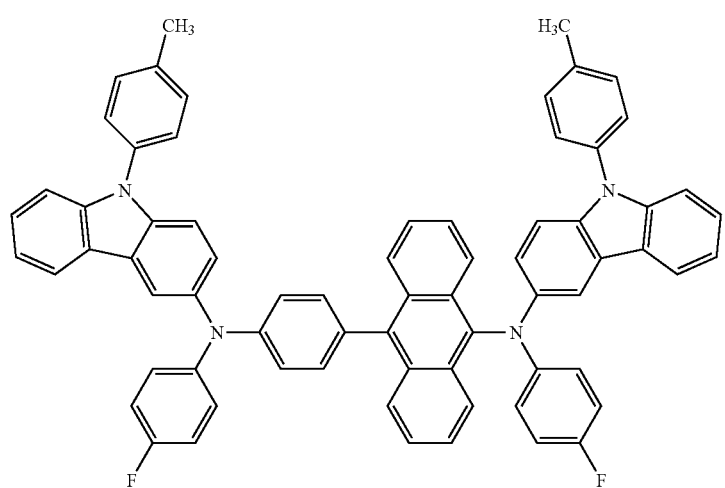
116
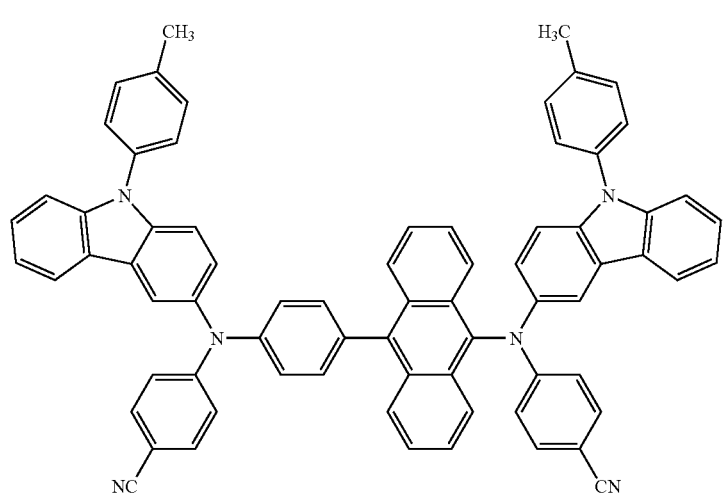
117
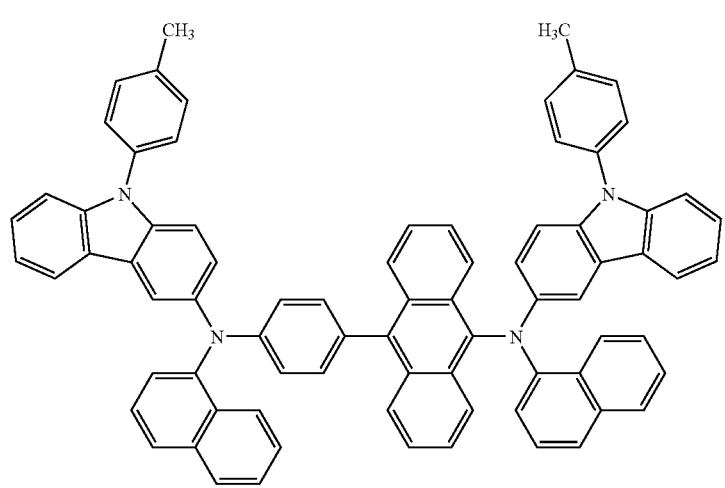

-continued
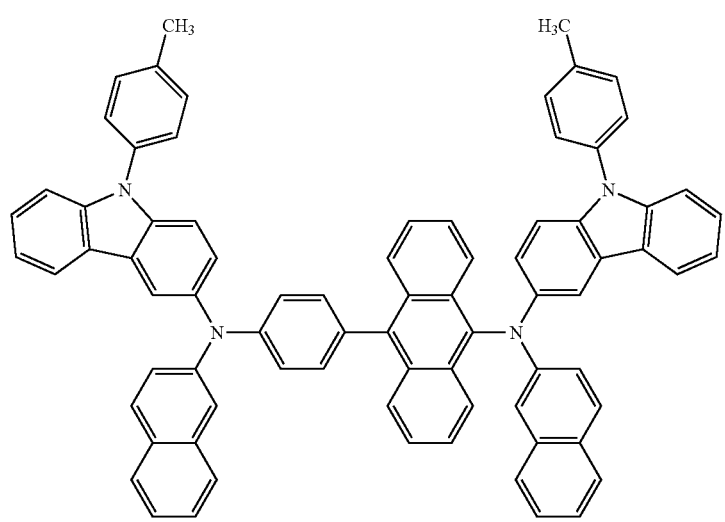
118
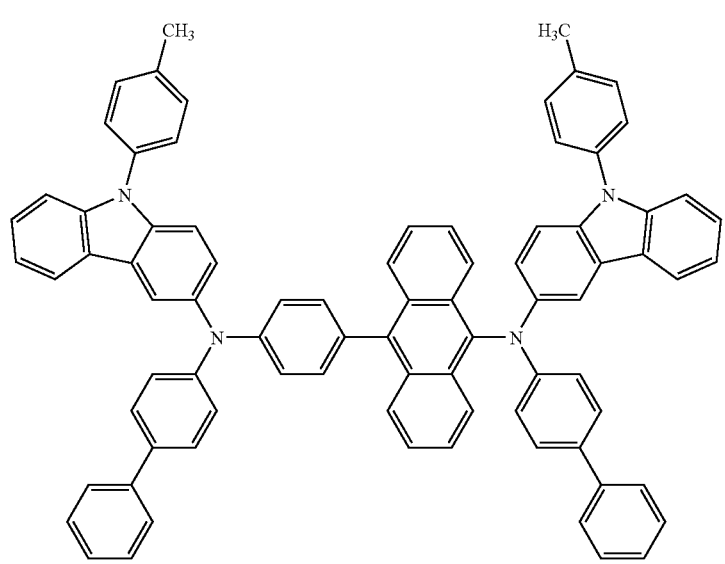
119
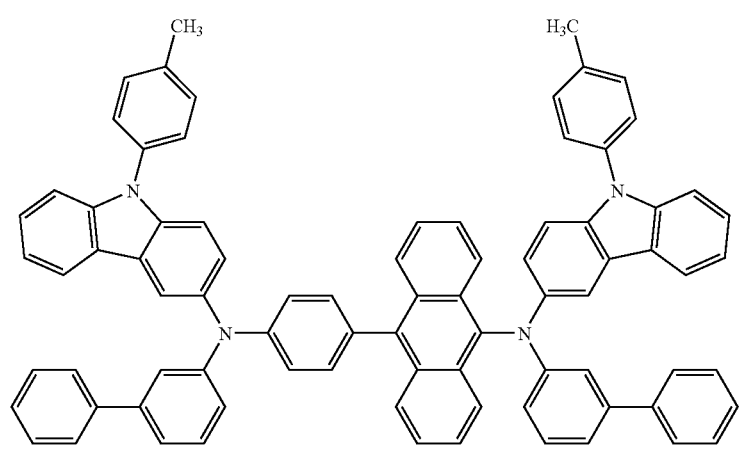
120

121
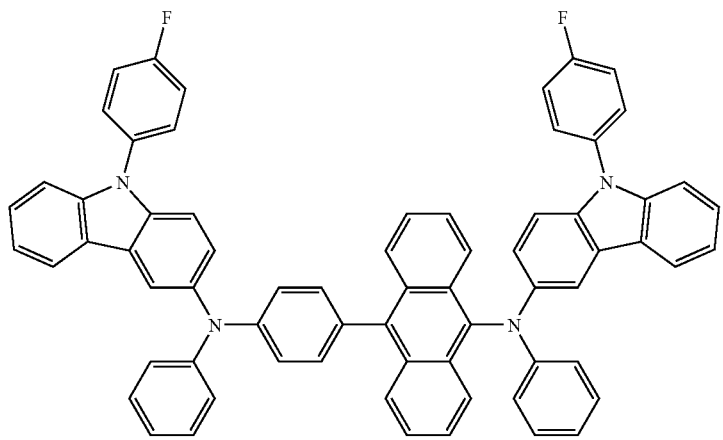
122
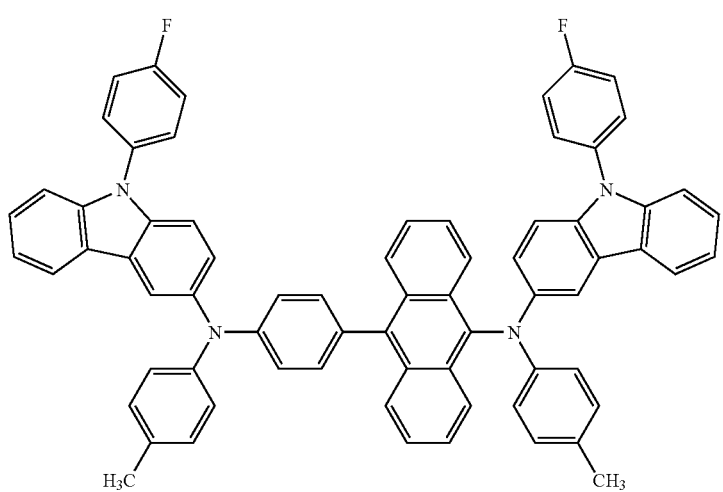
123
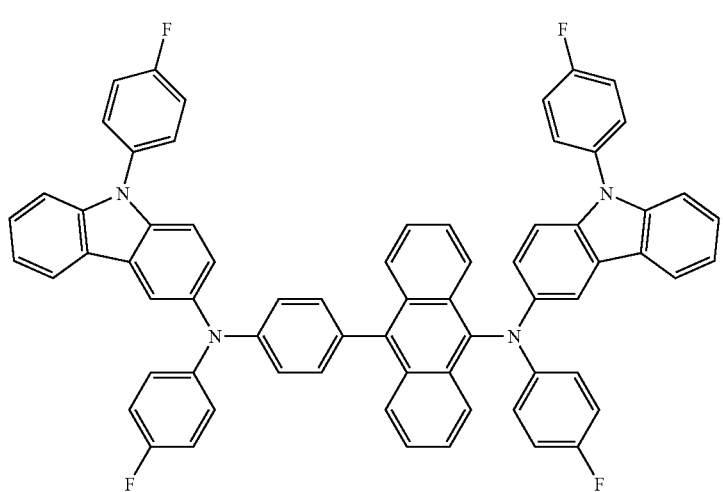

124
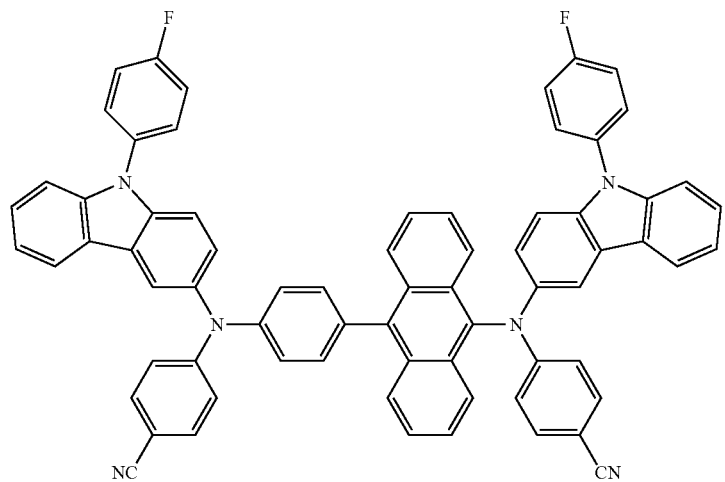
125
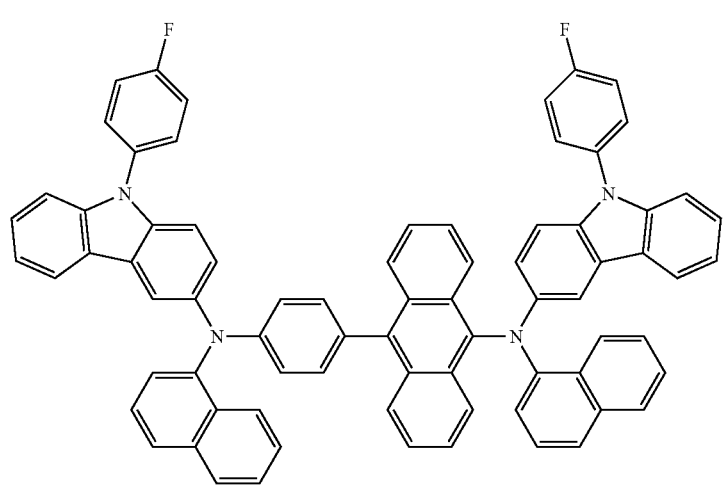
126
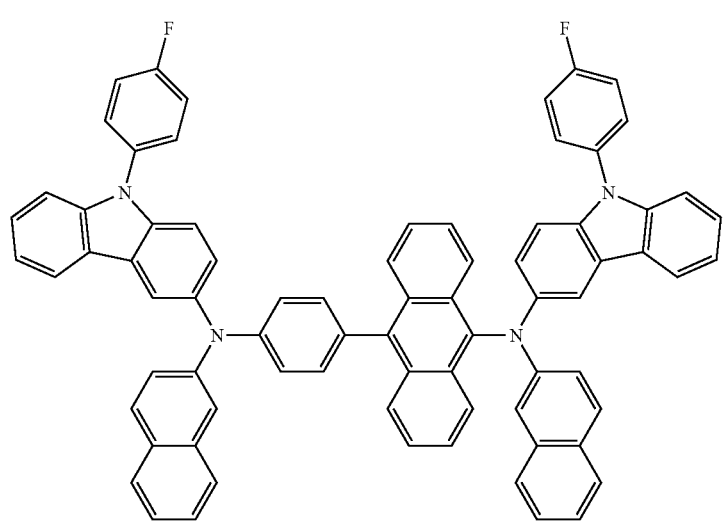

127
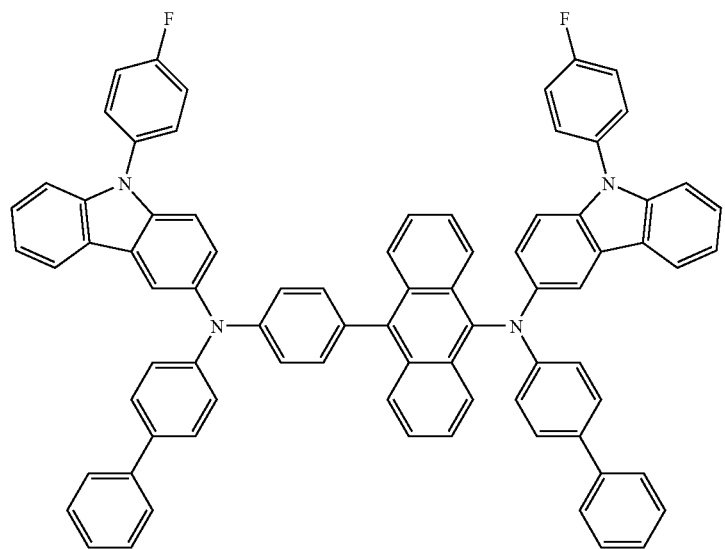
128
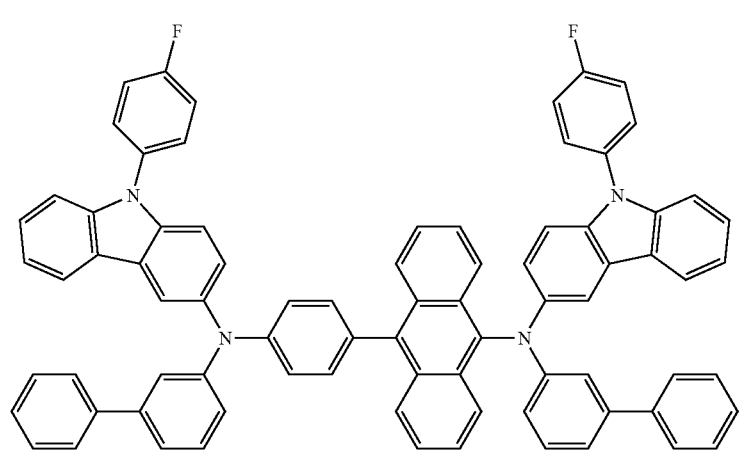
129
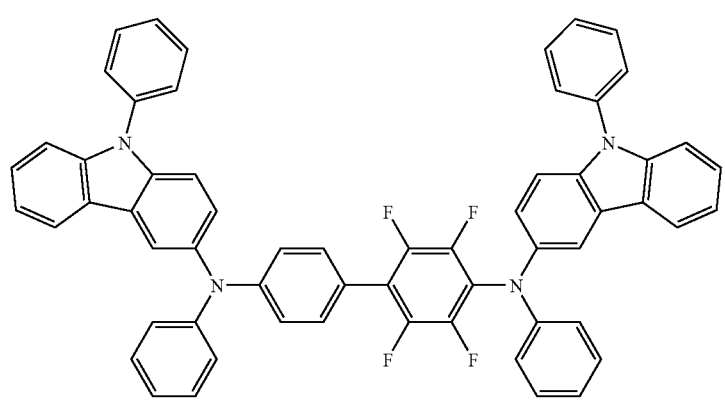

130
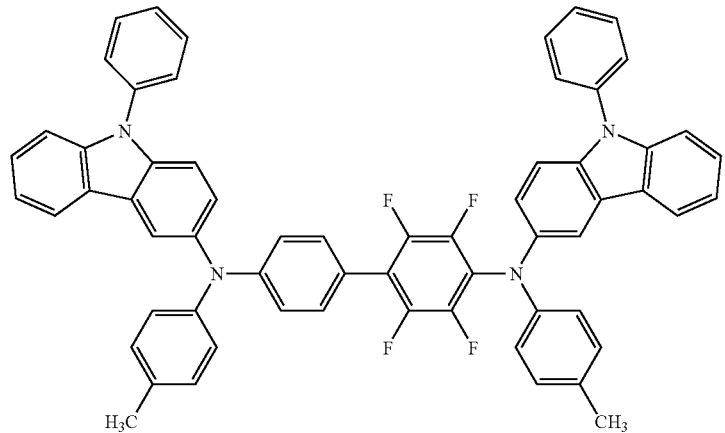
131
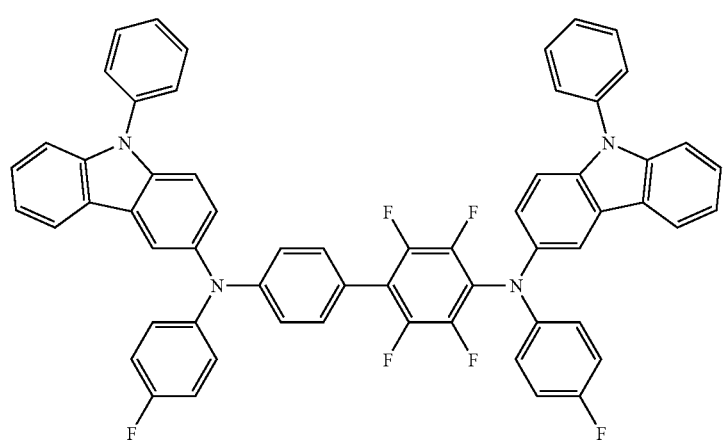
132
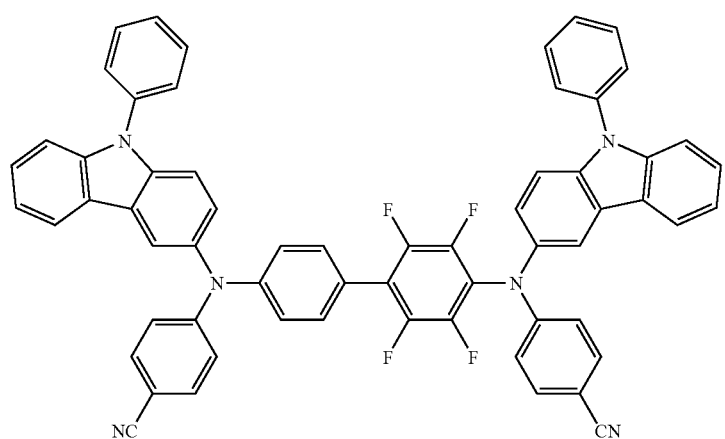

133
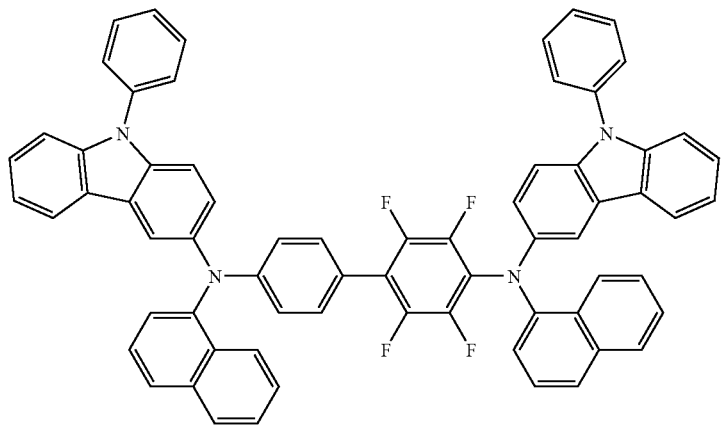
134
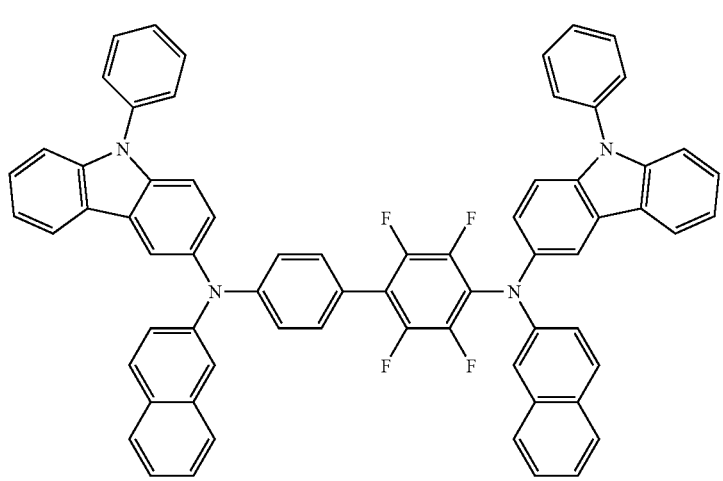
135
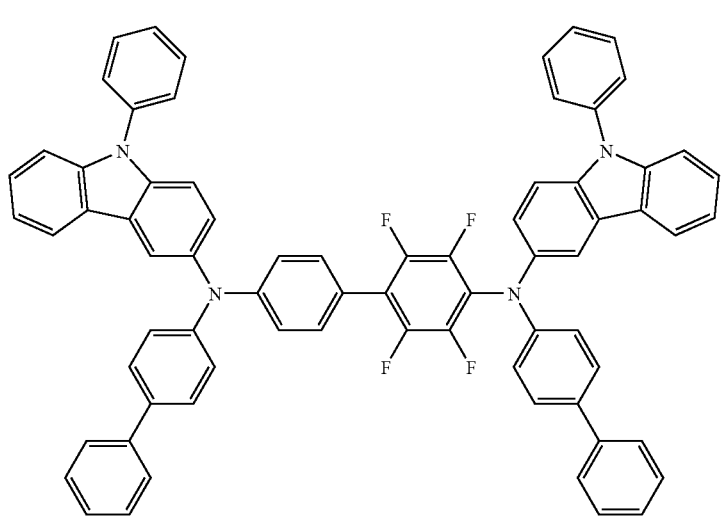

136
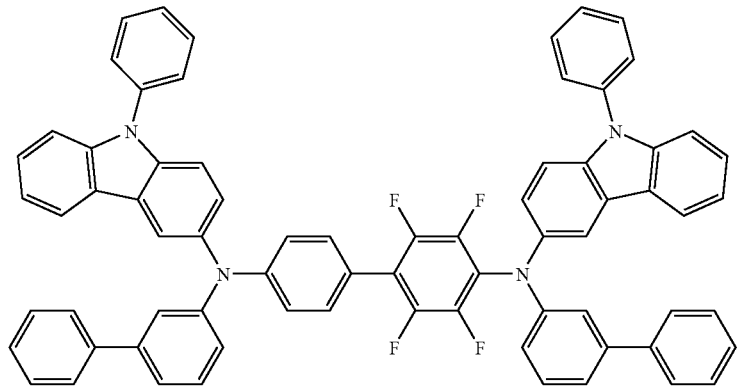
137
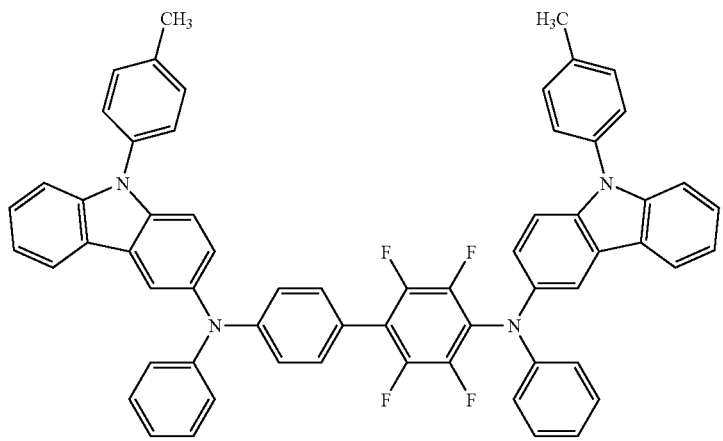
138
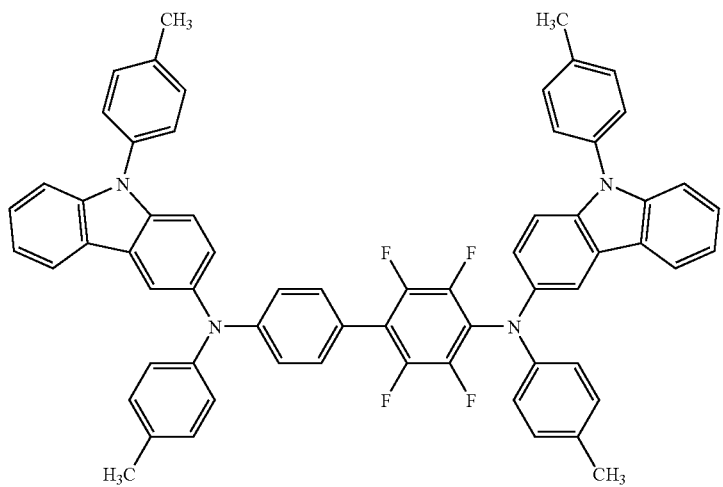

139
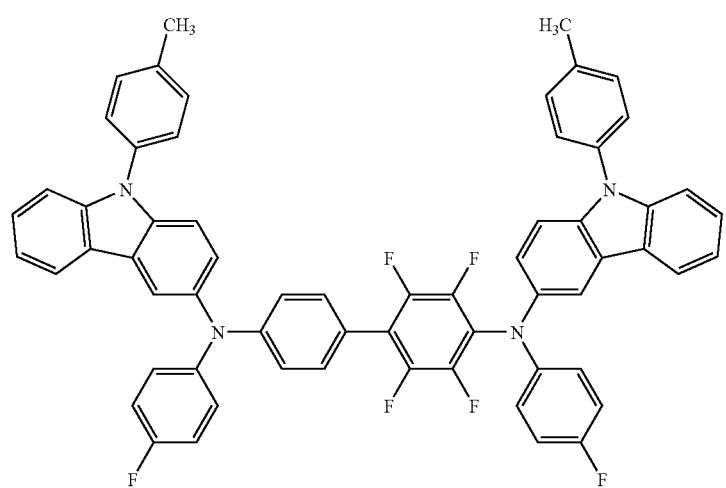
140
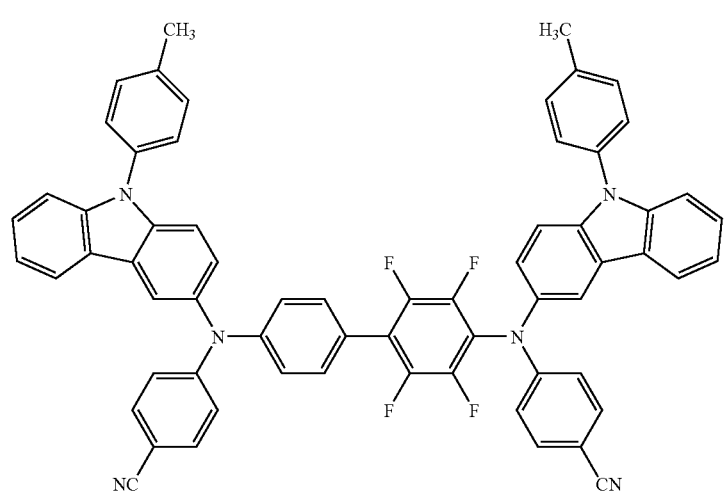
141
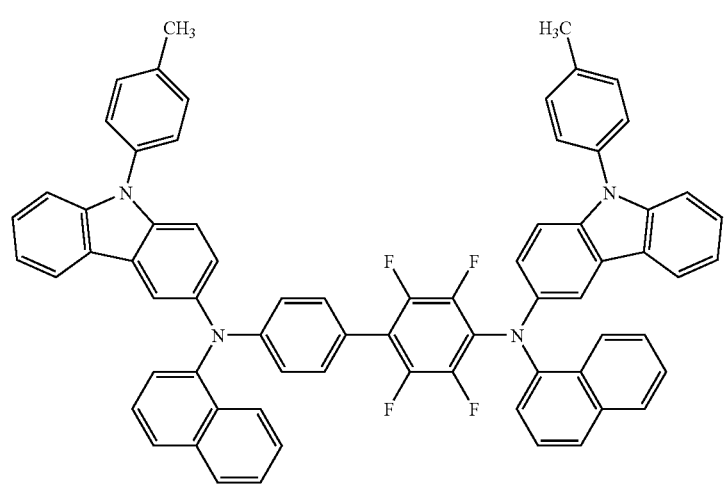

142
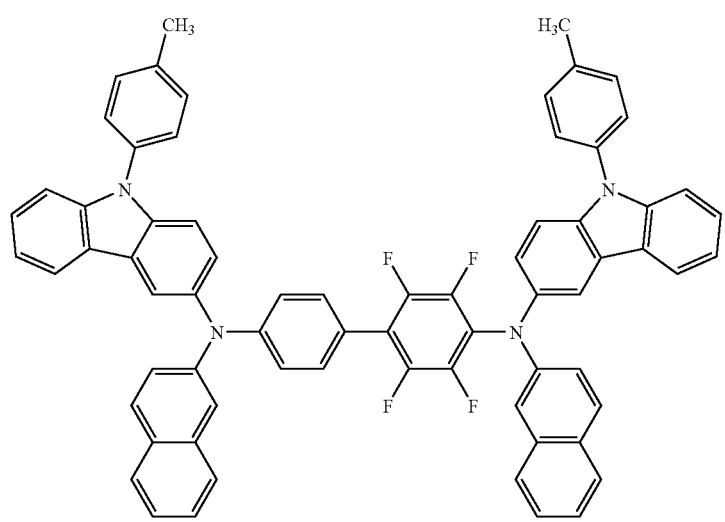
143
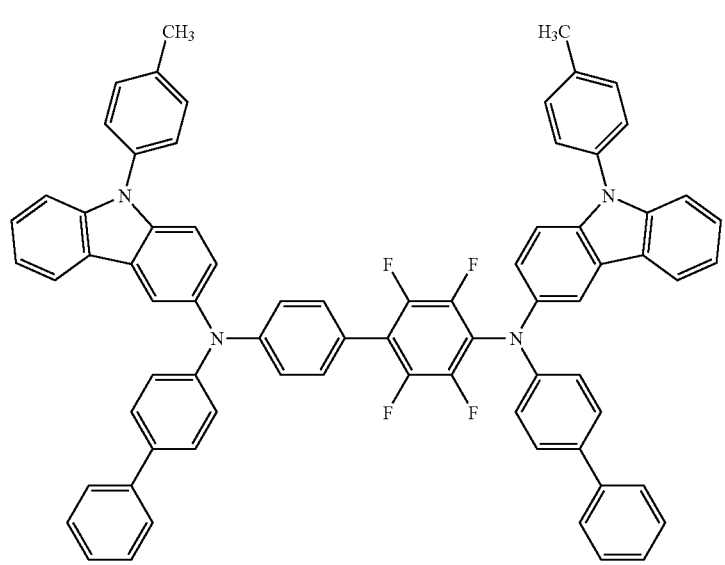
144
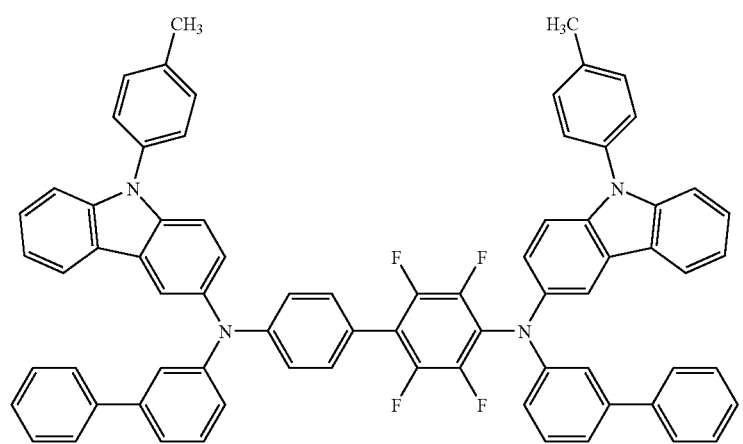

145
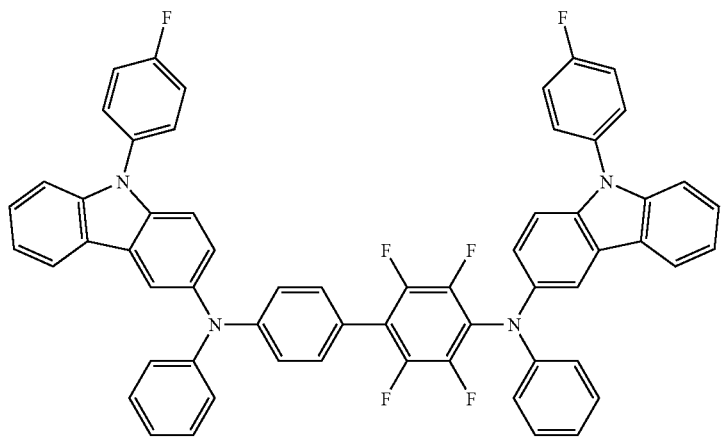
146
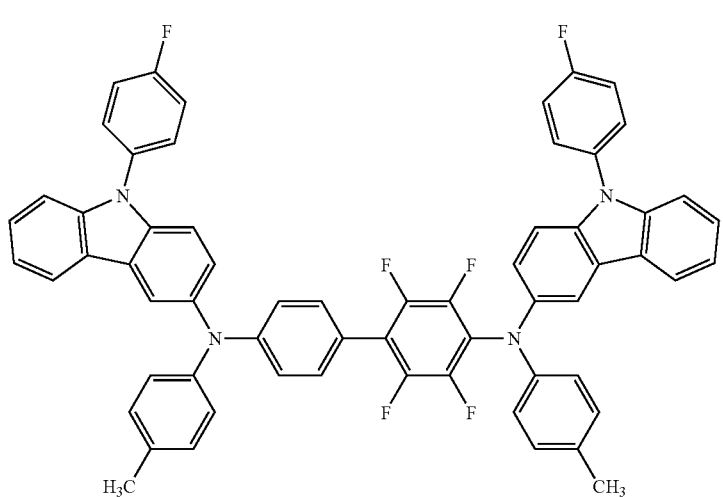
147
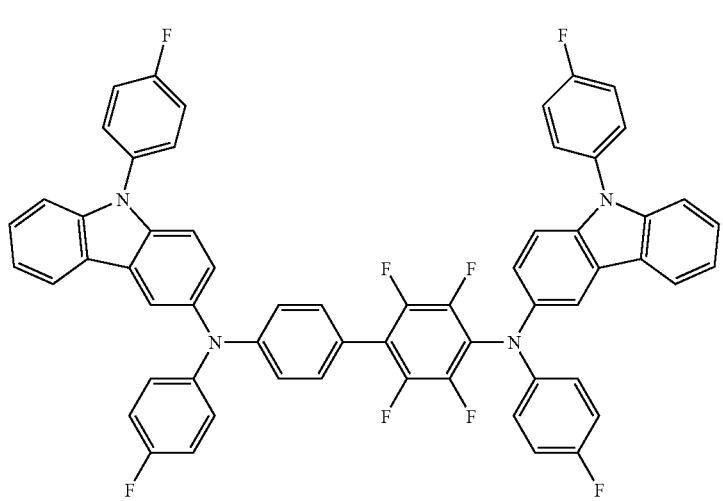

148
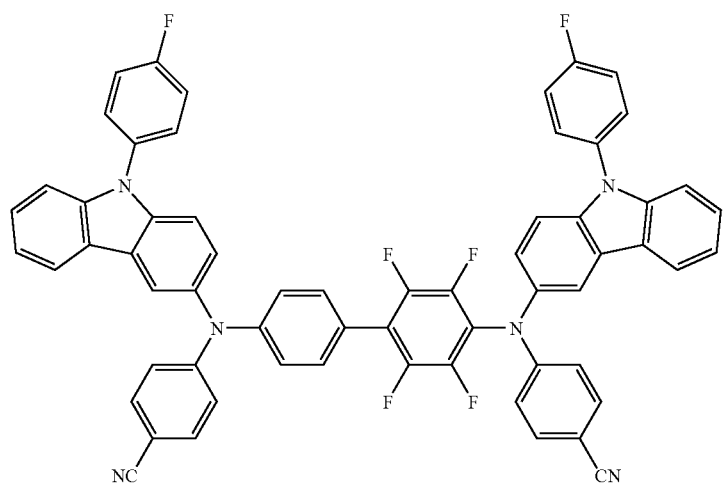
149
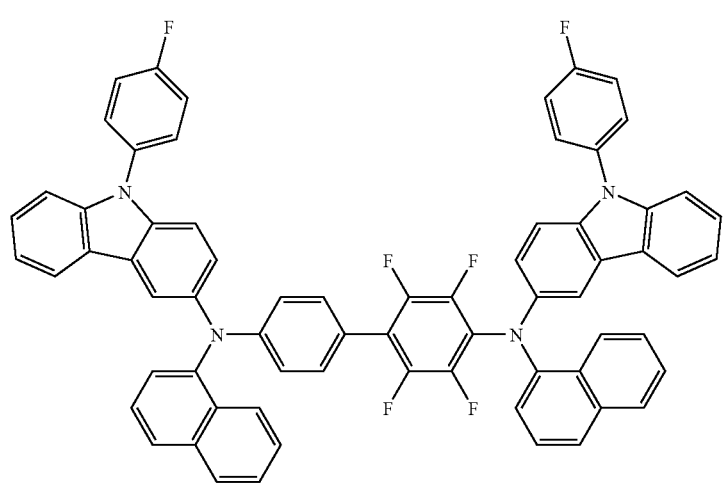
150
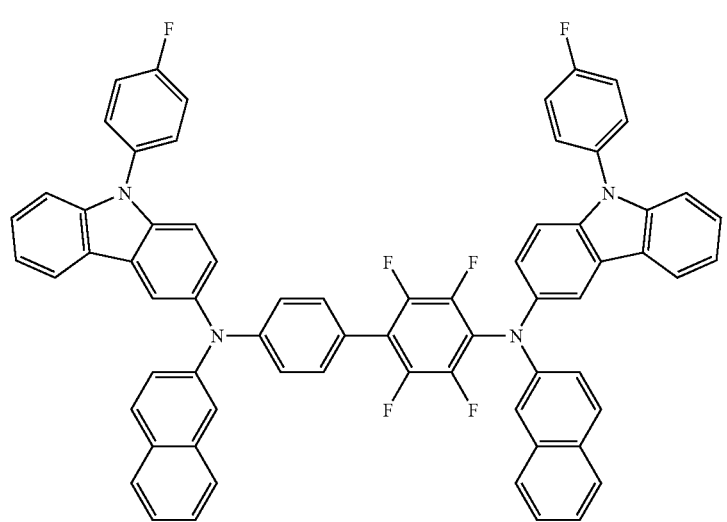

151
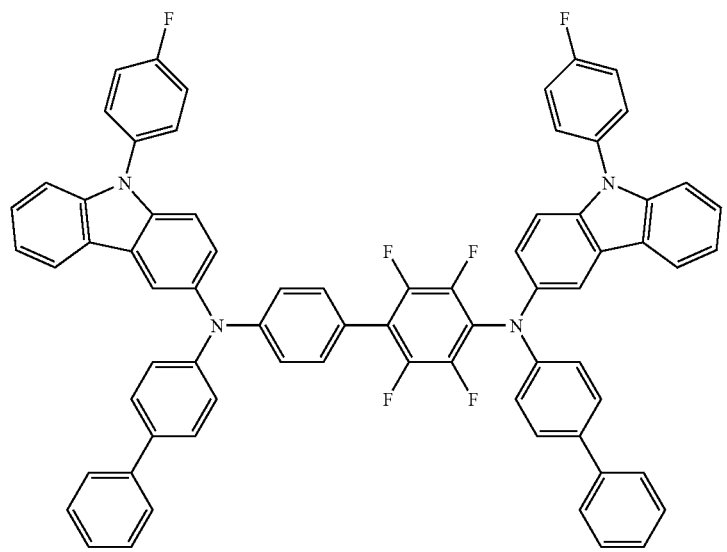
152
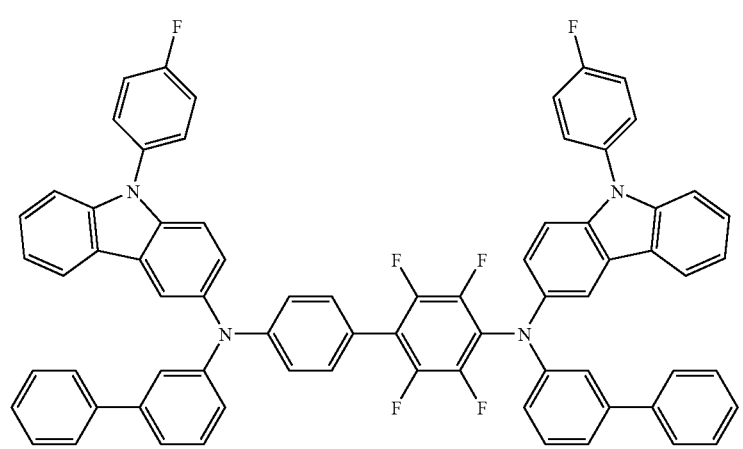
153
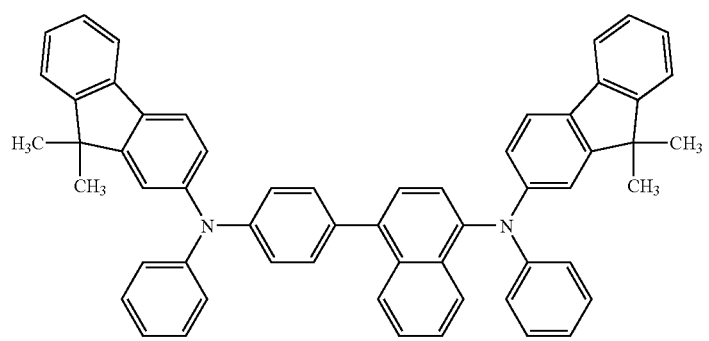

154
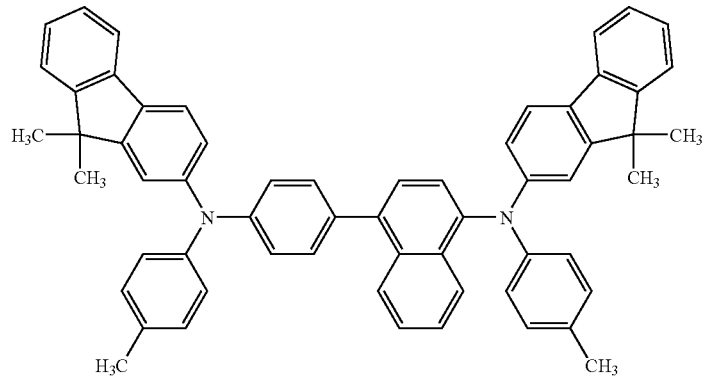
155
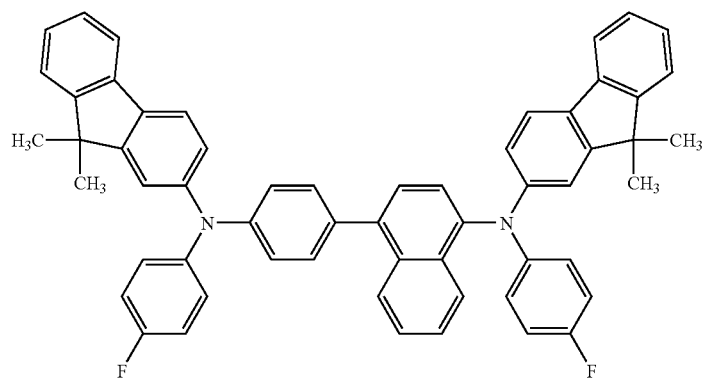
156
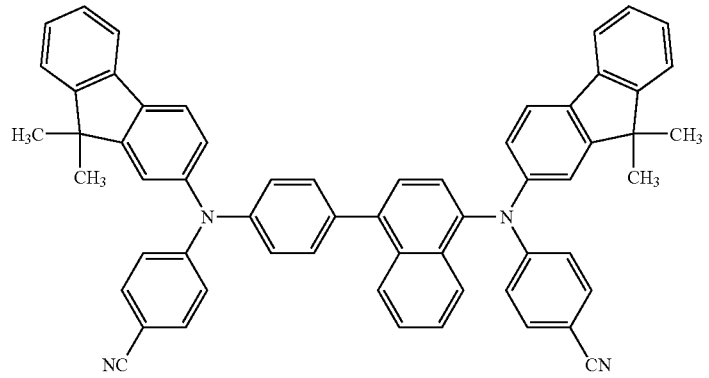
157
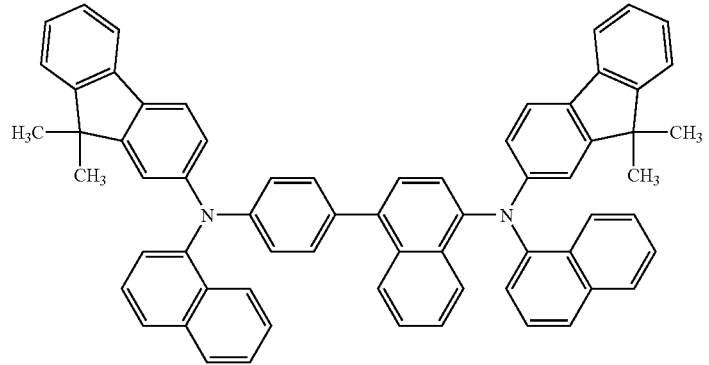

158
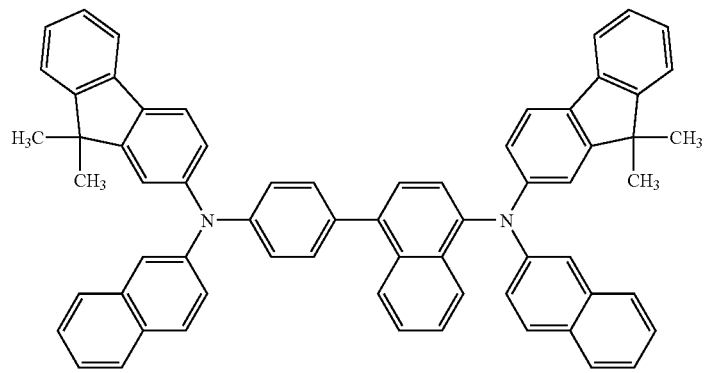
159
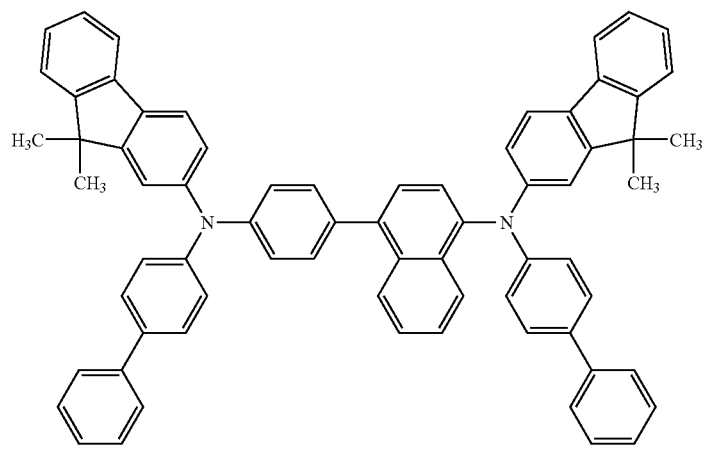
160
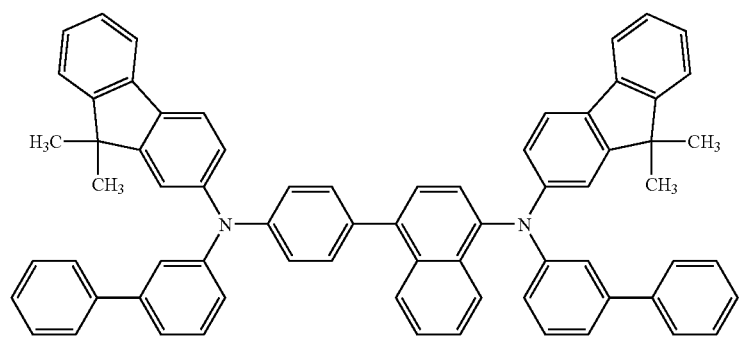
161
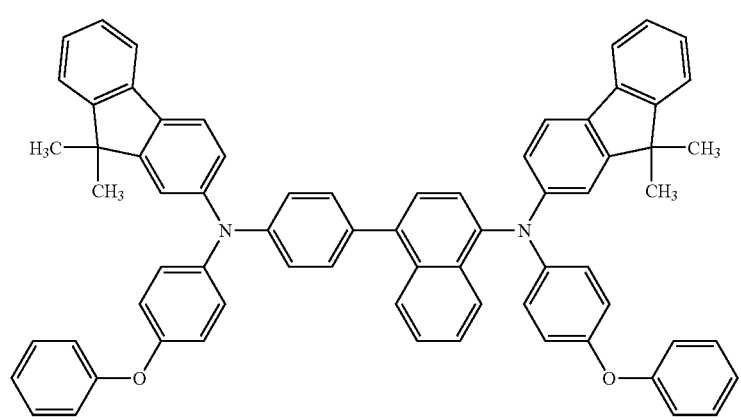

162
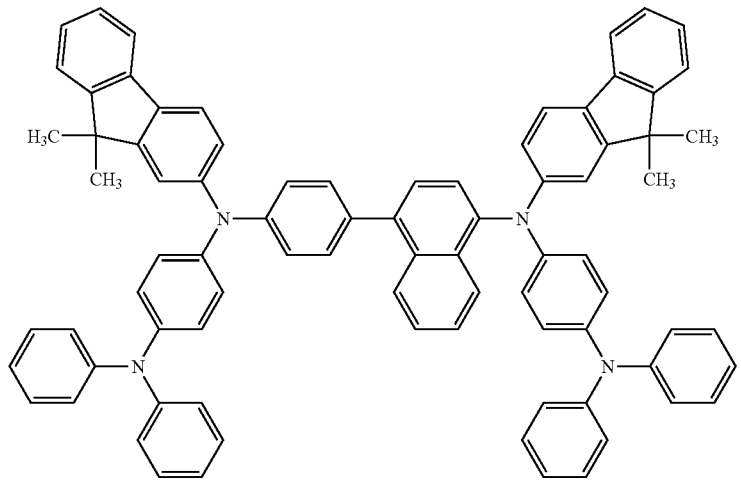
163
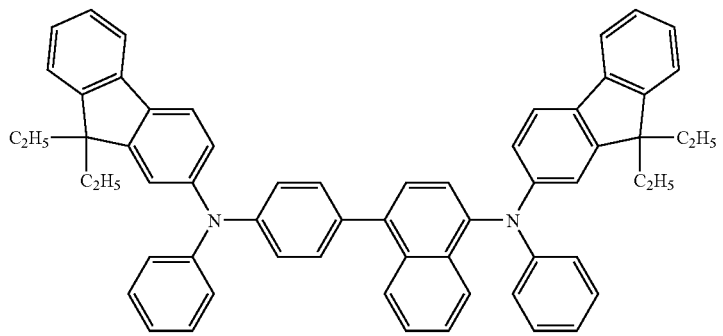
164
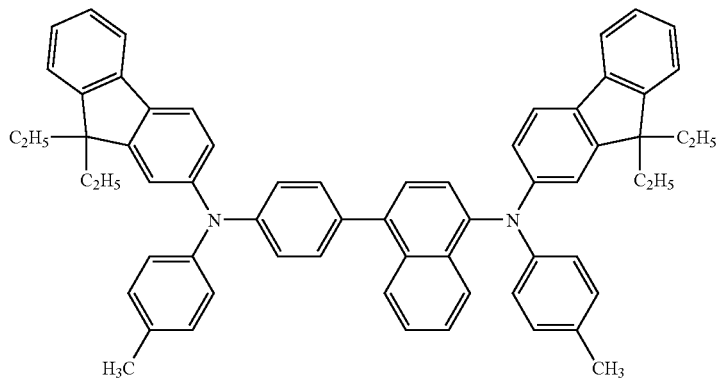
165
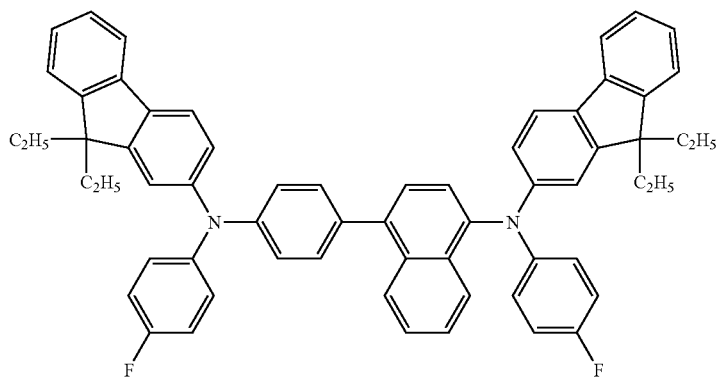

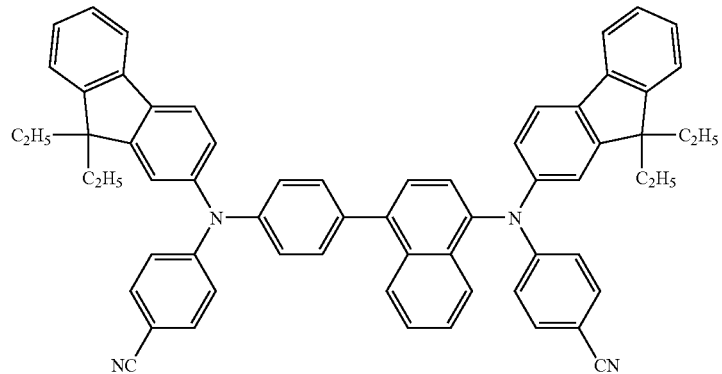
166
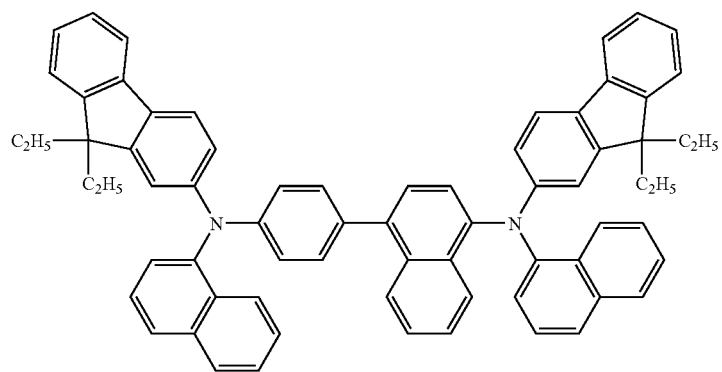
167
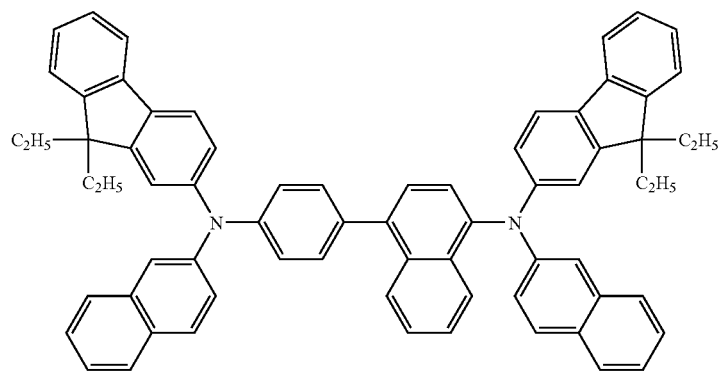
168
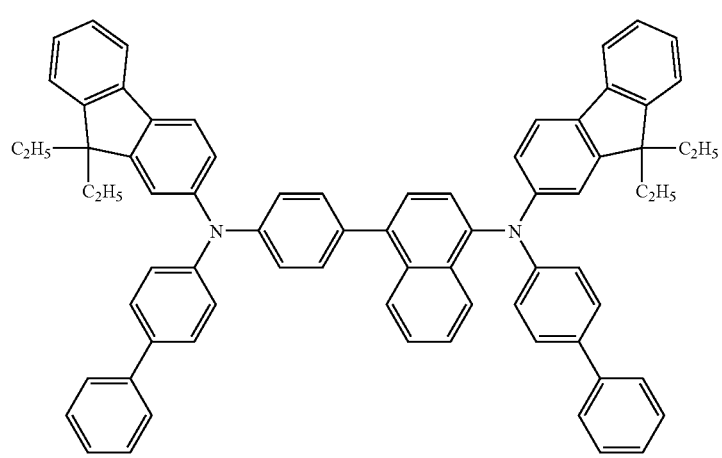
169

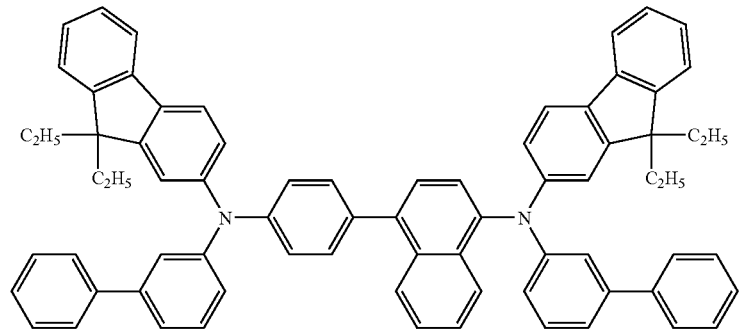
170
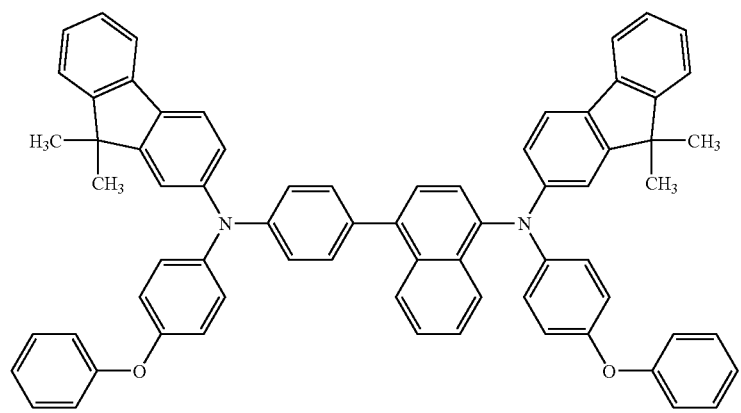
171
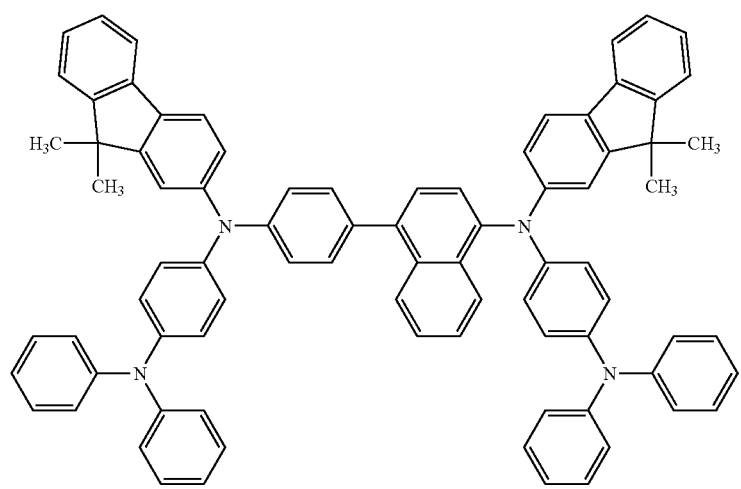
172
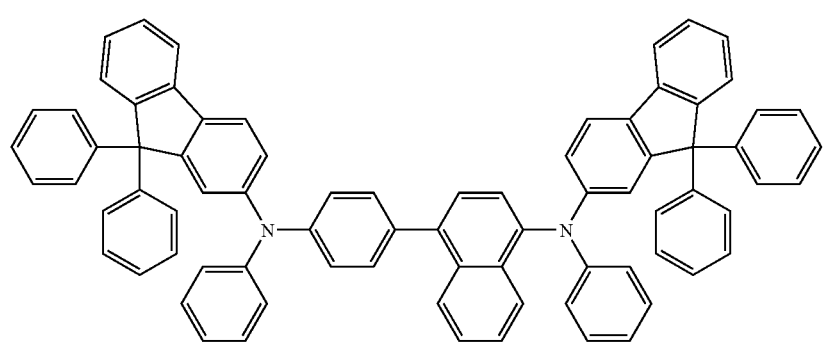
173

-continued
174
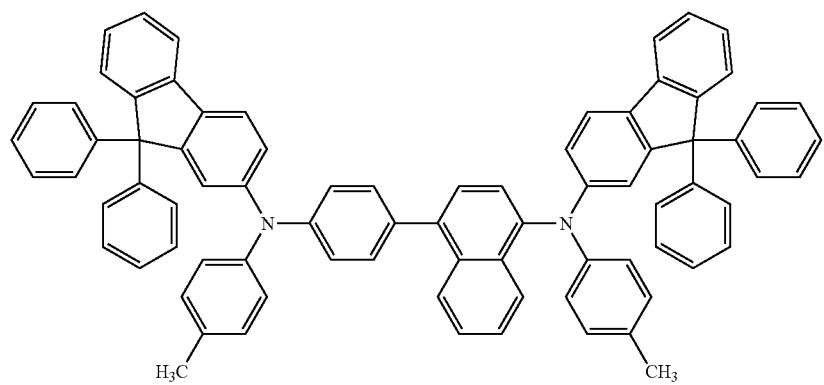
175
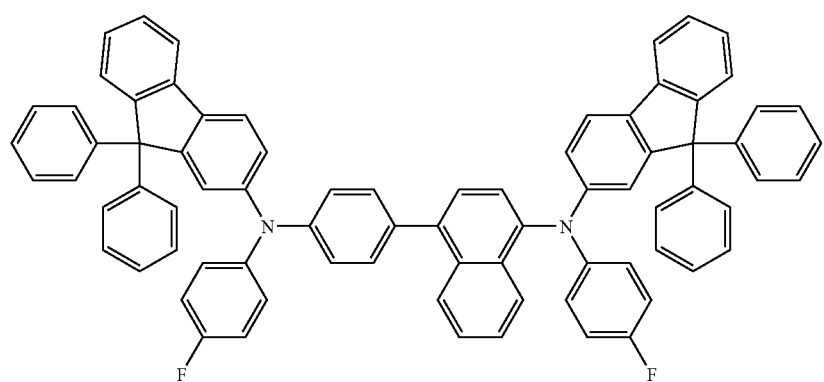
176
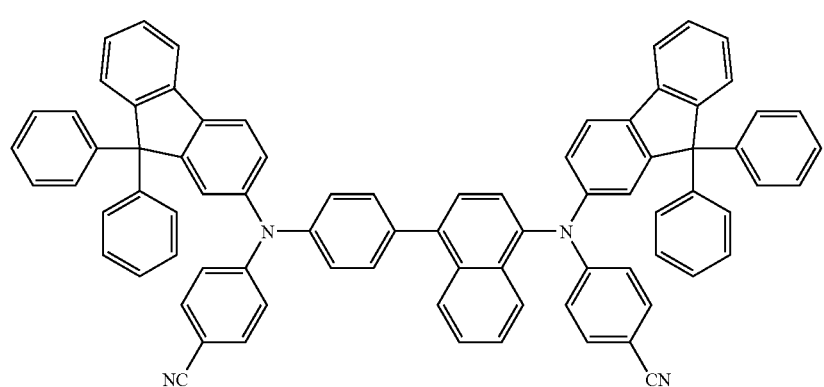
177
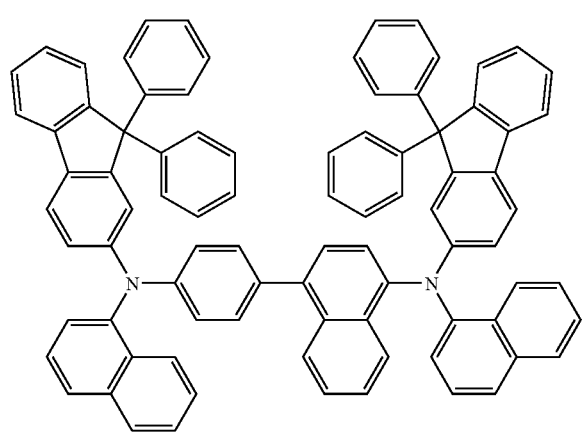

178
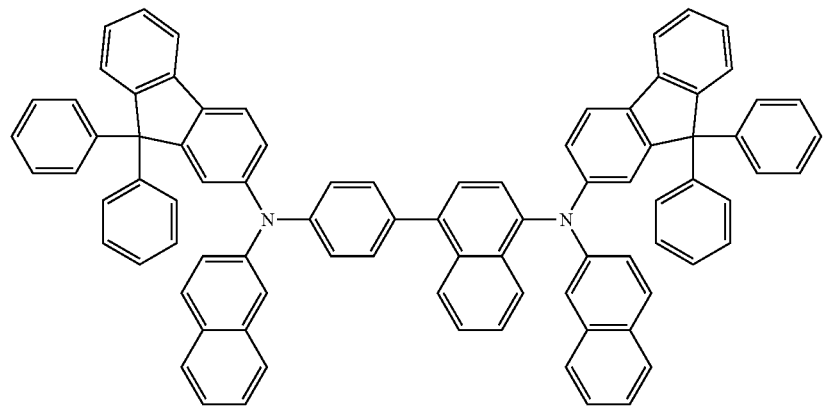
179
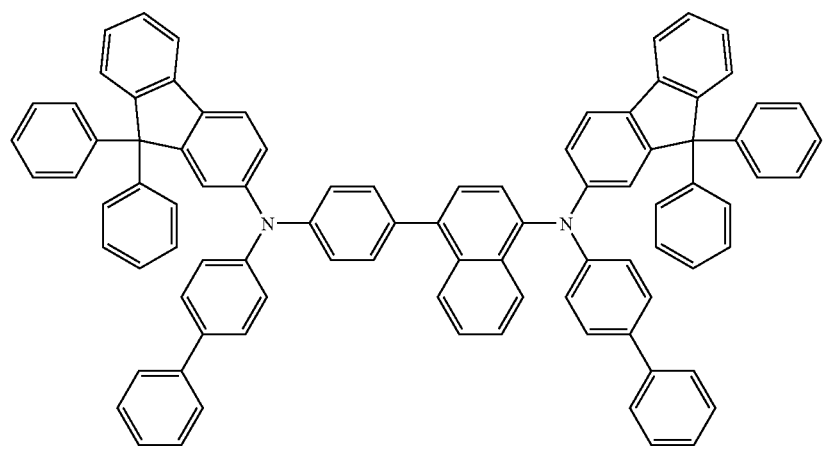
180
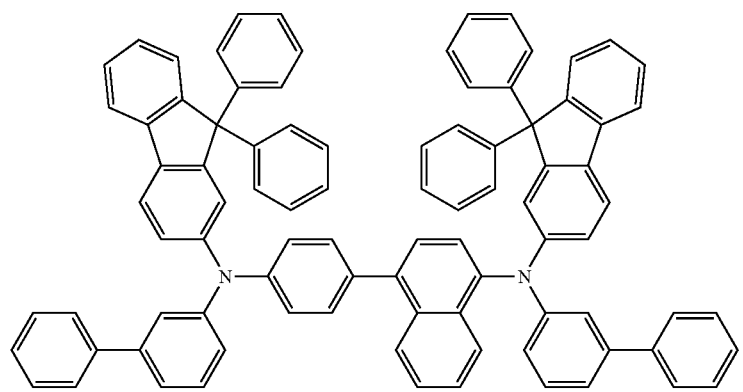
181
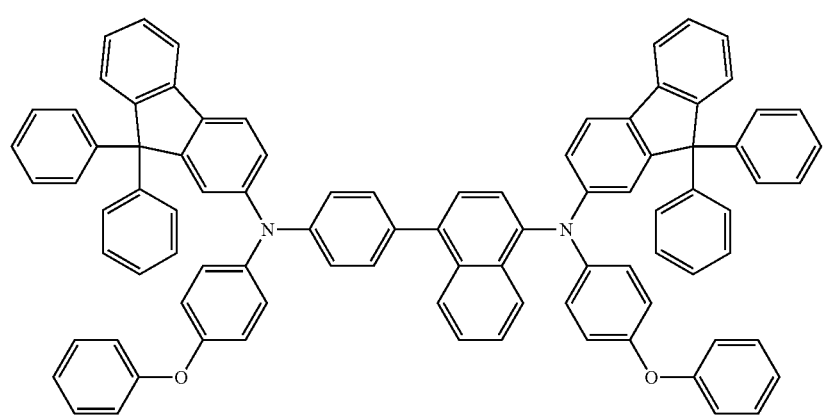

182
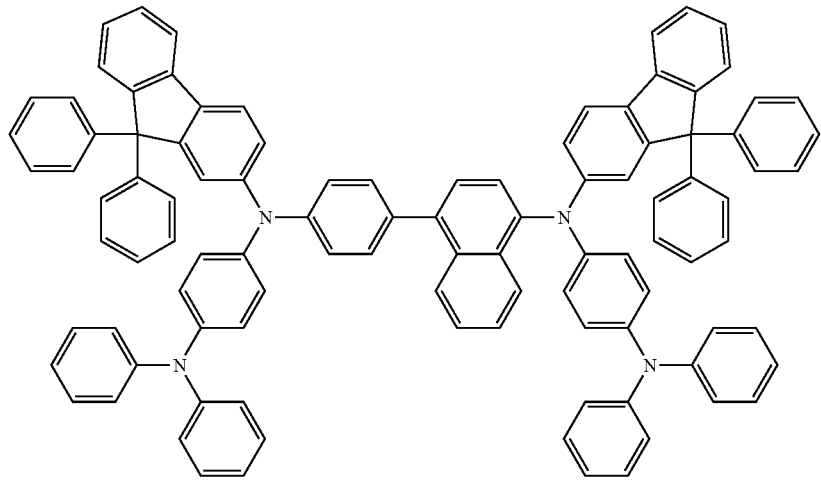
183
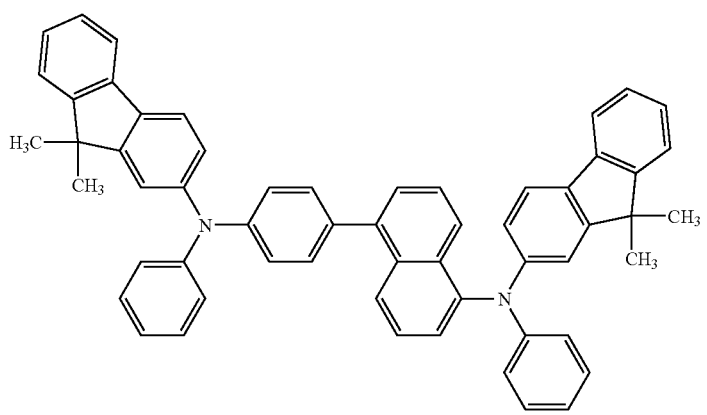
184
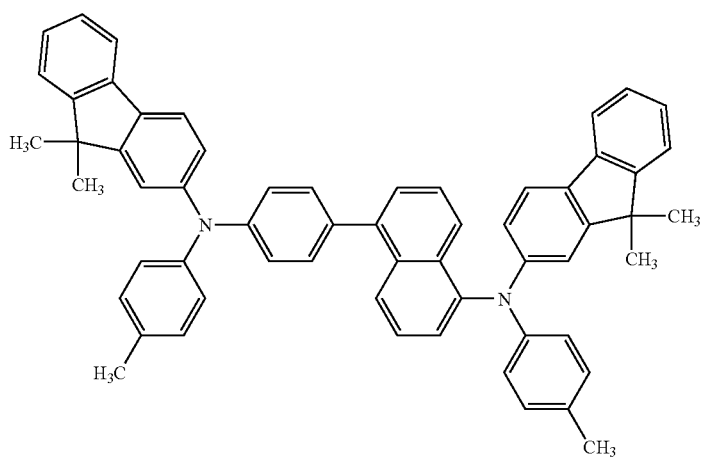

185
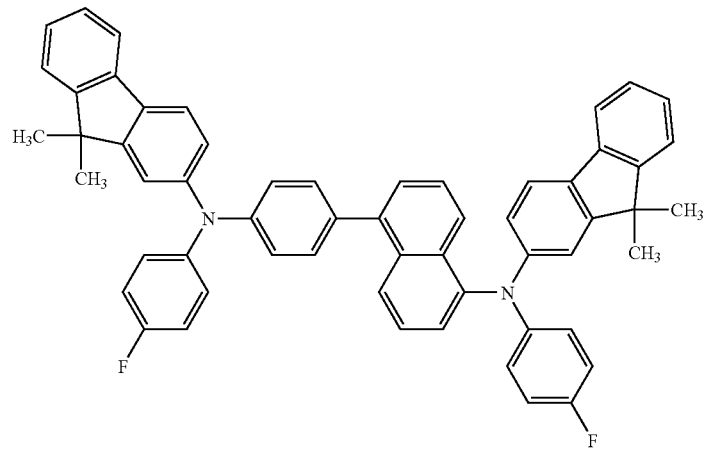
186
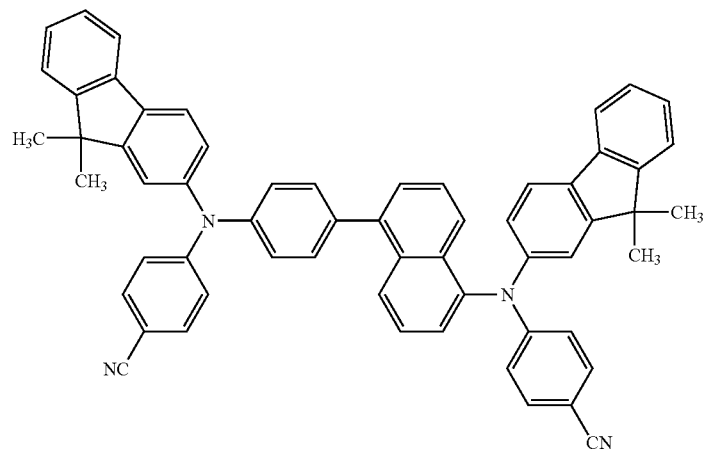
187
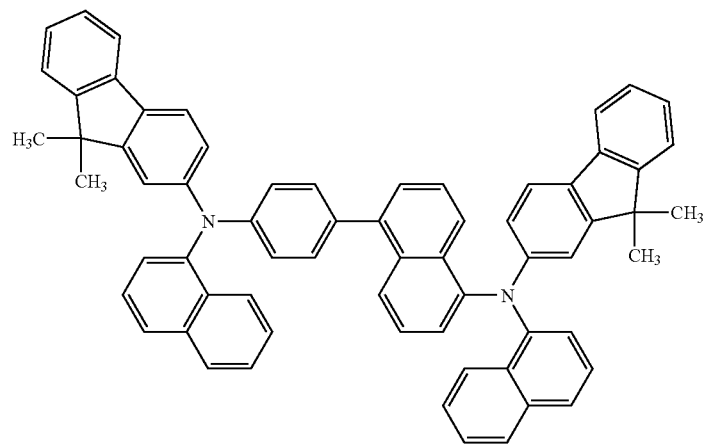

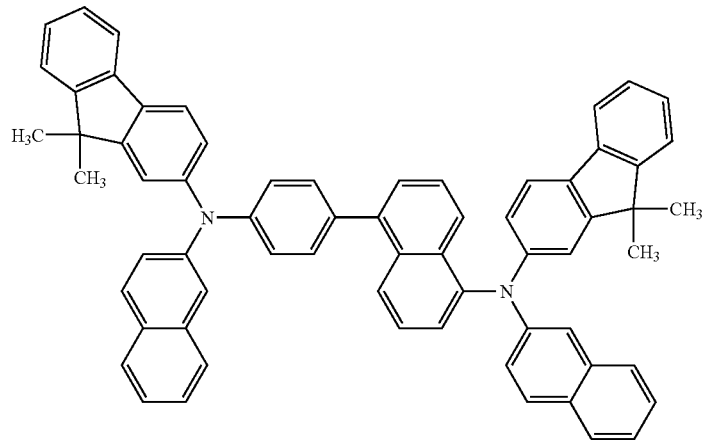
188
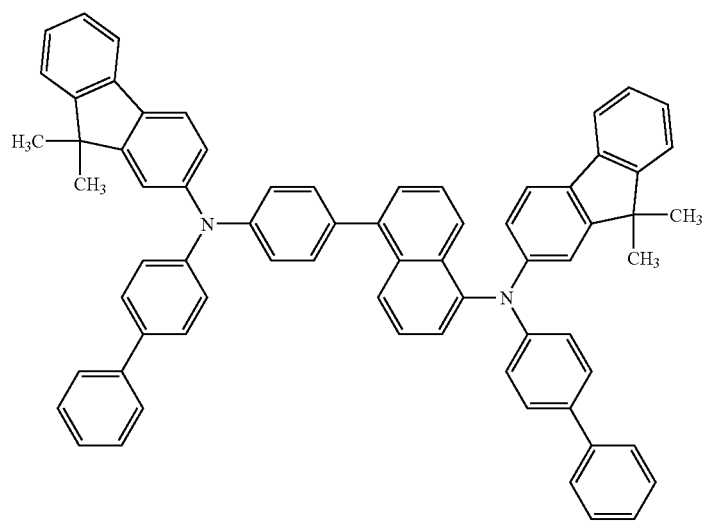
189
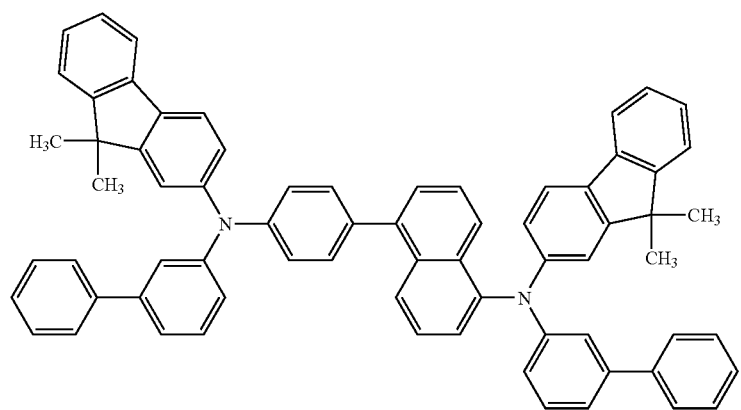
190

191
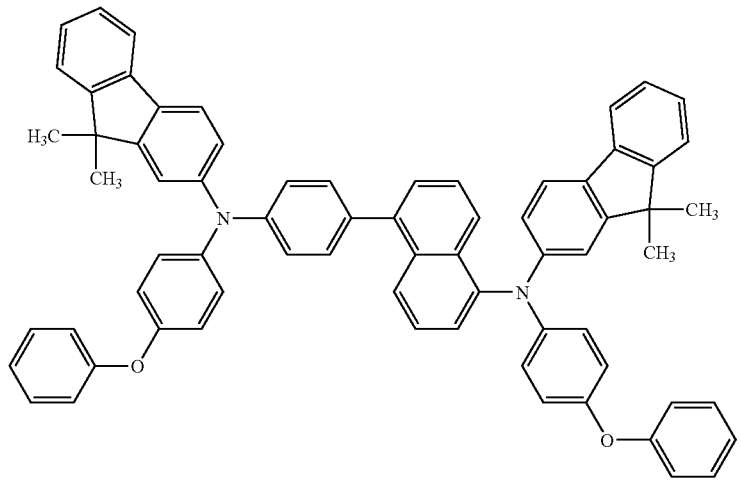
192
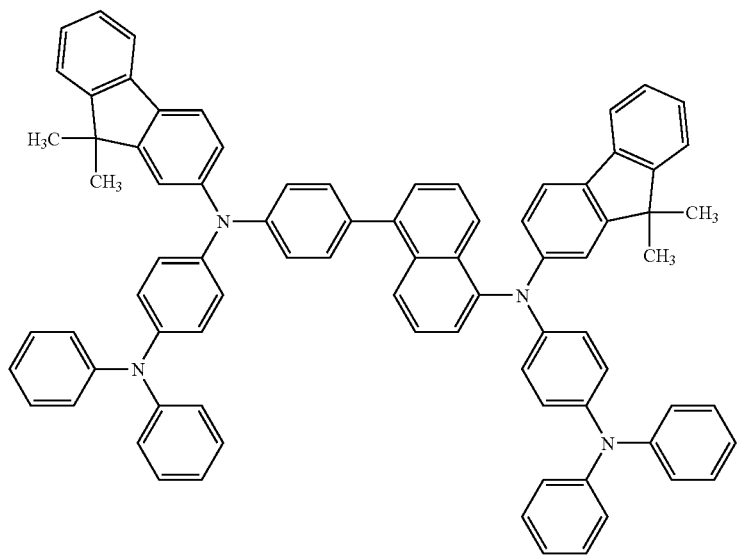
193
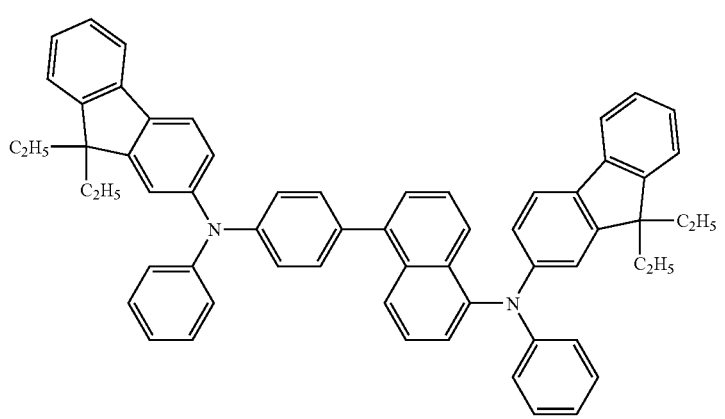

194
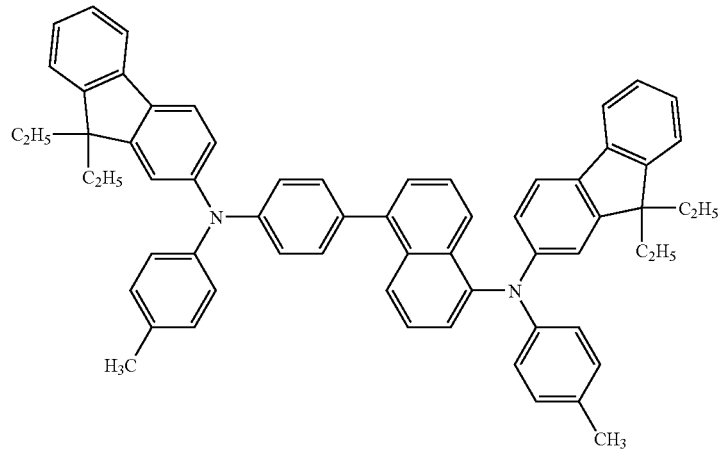
195
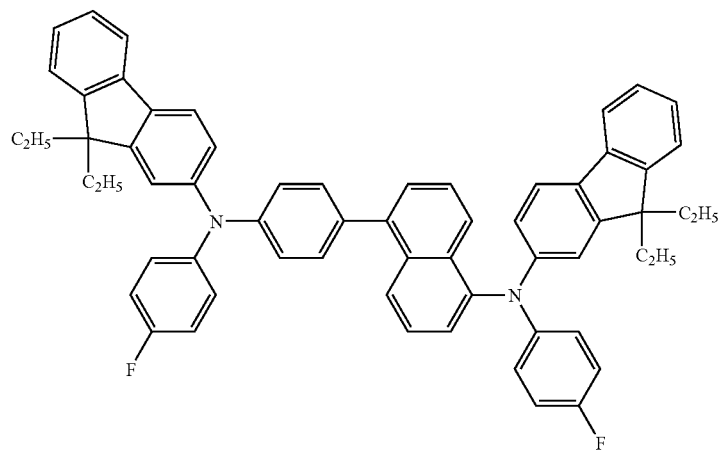
196
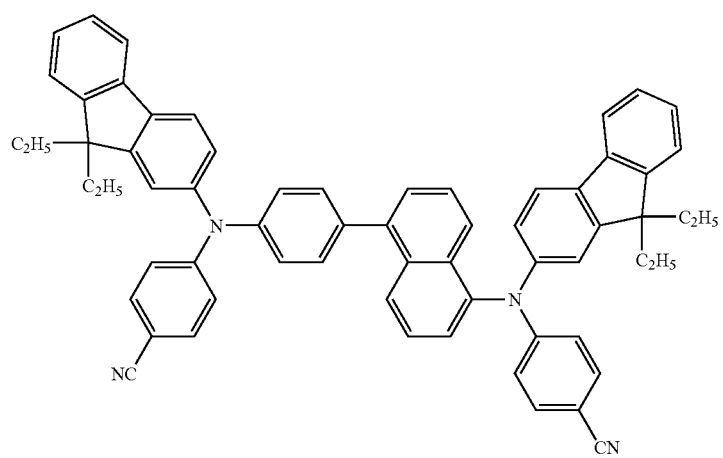

197
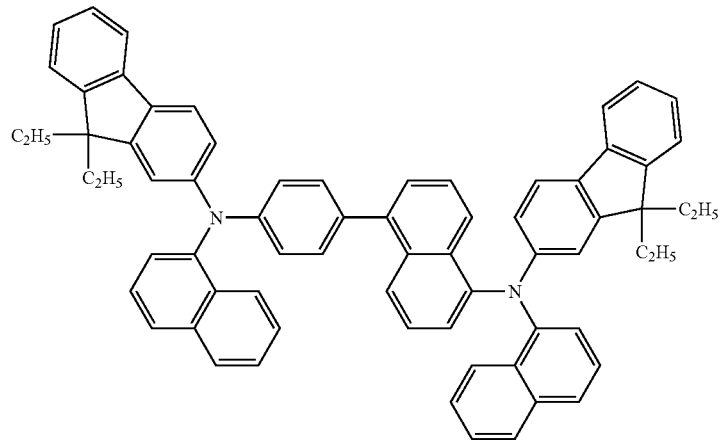
198
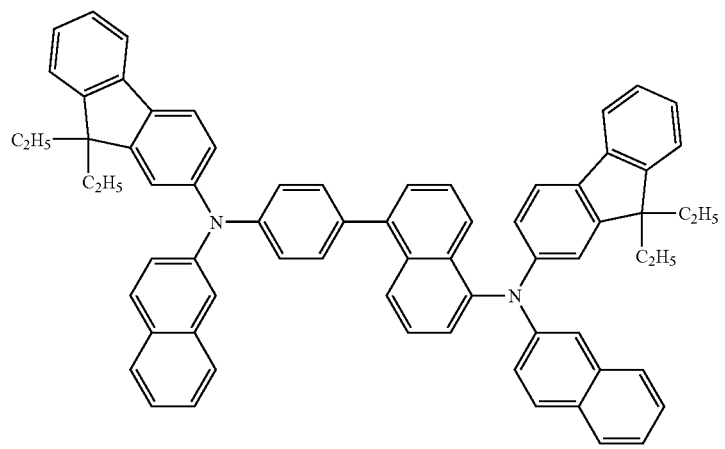
199
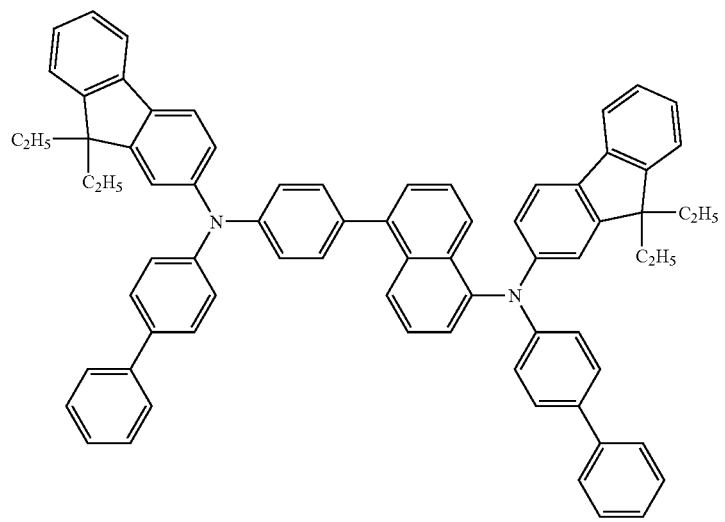

200
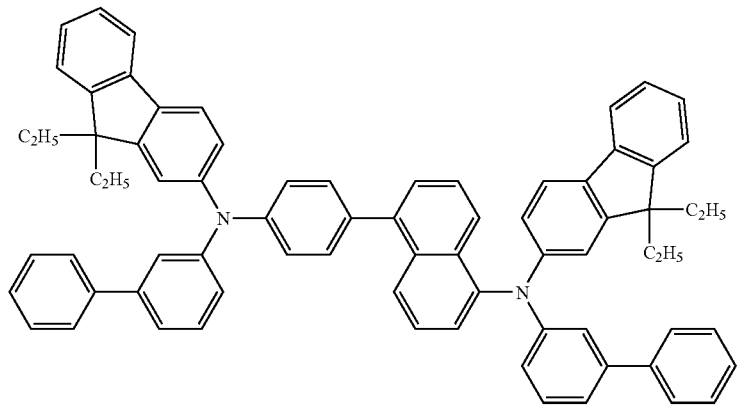
201
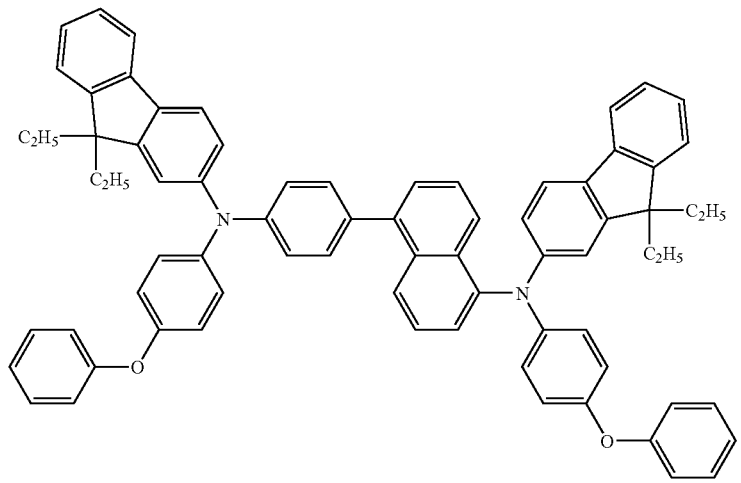
202
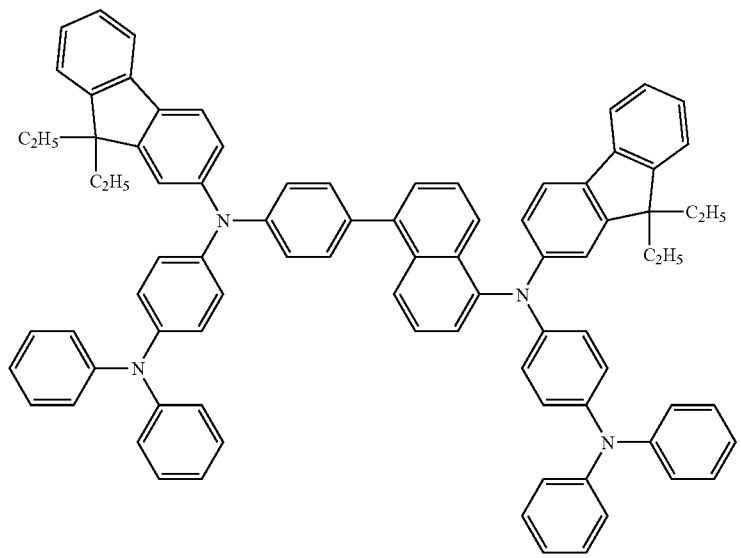

-continued
203
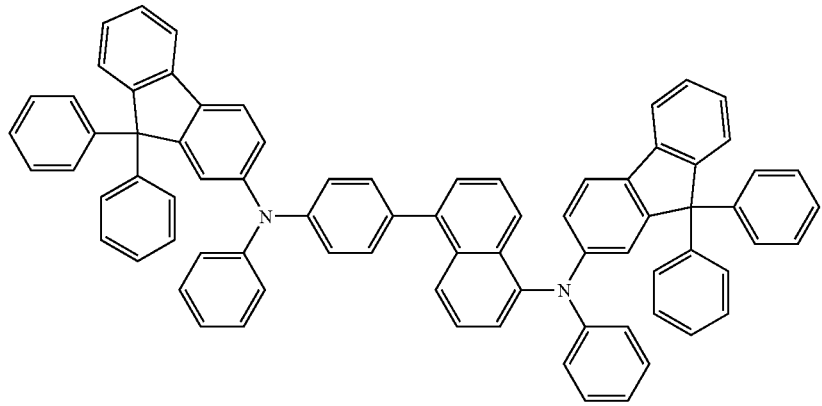
204
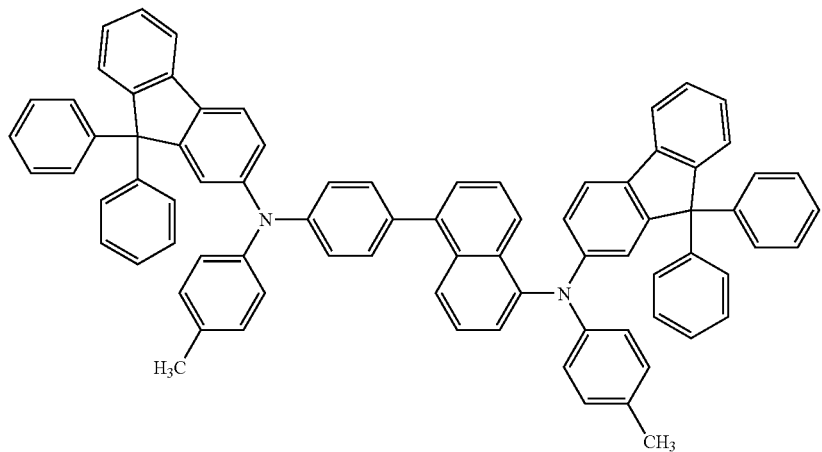
205
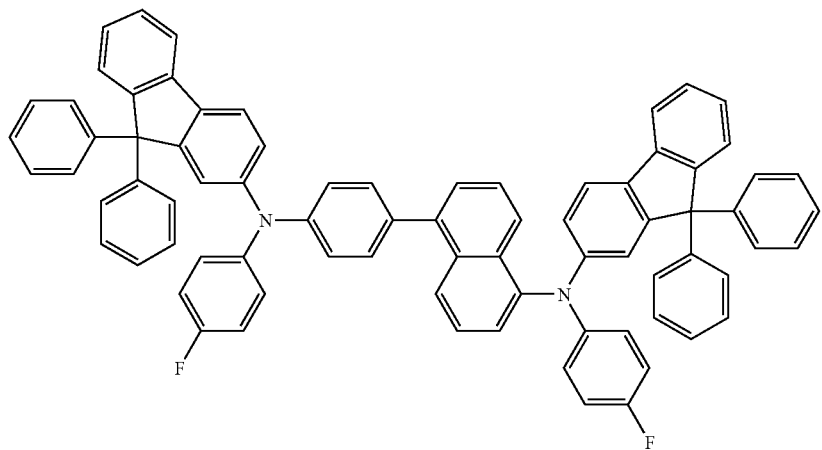

206
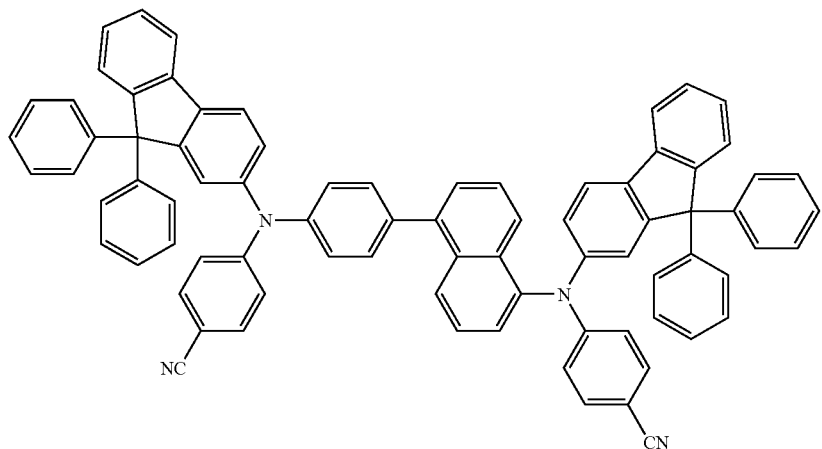
207
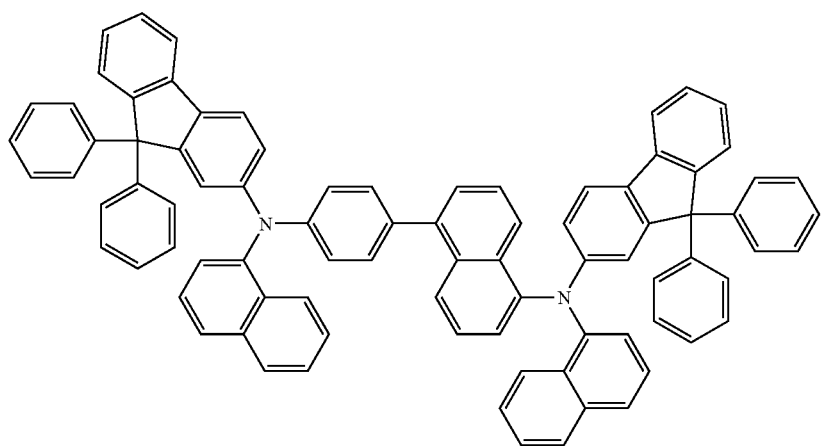
208
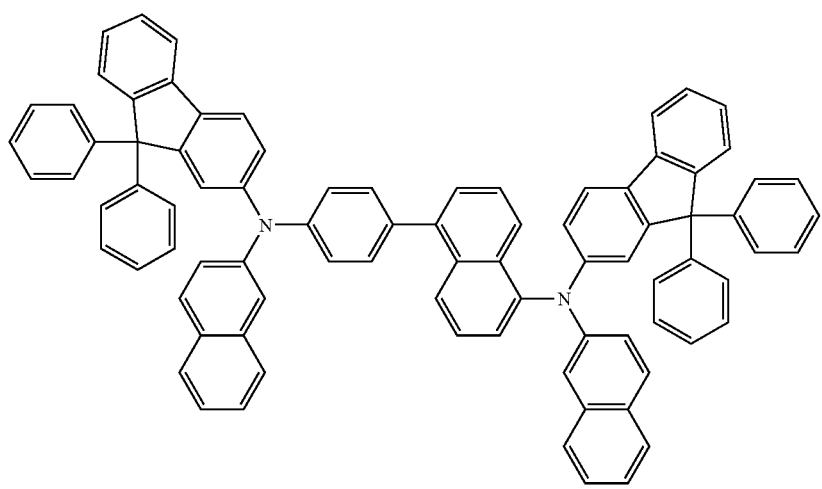

209
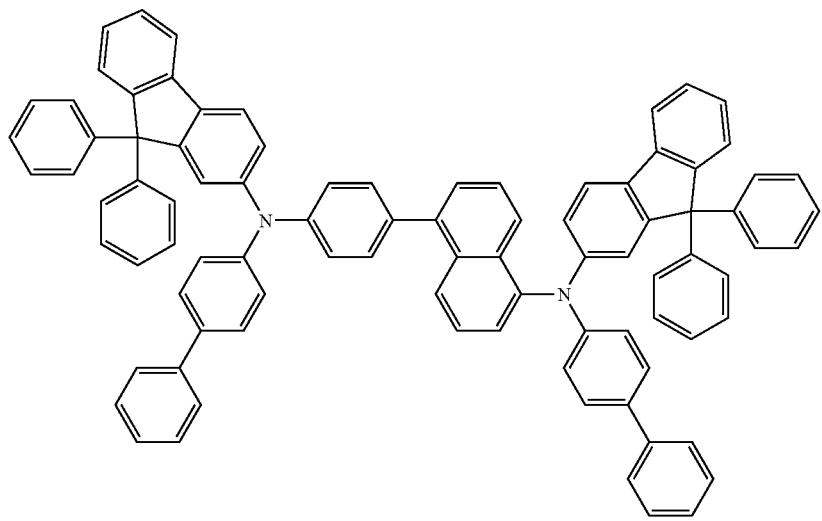
210
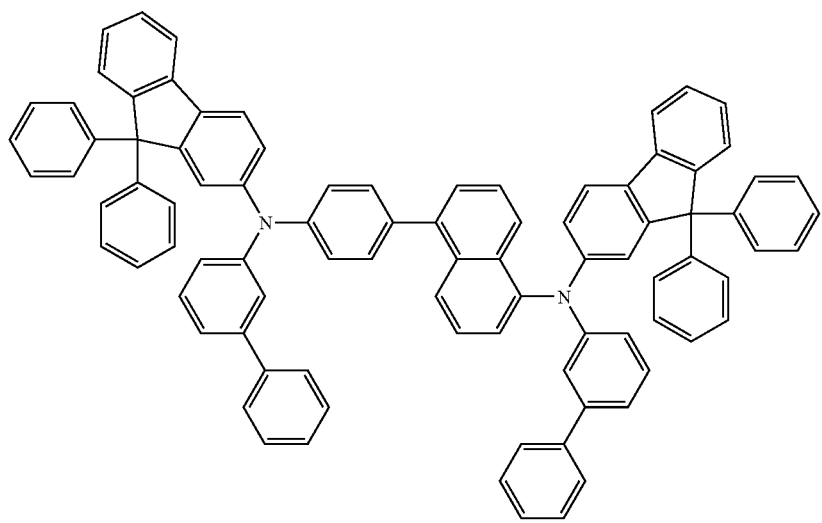
211
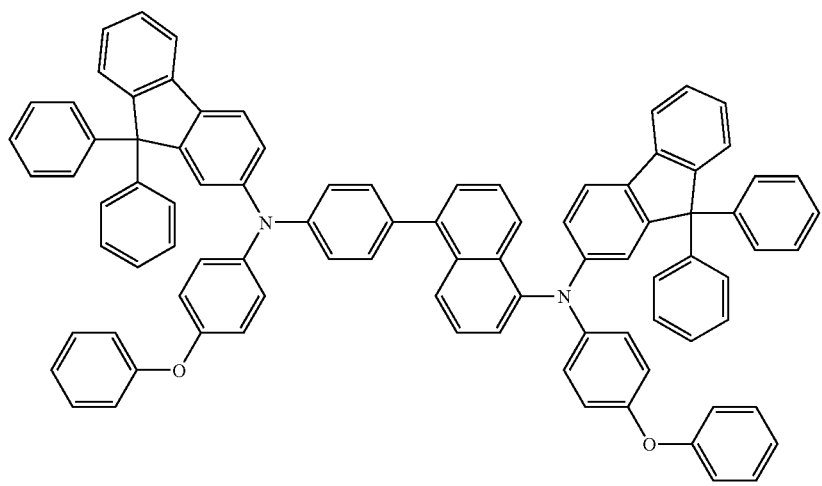

212
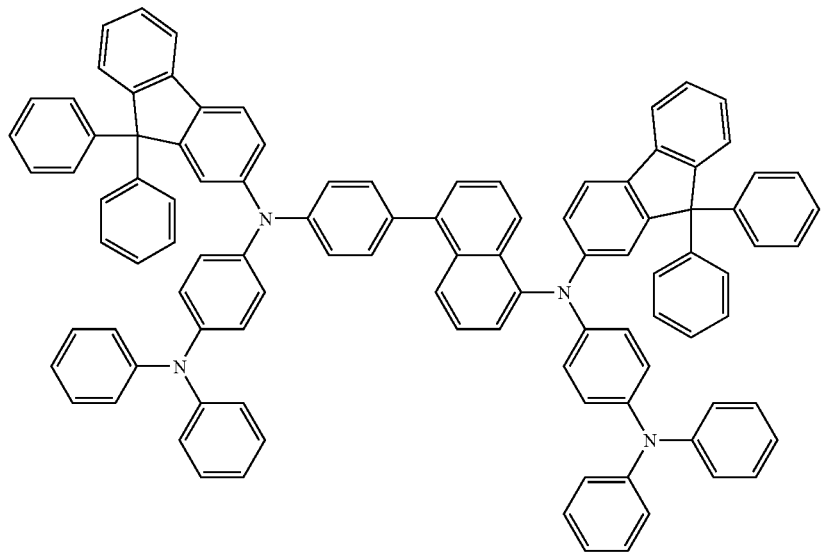
213
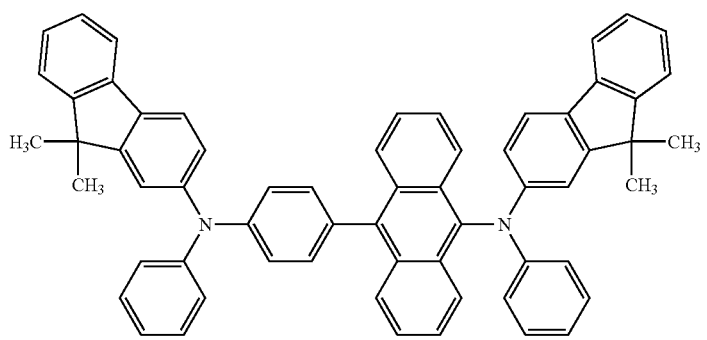
214
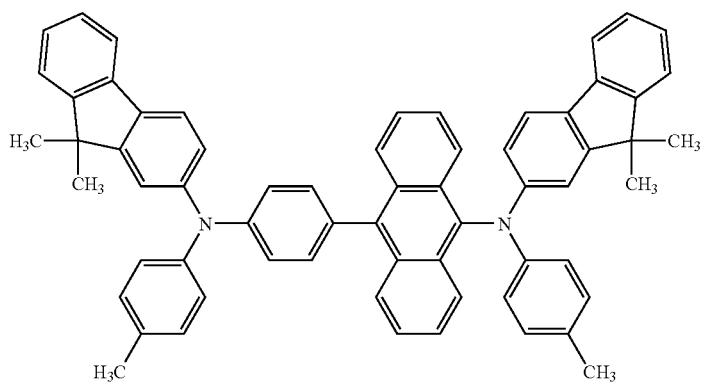
215
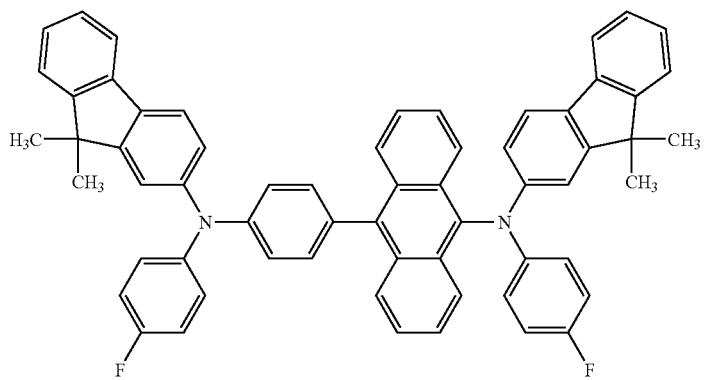

216
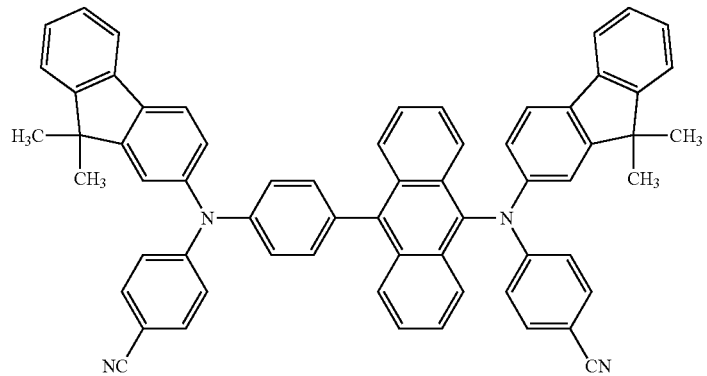
217
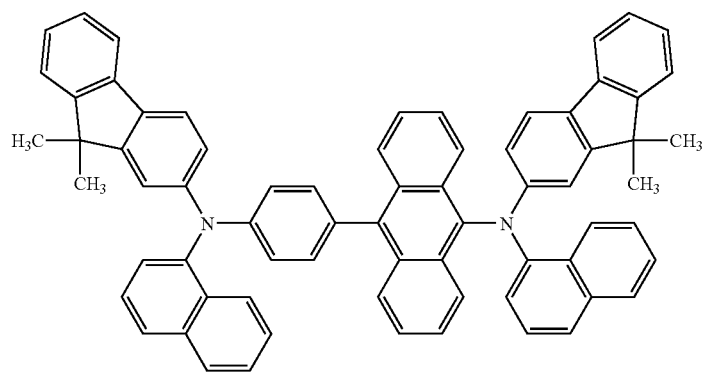
218
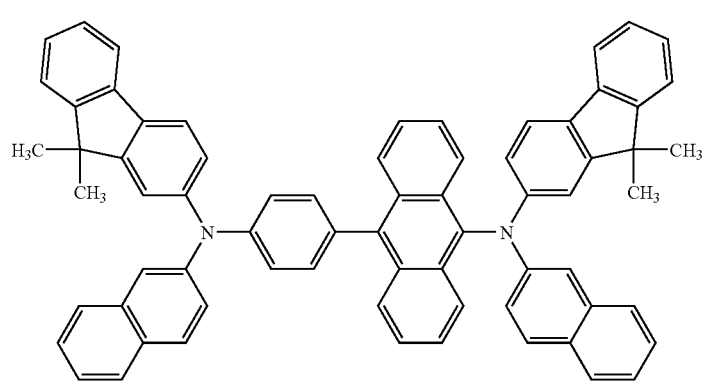
219
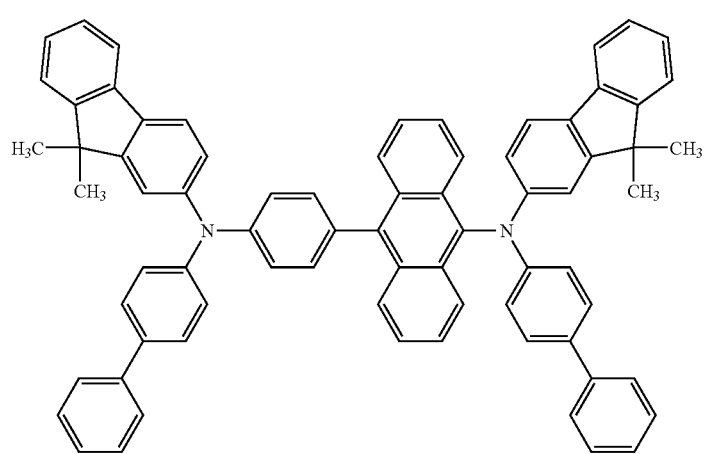

220
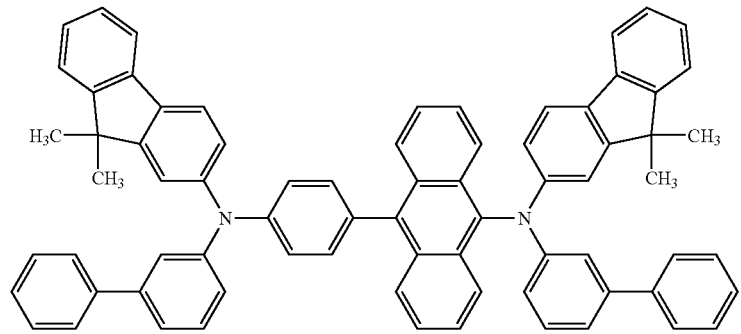
221
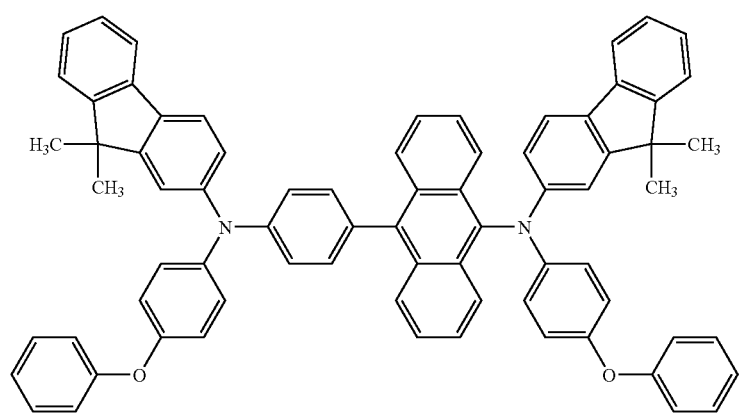
222
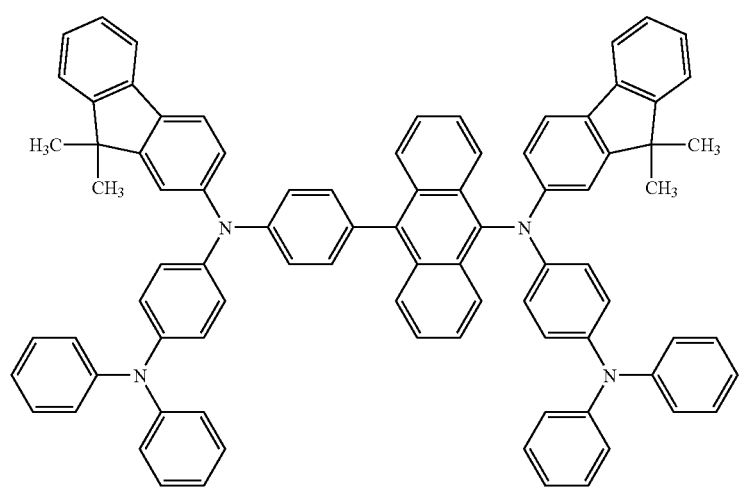
223
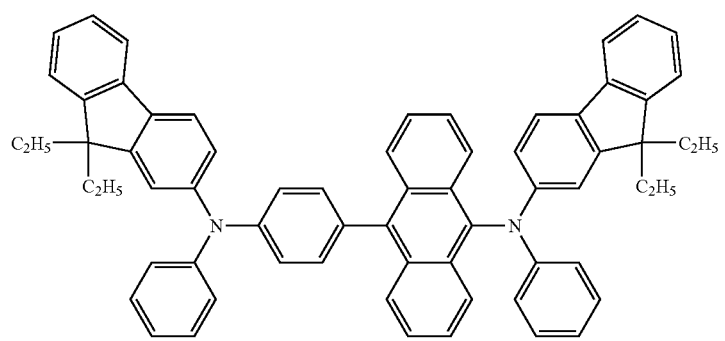

224
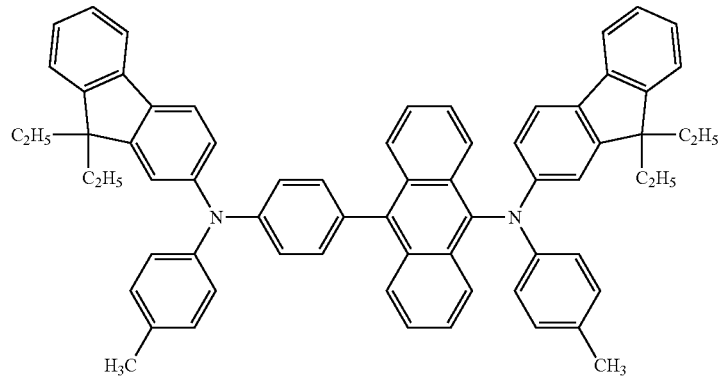
225
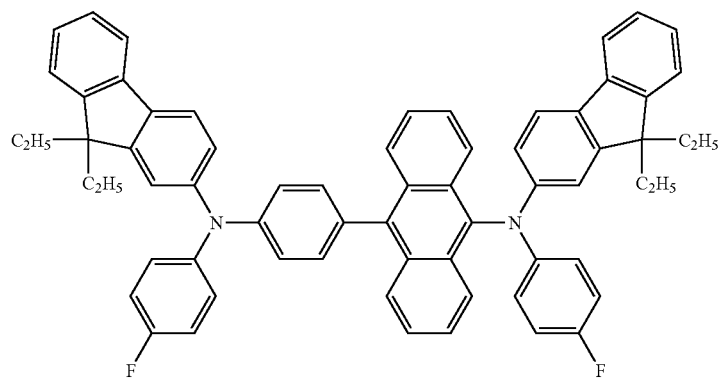
226
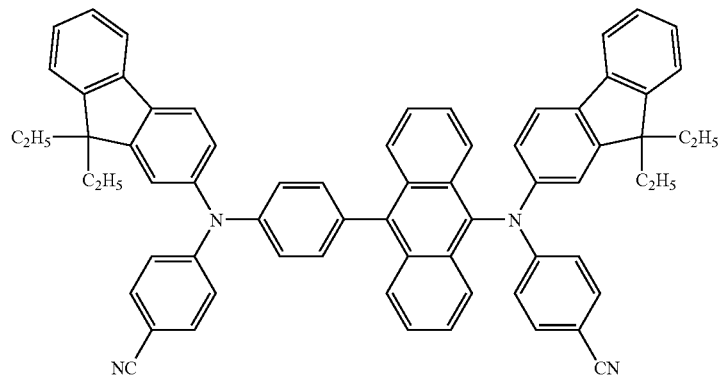
227
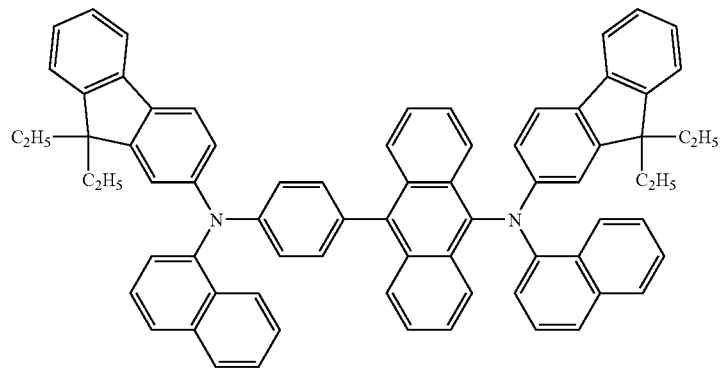

228
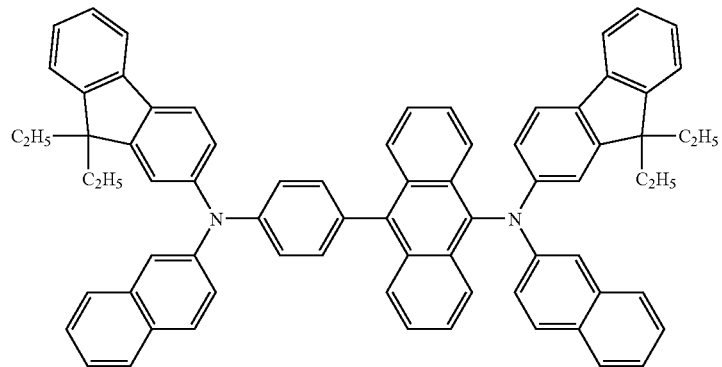
229
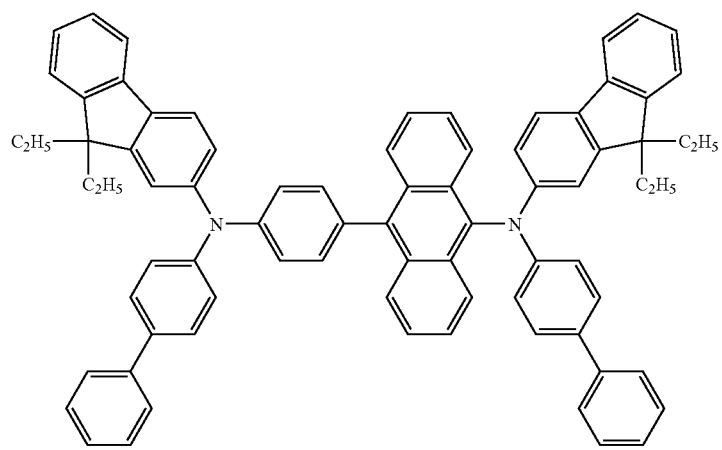
230
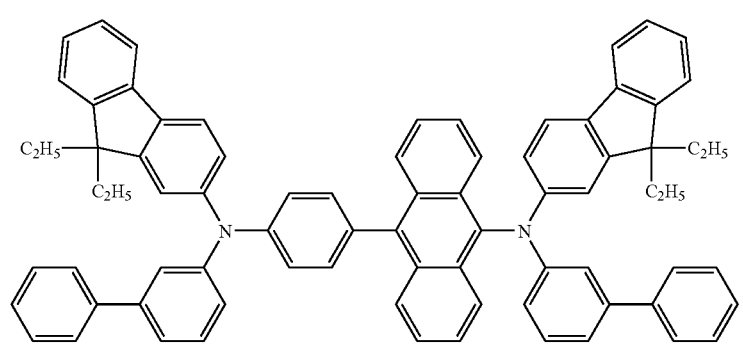
231
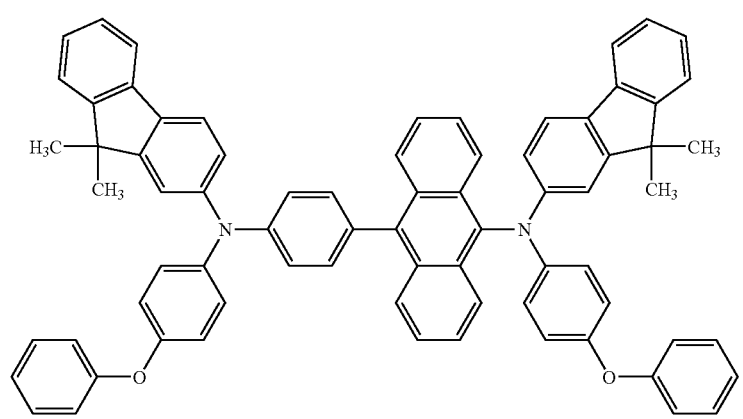

232
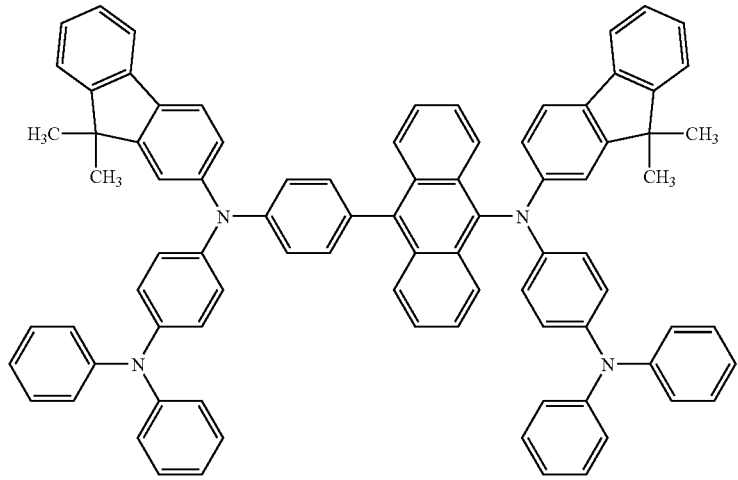
233
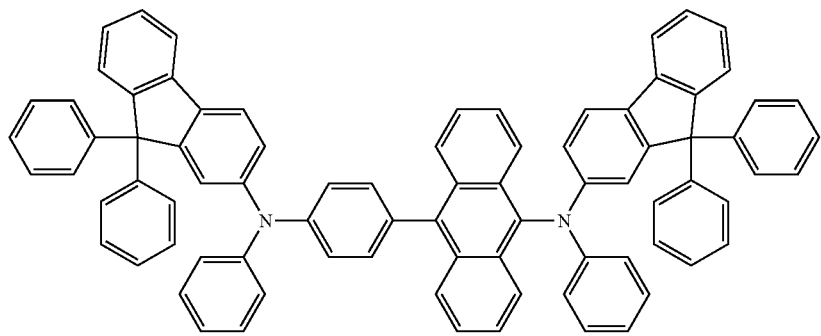
234
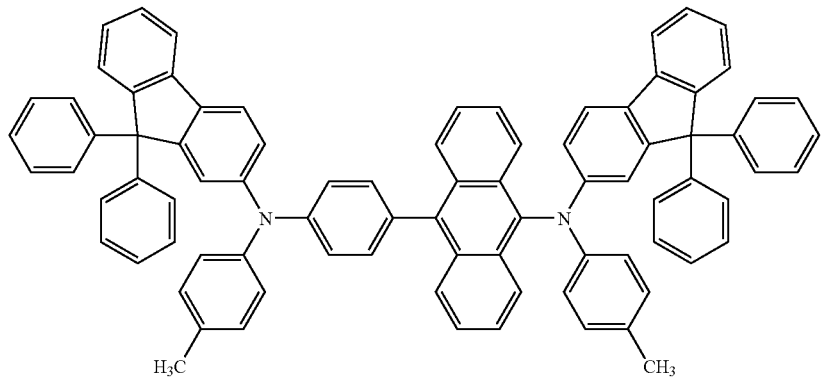
235
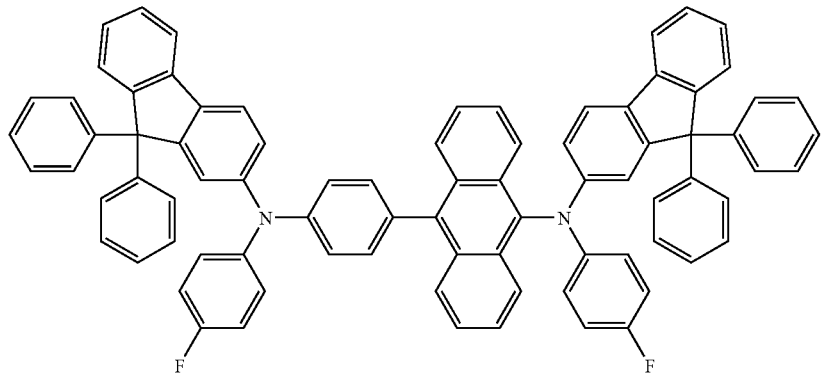

236
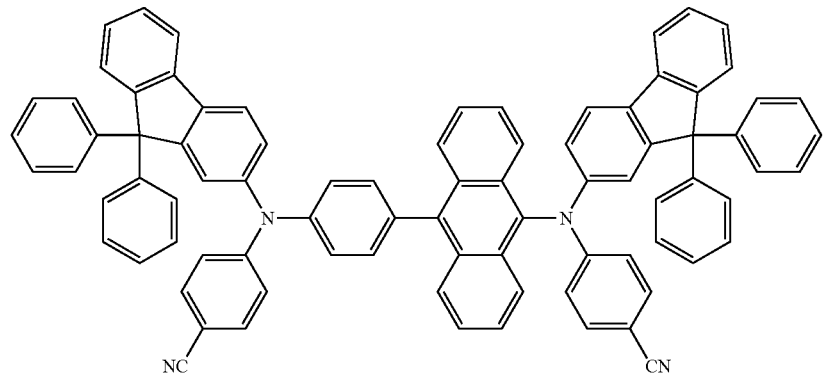
237
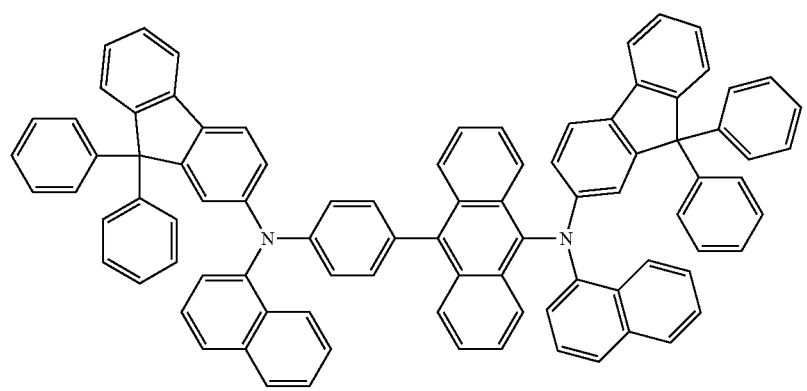
238
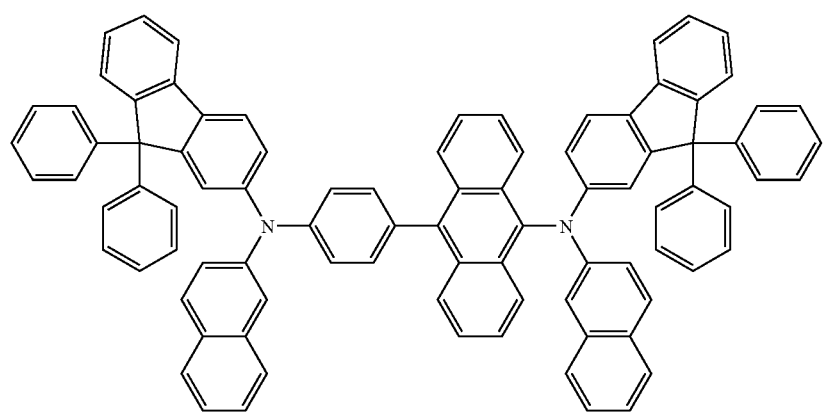
239
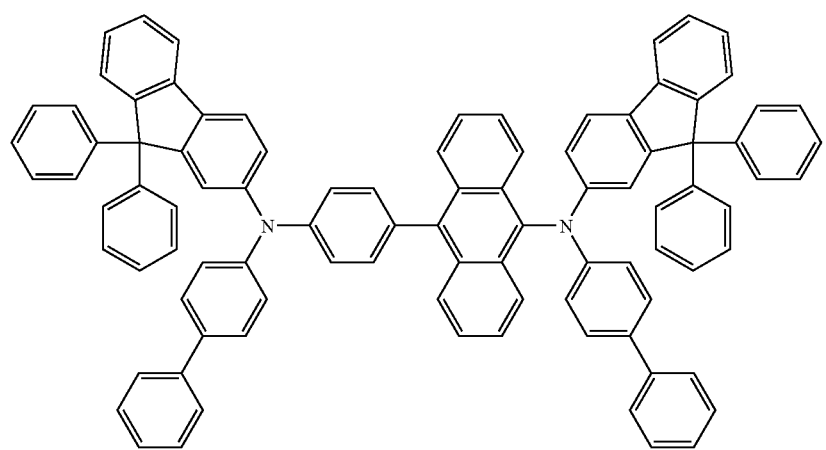

-continued

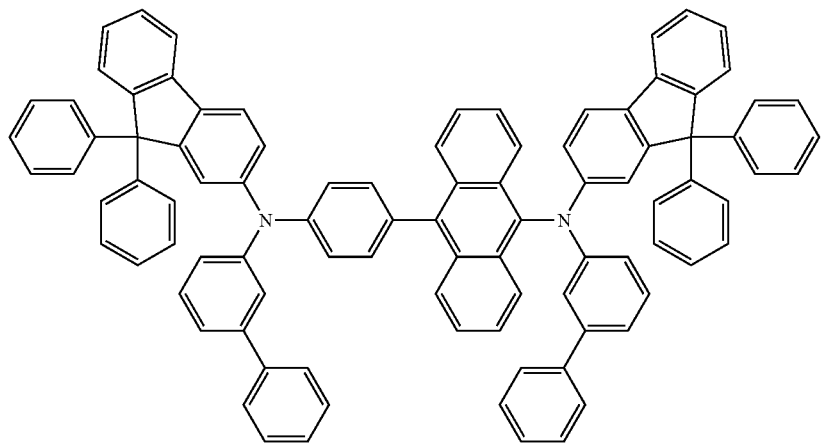

240

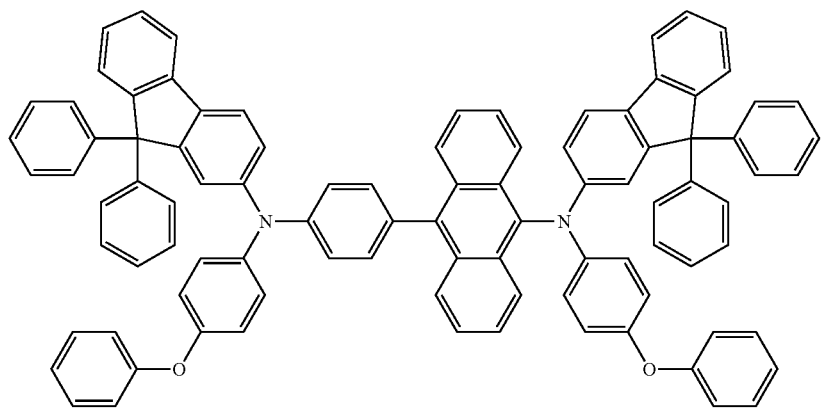

241

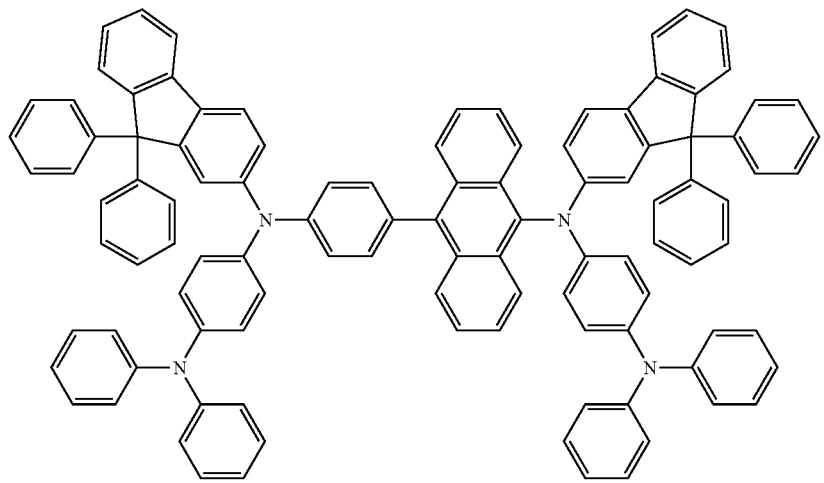

242

In some embodiments, for example, the compound satisfying Formula 1 is selected from Compounds 1, 2, 3, 32, 105, 153, 157, 159, 173, 184 and 213 above.

According to another embodiment of the present invention, an organic light-emitting device includes a first electrode, a second electrode, and an organic film between the first electrode and the second electrode. The organic film includes a compound represented by Formula 1 and may be a hole injection layer or a hole transport layer. The organic film may also be a single film having both a hole injection function and a hole transport function. Alternatively, the organic film may be an emissive layer. The compound represented by Formula 1 may be used as a host material for phosphorescent or fluorescent blue, green, or red color materials.

In one embodiment, the organic film may be a hole injection layer or a hole transport layer.

The first electrode may be an anode, and the second electrode may be a cathode. Alternatively, the first electrode may be a cathode, and the second electrode may be an anode.

The organic light emitting device may further include, whenever necessary or desired, at least one additional layer selected from hole injection layers, hole transport layers, electron blocking layers, emissive layers, hole blocking layers, electron transport layers, and electron injection layers. In addition, the organic light emitting device may include a double-layered organic layer including two of the above organic layers, whenever necessary or desired.

For example, an organic light emitting device according to embodiments of the present invention may have a first electrode/hole injection layer/emissive layer/second electrode structure, a first electrode/hole injection layer/hole transport layer/emissive layer/electron transport layer/second electrode structure, or a first electrode/hole injection layer/hole transport layer/emissive layer/electron transport layer/electron injection layer/second electrode structure. Alternatively, the organic light emitting device may have a first electrode/single organic film with both hole injection and hole transport functions/emissive layer/electron transport layer/second electrode structure, or a first electrode/single organic film with both hole injection and hole transport functions/emissive layer/electron transport layer/electron injection layer/second electrode structure.

The organic light emitting devices according to embodiments of the present invention may be used in various applications such as top emission type organic light emitting devices and bottom emission type organic light emitting devices.

A method of preparing an organic light emitting device according to an embodiment of the present invention will now be described with reference to the organic light emitting device illustrated in FIG. 1. As shown in FIG. 1, an organic light emitting device according to one embodiment of the present invention includes a substrate, a first electrode (e.g., an anode), a hole injection layer, a hole transport layer, an emissive layer, an electron transport layer, and a second electrode (e.g., a cathode).

The first electrode is formed by applying a first electrode forming material having a high work function on a substrate by deposition or sputtering. The first electrode may either be an anode or a cathode. The substrate may be any conventional substrate used in organic light emitting devices. For example, the substrate may be a glass substrate or a transparent plastic substrate, both of which have excellent mechanical strength, thermal stability, transparency, surface planarity, convenience in handling, and water resistance. The first electrode forming material may include a material selected from indium tin oxide (ITO), indium zinc oxide (IZO), tin oxide ($SnO_2$), zinc oxide (ZnO), Al, Ag, Mg, and combinations thereof. The first electrode forming material has excellent conductivity and may be used to form a transparent or reflective electrode.

The hole injection layer (HIL) may be formed on the first electrode using a variety of methods such as vacuum deposition, spin coating, casting, and Langmuir-Blodget (LB) deposition. When forming the HIL using vacuum deposition, the deposition conditions may differ depending on the compound used as the material for the HIL and the desired structure and thermal properties of the HIL. However, in some embodiments, the deposition conditions may include a deposition temperature ranging from about 100 to about 500° C., a vacuum pressure ranging from about $10^{-8}$ to about $10^{-3}$ torr, a deposition rate ranging from about 0.01 to about 100 Å/sec, and a film thickness ranging from about 10 Å to about 5 μm.

When forming the HIL by spin coating, the coating conditions may differ depending on the compound used as the material for the HIL and the desired structure and thermal properties of the HIL. However, in some embodiments, the spin coating conditions may include a coating speed ranging from about 2000 to about 5000 rpm, and a heat-treatment temperature for removing a solvent after coating ranging from about 80 to about 200° C.

The HIL material may be the compound represented by Formula 1, as described above. Alternatively, any known HIL material may be used. For example, a phthalocyanine compound (such as copper phthalocyanine) may be used. Additionally, TCTA (shown below), m-MTDATA (shown below) and m-MTDAPB, which are starburst-type amine derivatives can be used. Soluble conductive polymers, such as Pani/DBSA (polyaniline/dodecylbenzenesulfonic acid), PEDOT/PSS (poly(3,4-ethylenedioxythiophene)/poly(4-styrene-sulfonate), Pani/CSA (polyaniline/camphor sulfonic acid), and PANI/PSS (polyaniline)/poly(4-styrene-sulfonate) may also be used.

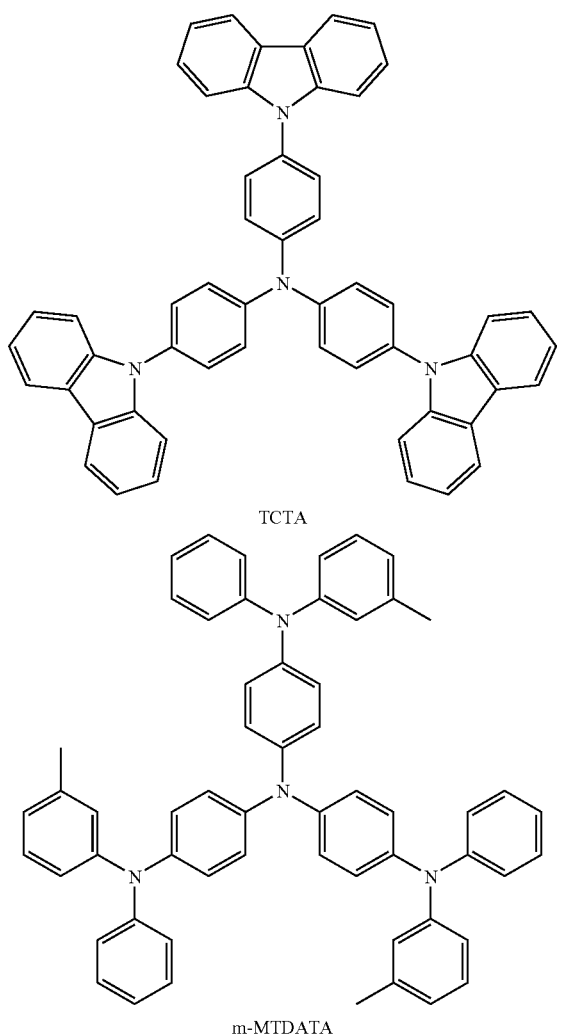

TCTA m-MTDATA

The thickness of the HIL may range from about 100 to about 10000 Å. For example, in one embodiment, the thickness may range from about 100 to about 1000 Å. If the thickness of the HIL is less than about 100 Å, the hole injection properties may deteriorate, and if the thickness of the HIL is greater than about 10000 Å, the driving voltage may increase.

The hole transport layer (HTL) may be formed on the HIL by a variety of methods, such as vacuum deposition, spin coating, casting, and LB deposition. When the HTL is formed using vacuum deposition or spin coating, the deposition or coating conditions may differ depending on the compounds used, but may generally include the deposition and coating conditions described above with respect to the HIL.

The HTL material may be a compound represented by Formula 1 described above. Alternatively, any known HTL material may be used, for example, carbazole derivatives (such as N-phenylcarbazole and polyvinylcarbazole) and conventional amine derivatives having condensed aromatic condensed rings (such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD) (shown below), and N,N'-di(naphthalene-1-yl)-N,N'-diphenyl benzidine (α-NPD) (shown below)).

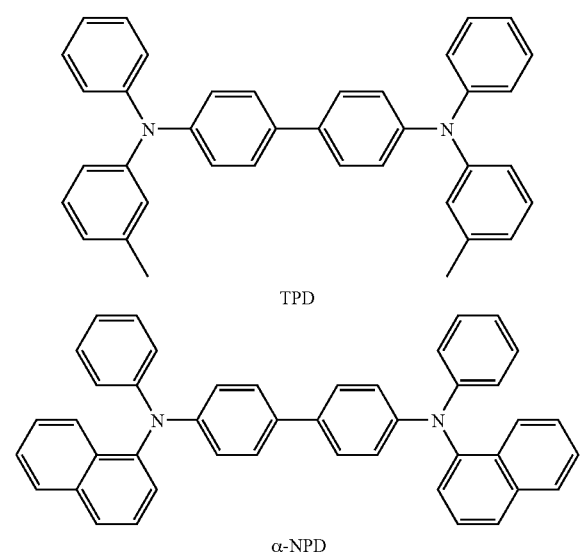

The thickness of the HTL may range from about 50 to about 1000 Å. For example, in one embodiment, the thickness ranges from about 100 to about 600 Å. If the thickness of the HTL is less than about 50 Å, the hole transporting properties may deteriorate, and if the thickness of the HTL is greater than about 1000 Å, the driving voltage may increase.

The emissive layer (EML) may be formed on the HTL by a variety of methods, such as vacuum deposition, spin coating, casting, and LB deposition. When the EML is formed by vacuum deposition or spin coating, the deposition or coating conditions may differ depending on the compounds used, but may generally include the deposition and coating conditions described above with respect to the HIL.

The EML may include a compound represented by Formula 1 described above. In particular, the compound represented by Formula 1 may be used as a host. The EML may be formed using a variety of known light emitting materials, and may be formed using known hosts and dopants. The dopant may be any known dopant and may be either a phosphorescent dopant or a fluorescent dopant.

Nonlimiting examples of suitable hosts include Alq$_3$, CPB (4,4'-N,N'-dicarbazole-biphenyl), PVK (poly(n-vinylcarbazole)), DSA (distyrylarylene), or IDE215 (from Idemitsu Co.).

Nonlimiting examples of suitable phosphorescent dopants include IDE102, IDE105 and IDE118 (available from Idemitsu Co.). Nonlimiting examples of suitable fluorescent dopants include Ir(ppy)$_3$ (ppy is an abbreviation of phenylpyridine)(green), 4,6-F2(ppy)$_2$Irpic, TEB002 (from Cobion Co.), PtOEP (platinum(II)octaethylporphyrin), compounds represented by Formula 3 below, Firpric (shown below), and RD61 (which is a red fluorescent dopant from UDC Co.).

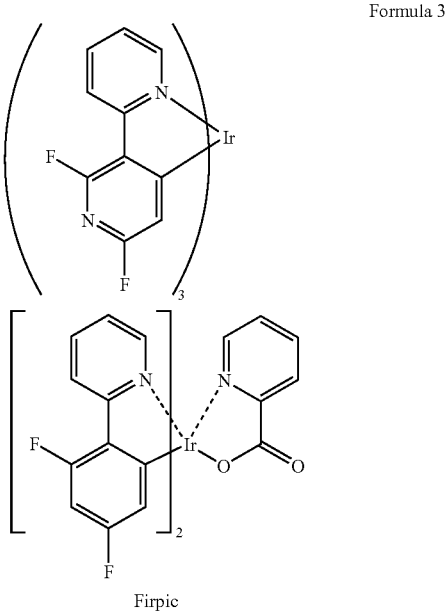

The content of the dopant may range from about 0.1 to about 20 parts by weight based on 100 parts by weight of the EML forming material (i.e., the total weight of the host and the dopant is 100 parts by weight). In one embodiment, for example, the dopant is present in an amount ranging from about 0.5 to about 12 parts by weight based on 100 parts by weight of the EML forming material. If the dopant is present in an amount less than about 0.1 parts by weight based on the total weight of the host and the dopant, the effect of adding the dopant is minute. If the dopant is present in an amount greater than about 20 parts by weight based on the total weight of the host and the dopant, concentration extinction (e.g. concentration quenching) of both the phosphorescent and the fluorescent components may occur.

The thickness of the EML may range from about 100 to about 1000 Å. In one embodiment, for example, the thickness ranges from about 200 to about 600 Å. If the thickness of the EML is less than about 100 Å, the light emitting properties may deteriorate, and if the thickness of the EML is greater than about 1000 Å, the driving voltage may increase.

When the EML includes a phosphorescent dopant, a hole blocking layer (HBL) may be formed on the EML to prevent triplet excitons or holes from diffusing to the electron transport layer (not shown in FIG. 1). The HBL material is not particularly limited, and may be selected from any known HBL materials. Nonlimiting examples of suitable HBL materials include oxadiazole derivatives, triazole derivatives, phenathroline derivatives, Balq and BCP.

The thickness of the HBL may range from about 50 to about 1000 Å. In one embodiment, for example, the thickness may range from about 100 to about 300 Å. If the thickness of the HBL is less than about 50 Å, the hole-blocking properties may deteriorate, and if the thickness of the HBL is greater than about 1000 Å, the driving voltage may increase.

The electron transport layer (ETL) may be formed on the HBL or on the EML by a variety of methods, such as vacuum deposition, spin coating, and casting. When the ETL is formed by vacuum deposition or spin coating, the deposition or coating conditions may differ depending on the compounds used, but may generally include the deposition and coating conditions described above with respect to the HIL.

The ETL material is not particularly limited, and may be selected from any known ETL forming materials. Nonlimiting examples of suitable ETL materials include quinoline derivatives, and in particular, tris(8-quinolinolate)aluminum ($Alq_3$) and TAZ.

The thickness of the ETL may range from about 100 to about 1000 Å. In one embodiment, for example, the thickness ranges from about 100 to about 500 Å. If the thickness of the ETL is less than about 100 Å, the electron transporting properties may deteriorate, and if the thickness of the EML is greater than about 1000 Å, the driving voltage may increase.

In addition, an electron injection layer (EIL) may be deposited on the ETL. The EIL facilitates the injection of electrons from the cathode. The EIL may be formed of any known EIL material, nonlimiting examples of which include LiF, NaCl, CsF, $Li_2O$, and BaO. The deposition or coating conditions may differ depending on the compounds used, but may generally include the deposition and coating conditions described above with respect to the HIL.

The thickness of the EIL may range from about 1 to about 100 Å. In one embodiment, for example, the thickness may range from about 5 to about 90 Å. If the thickness of the EIL is less than about 1 Å, the electron injecting properties may deteriorate, and if the thickness of the EIL is greater than about 100 Å, the driving voltage may increase.

Finally, the second electrode may be formed on the EIL by any suitable method, such as vacuum deposition or sputtering. The second electrode may be a cathode or an anode. The material for forming the second electrode may be a metal, an alloy, or an electrically conductive compound with a low work function. Nonlimiting examples of such materials include Li, Mg, Al, Al—Li, Ca, Mg—In, and Mg—Ag. In addition, a transparent cathode, such as ITO or IZO may be used in order to obtain a top emission device.

The organic light emitting device according to embodiments of the present invention may be used in many applications, including flat panel display devices such as passive matrix organic light emitting display devices and active matrix organic light emitting display devices. In particular, when the organic light emitting device is included in an active matrix organic light emitting display device, the first electrode on the substrate is a pixel electrode and is electrically connected to a source electrode or a drain electrode of a thin film transistor. Moreover, the organic light-emitting device may also be included in a flat panel display device having a double-sided screen.

The following Examples and Synthesis Examples describe compounds 1, 2, 3, 32, 105, 153, 173, 184, and 242 and the synthesis thereof. However, the Examples and Synthesis Examples are presented for illustrative purposes only and do not limit the scope of the present invention.

SYNTHESIS EXAMPLE 1

Preparation of Compound 1

Compound 1 was synthesized by the reaction pathway represented by Reaction Scheme 1 below.

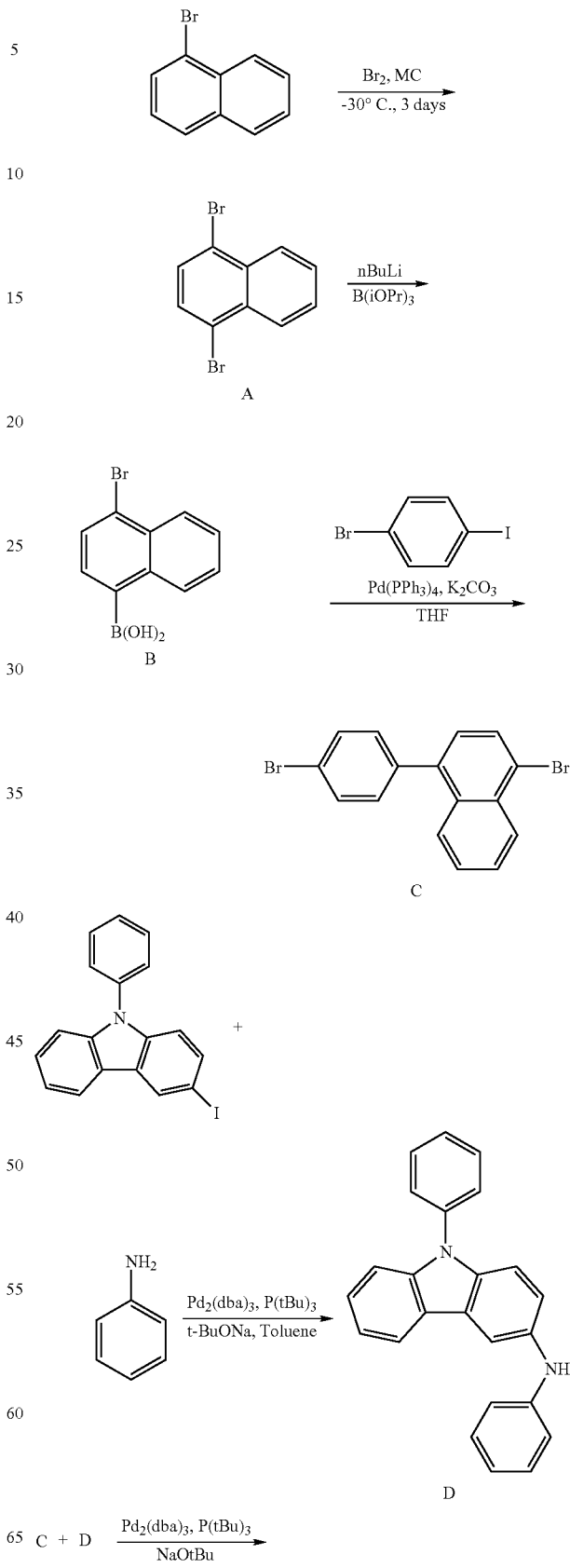

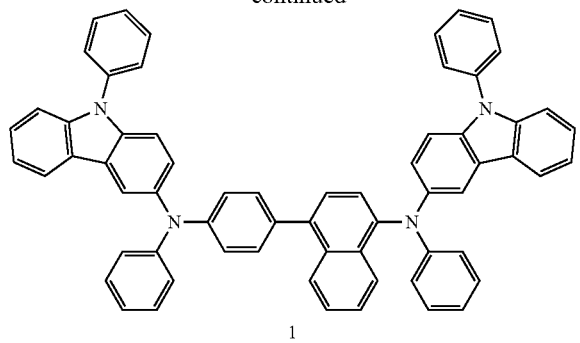

1

Synthesis of Intermediate A 20.7 g (100 mmol) of 1-bromonaphthalene was dissolved in 300 ml dichloromethane, and was maintained at a temperature of −30° C. A solution of 2.56 g (50 mmol) of bromine dissolved in 30 ml of dichloromethane was adjusted to a temperature of −30° C. and then slowly added to the 1-bromonaphthalene solution. The resulting product was blocked from light, and incubated in a freezer at −30° C. for 48 hours. After the reaction was complete, 10% sodium thiosulfate solution was added to the solution, and an organic layer was collected from the solution. The collected organic layer was dried with magnesium sulfate, and the residue obtained by evaporating the solvent was recrystallized with diethyl ether and normal hexane to obtain 24.3 g of Intermediate A, a white solid (yield: 85%). The structure of the product was confirmed by $^1$H and $^{13}$C NMR. ($^1$H NMR (CDCl$_3$, 400 MHz) δ (ppm) −8.26-8.24 (m, 2H), 7.66-7.63 (m, 4H); $^{13}$C NMR (CDCl$_3$, 100 MHz) δ (ppm) −132.9, 130.0, 128.2, 127.8, 122.6).

Synthesis of Intermediate B 14.3 g (50 mmol) of Intermediate A was dissolved in 150 ml diethyl ether, and held at −78° C. while adding 20 ml (2.5M in hexane) of normal butyl lithium. The temperature was slowly raised to room temperature after 30 minutes. After 30 minutes, a solution of 23 ml of triisopropylborate (100 mmol) dissolved in 50 ml of diethyl ether was maintained at −78° C. and slowly added to the Intermediate A solution. The mixture was stirred for 5 hours at room temperature, water was added thereto, and the mixture was washed with 200 ml of diethyl ether 3 times. The washed diethyl ether layer was dried with MgSO$_4$, and dried under reduced pressure to obtain a product, which was recrystallized with normal hexane to obtain 9.6 g of Intermediate B, a white solid (yield 77%). The structure of the product was confirmed by $^1$H and $^{13}$C NMR. ($^1$H NMR (CDCl$_3$, 400 MHz) δ (ppm) −8.05 (d, 1H), 7.85 (d, 1H), 7.73 (m, 4H), 7.35 (s, 2H); $^{13}$C NMR (CDCl$_3$, 100 MHz) δ (ppm) −141.4, 131.0, 130.8, 130.4, 130.1, 127.0, 126.2, 102.2, 101.0).

Synthesis of Intermediate C 7.53 g (30 mmol) of Intermediate B, 17 g (60 mmol) of 4-bromoiodobenzene, 1.7 g (1.5 mmol) of Pd(PPh$_3$)$_4$ and 20 g of K$_2$CO$_3$ were dissolved in 100 ml of a THF/H$_2$O (2:1) mixed solution, and then stirred for 5 hours at 80° C. The reaction solution was extracted 3 times with 600 ml of diethyl ether. The collected organic layer was dried with magnesium sulfate, and the residue obtained by evaporating the solvent was recrystallized with dichloromethane and normal hexane to obtain 7.38 g of Intermediate C (yield: 68%). The structure of the product was confirmed by $^1$H NMR. ($^1$H NMR (CDCl$_3$, 400 MHz) δ (ppm) −8.32 (d, 1H), 7.83-7.80 (m, 2H), 7.63-7.59 (m, 3H), 7.51-7.46 (m, 1H), 7.32 (d, 2H), 7.22 (d, 1H)).

Synthesis of Intermediate D 36.9 g (100 mmol) of 3-iodo-9-phenylcarbazole, 13.7 mL (150 mmol) of aniline, 14 g (150 mmol) of t-BuONa, 1.83 g (2 mmol) of Pd$_2$(dba)$_3$, 400 mg (2 mmol) of P(t-Bu)$_3$ were dissolved in 250 ml of toluene, and then stirred for 3 hours at 90° C. After the reaction was complete, the product was cooled to room temperature, and then extracted 3 times with deionized water and 200 ml of diethyl ether. The collected organic layer was dried with magnesium sulfate, and the residue obtained by evaporating the solvent was separated and purified by silica gel column chromatography to obtain 3.07 g of Intermediate D (yield 92%). The structure of the product was confirmed by $^1$H and $^{13}$C NMR. ($^1$H NMR (CDCl$_3$, 400 MHz) δ (ppm) −8.03-7.99 (m, 1H), 7.67 (d, 1H), 7.49 (d, 5H), 7.43 (d, 1H), 7.36-7.32 (m, 3H), 7.20-7.16 (m, 2H), 7.02 (dd, 2H), 6.96 (dd, 1H), 6.75-6.71 (m, 1H), 5.68 (NH); $^{13}$C NMR (CDCl$_3$, 100 MHz) δ (ppm) −144.7, 139.9, 137.4, 135.7, 129.8, 129.4, 128.1, 127.4, 127.1, 126.3, 119.1, 119.0, 118.7, 118.5, 116.8, 113.1, 111.2, 109.4, 102.5).

Synthesis of Compound 1

3.62 g (10 mmol) of Intermediate C, 7.36 g (22 mmol) of Intermediate D, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 7.13 g of Compound 1 (yield 82%). The structure of the product was confirmed by $^1$H and $^{13}$C NMR. ($^1$H NMR (CDCl$_3$, 400 MHz) δ (ppm) −8.21 (d, 2H), 7.93 (d, 2H), 7.65-7.28 (m, 32H), 6.64-6.59 (m, 2H), 6.43-6.40 (m, 2H), 5.70-5.64 (m, 4H); $^{13}$C NMR (CDCl$_3$, 100 MHz) δ (ppm) −153.3, 151.4, 150.6, 148.3, 146.1, 142.5, 137.9, 137.7, 136.4, 134.8, 133.9, 131.6, 131.4, 129.8, 129.4, 129.2, 128.1, 127.4, 127.1, 126.3, 126.1, 125.9, 124.1, 123.6, 123.4, 122.9, 122.3, 121.3, 120.4, 118.1, 117.3, 117.2, 117.0, 116.7, 116.4, 116.2, 114.4, 111.7, 111.5, 108.4).

SYNTHESIS EXAMPLE 2

Preparation of Compound 2

Compound 2 was synthesized by the reaction pathway represented by Reaction Scheme 2 below.

Reaction Scheme 2

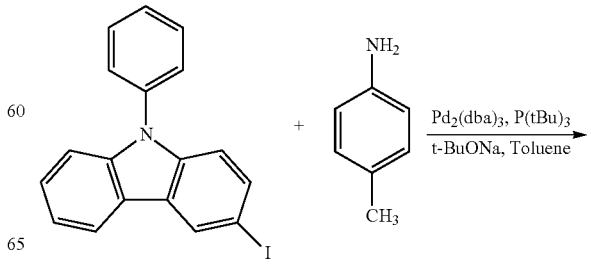

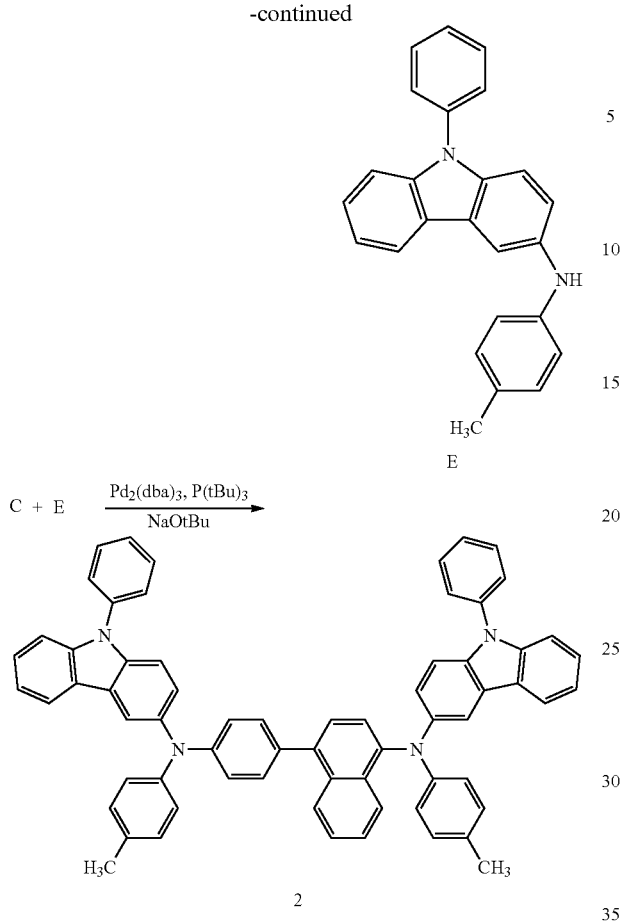

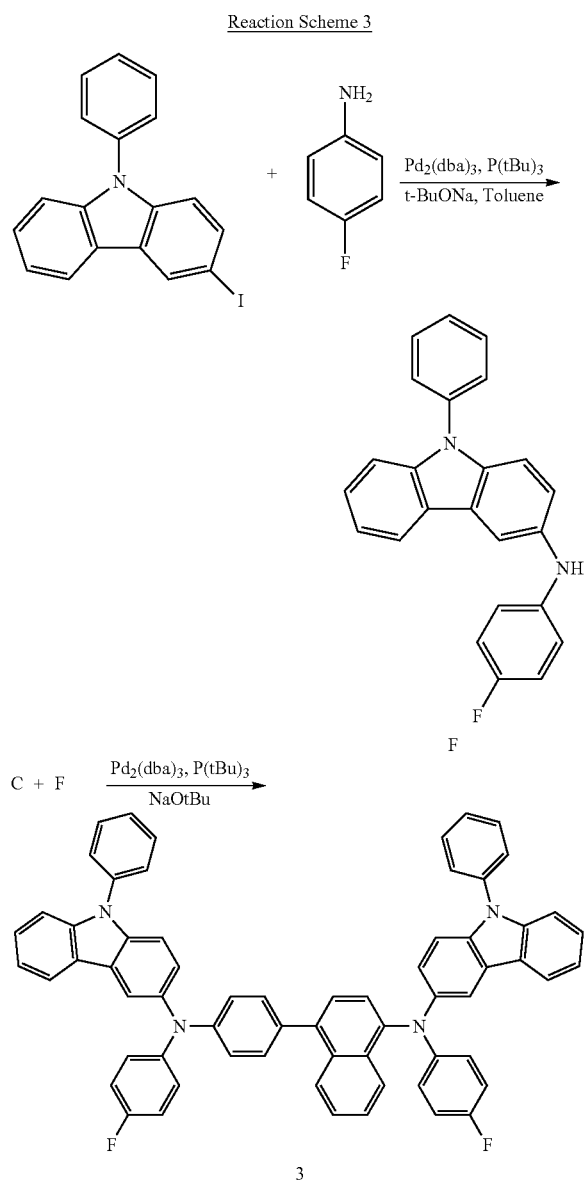

pound 2 (yield: 85%). The structure of the product was confirmed by $^1$H and $^{13}$C NMR. ($^1$H NMR (CDCl$_3$, 400 MHz) δ (ppm) −8.21 (d, 1H), 7.93 (d, 2H), 7.63-7.31 (m, 29H), 7.05 (dd, 4H), 6.42 (d, 2H), 6.25 (t, 4H), 2.27 (s, 6H); $^{13}$C NMR (CDCl$_3$, 100 MHz) δ (ppm) −153.3, 151.4, 151.3, 147.8, 146.1, 142.5, 137.9, 137.7, 136.4, 134.8, 134.6, 133.9, 132.7, 131.4, 129.8, 129.2, 128.1, 127.4, 127.1, 126.3, 126.1, 125.9, 124.1, 123.6, 122.3, 121.2, 121.0, 120.4, 118.1, 117.3, 117.0, 116.7, 116.4, 116.2, 111.7, 114.4, 111.7, 111.5, 108.4, 20.4).

SYNTHESIS EXAMPLE 3

Preparation of Compound 3

Compound 3 was synthesized by the reaction pathway represented by Reaction Scheme 3 below.

Synthesis of Intermediate E 36.9 g (100 mmol) of 3-iodo-9-phenylcarbazole, 16 g (150 mmol) of toluidine, 14 g (150 mmol) of t-BuONa, 1.83 g (2 mmol) of Pd$_2$(dba)$_3$, and 400 mg (2 mmol) of P(t-Bu)$_3$ were dissolved in 250 ml of toluene, and stirred for 3 hours at 90° C. After the reaction was complete, the product was cooled to room temperature, and then extracted 3 times with deionized water and 200 ml of diethyl ether. The collected organic layer was dried with magnesium sulfate, and the residue obtained by evaporating the solvent was separated and purified by silica gel column chromatography to obtain 33.5 g of Intermediate E (yield: 96%). The structure of the product was confirmed by $^1$H and $^{13}$C NMR. ($^1$H NMR (CDCl$_3$, 400 MHz) δ (ppm) −8.02-7.99 (m, 1H), 7.66 (s, 1H), 7.49 (d, 4H), 7.43 (d, 1H), 7.36-7.31 (m, 4H), 7.01 (d, 2H), 6.96 (dd, 1H), 6.87 (d, 2H), 5.68 (NH), 2.25 (s, 3H); $^{13}$C NMR (CDCl$_3$, 100 MHz) δ (ppm) −140.2, 139.9, 137.4, 135.7, 129.8, 129.7, 128.1, 127.4, 127.1, 126.3, 119.1, 118.7, 118.5, 113.1, 111.2, 109.4, 102.5, 20.4).

Synthesis of Compound 2

3.62 g (10 mmol) of Intermediate C, 7.7 g (22 mmol) of Intermediate E, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 7.62 g of Com- Synthesis of Intermediate F 18.45 g (50 mmol) of 3-iodo-9-phenylcarbazole, 8 g (75 mmol) of toluidine, 7 g (75 mmol) of t-BuONa, 920 mg (1 mmol) of Pd$_2$(dba)$_3$, and 200 mg (1 mmol) of P(t-Bu)$_3$ were dissolved in 150 ml of toluene, and stirred for 3 hours at 90° C. After the reaction was complete, the product was cooled to room temperature, and then extracted 3 times with deionized water and 100 ml of diethyl ether. The collected organic layer was dried with magnesium sulfate, and the residue obtained by evaporating the solvent was separated and purified by silica gel column chromatography to obtain 16.39 g of Intermediate F (yield 93%). The structure of the product was confirmed by $^1$H and $^{13}$C NMR. ($^1$H NMR (CDCl$_3$, 400 MHz) δ (ppm) −8.03-8.01 (m, 1H), 7.96-7.92 (m, 2H), 7.67 (d, 1H), 7.49 (d, 4H), 7.43 (d, 1H), 7.37-7.32 (m, 4H), 7.23-7.18 (m, 2H), 6.95 (dd, 1H), 5.68 (s, 1H); $^{13}$C NMR (CDCl$_3$, 100 MHz) δ (ppm) −161.0, 154.5, 140.8, 139.9, 137.4, 135.7, 129.8, 127.4, 127.1, 126.5, 119.1, 118.7, 118.5, 116.5, 115.8, 113.1, 111.7, 111.5, 111.2, 109.4, 102.5).

Synthesis of Compound 3

3.62 g (10 mmol) of Intermediate C, 7.75 g (22 mmol) of Intermediate F, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 7.96 g of Compound 3 (yield: 88%). The structure of the product was confirmed by $^1$H and $^{13}$C NMR. ($^1$H NMR (CDCl$_3$, 400 MHz) δ (ppm) −8.21 (d, 1H), 7.93 (d, 2H), 7.65-7.31 (m, 29H), 7.11-7.05 (m, 4H), 6.79-6.73 (m, 4H), 6.44-6.40 (m, 2H); $^{13}$C NMR (CDCl$_3$, 100 MHz) δ (ppm) −162.0, 155.5, 152.3, 150.4, 149.3, 149.2, 145.1, 144.2, 144.1, 141.5, 137.9, 137.7, 136.4, 134.8, 133.9, 131.4, 129.8, 129.2, 128.1, 127.4, 127.1, 126.3, 126.1, 126.0, 125.9, 125.8, 125.6, 124.1, 123.6, 122.3, 121.3, 120.4, 118.1, 118.0, 117.3, 117.2, 117.0, 116.7, 116.4, 116.2, 115.5, 114.4, 111.7, 111.5, 108.4).

SYNTHESIS EXAMPLE 4

Preparation of Compound 32

Compound 32 was synthesized by the reaction pathway represented by Reaction Scheme 4 below.

Reaction Scheme 4

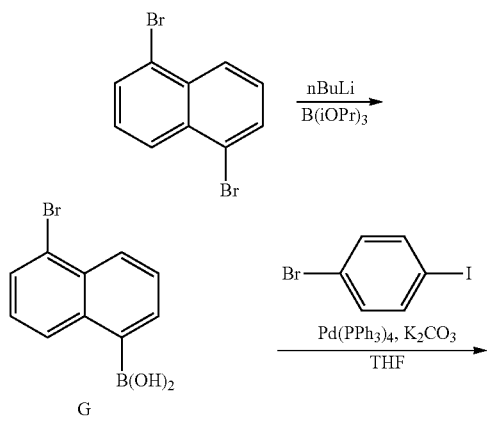

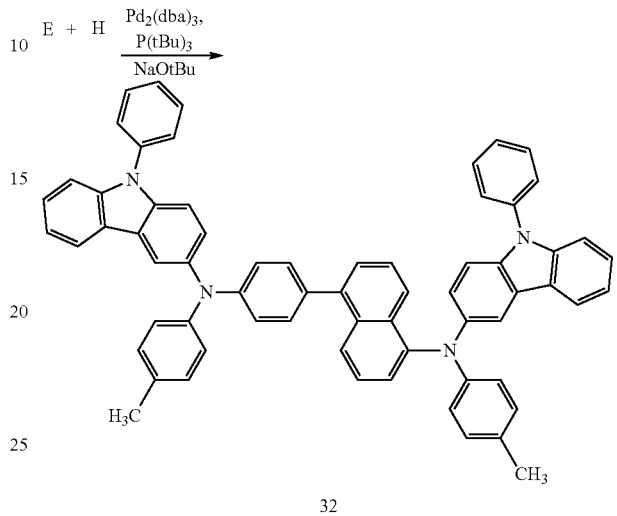

Synthesis of Intermediate G 14.3 g (50 mmol) of 1,5-dibromonaphthalene was dissolved in 150 ml of diethyl ether, and held at −78° C. while adding normal butyl lithium (20 ml, 2.5 M in hexane). The temperature was raised slowly to room temperature after 30 minutes. After another 30 minutes, a solution of 23 ml (100 mmol) triisopropyl borate dissolved in 50 ml of diethyl ether was maintained at −78° C., and the solution of 1,5-dibromonaphthalene was slowly added thereto. The mixture was stirred for 5 hours at room temperature, and water was added thereto. The mixture was washed three times with diethyl ether (200 ml). The washed diethyl ether layer was dried with MgSO$_4$, and was dried under reduced pressure to obtain a product, which was recrystallized with normal hexane to obtain 9.15 g (yield: 88%) of white solid Intermediate G (yield: 88%). The structure of the product was confirmed by $^1$H and $^{13}$C NMR. ($^1$H NMR (CDCl$_3$, 400 MHz) δ (ppm) −8.06-8.01 (m, 2H), 7.85 (dd, 1H), 7.65 (dd, 1H), 7.52-7.48 (t, 1H), 7.35 (s, 1H), 7.20 (t, 1H); $^{13}$C NMR (CDCl$_3$, 100 MHz) δ (ppm) −141.4, 138.6, 138.1, 137.7, 137.2, 130.8, 130.6, 130.4, 129.8, 129.7, 126.2, 101.0).

Synthesis of Intermediate H 7.53 g (30 mmol) of Intermediate G, 17 g (60 mmol) of 4-bromoiodobenzene, 1.7 g (1.5 mmol) of Pd(PPh$_3$)$_4$ and 20 g (150 mmol) of K$_2$CO$_3$ were dissolved in 100 ml of a THF/H$_2$O (2:1) mixed solution, and stirred for 5 hours at 80° C. The reactant solution was extracted three times with 600 ml of diethyl ether. The collected organic layer was dried with magnesium sulfate, and the residue obtained by evaporating the solvent was recrystallized with dichloromethane and normal hexane to obtain 7.06 of Intermediate H (yield: 65%). The structure of the product was confirmed by $^1$H and $^{13}$C NMR. ($^1$H NMR (CDCl$_3$, 400 MHz) δ (ppm) −8.14 (d, 1H), 7.94 (dd, 1H), 7.79 (dd, 1H), 7.66 (d, 1H), 7.45 (t, 1H), 7.28-7.20 (m, 5H); $^{13}$C NMR (CDCl$_3$, 100 MHz) δ (ppm) −139.1, 136.8, 133.2, 132.8, 132.1, 131.4, 130.4, 128.4, 127.8, 127.2, 126.3, 125.0, 123.5).

Synthesis of Compound 32

7.66 g (22 mmol) of Intermediate E, 3.62 g (10 mmol) of Intermediate H, 2.9 mg (30 mmol) of t-BuONa, 183 mg (0.2 mmol) of Pd$_2$(dba)$_3$, and 40 mg (0.2 mmol) of P(t-Bu)$_3$ were dissolved in 40 ml of toluene, and stirred for 3 hours at 90° C. After the reaction was complete, the product was cooled to room temperature, and then extracted 3 times with deionized water and 40 ml of diethyl ether. The collected organic layer was dried with magnesium sulfate, and the residue obtained by evaporating the solvent was separated and purified by silica gel column chromatography to obtain 7.62 g of Compound 32 (yield 85%). The structure of the product was confirmed by $^1$H and $^{13}$C NMR. ($^1$H NMR (CDCl$_3$, 400 MHz) δ (ppm) –8.52 (d, 1H), 8.19 (d, 1H), 7.93 (d, 2H), 7.66-7.42 (m, 23H), 7.36-7.32 (m, 4H), 7.05 (d, 4H), 6.42 (d, 2H), 6.25 (t, 4H) 6.17 (s, 1H), 2.27 (s, 6H); $^{13}$C NMR (CDCl$_3$, 100 MHz) δ (ppm) –153.3, 151.4, 151.3, 149.8, 146.1, 142.5, 137.8, 137.7, 136.4, 134.8, 134.6, 133.9, 132.7, 131.4, 129.8, 129.7, 129.2, 128.7, 127.4, 127.1, 126.3, 123.6, 122.6, 122.3, 121.2, 121.0, 120.4, 118.1, 117.9, 117.3, 116.9, 116.7, 116.3, 116.2, 114.4, 111.9, 111.7, 111.5, 20.4).

SYNTHESIS EXAMPLE 5

Preparation of Compound 105

Compound 105 was synthesized through the reaction pathway represented by Reaction Scheme 5 below.

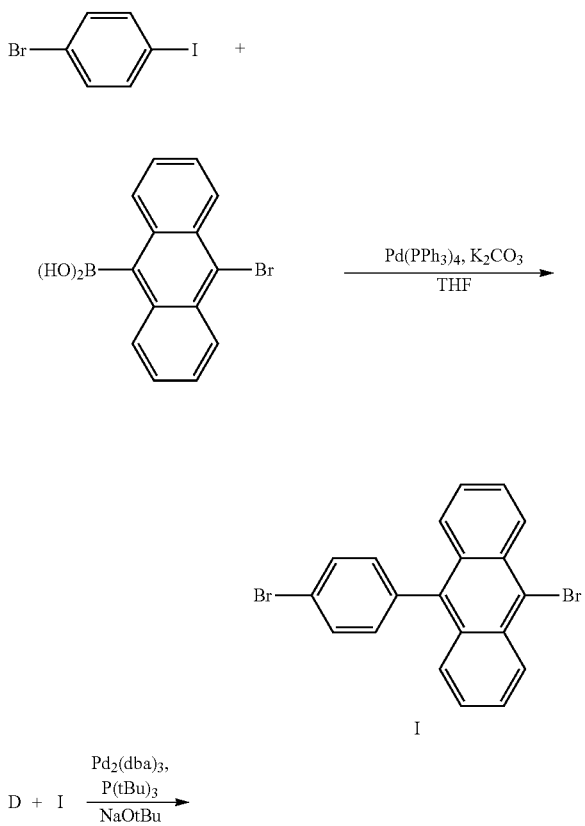

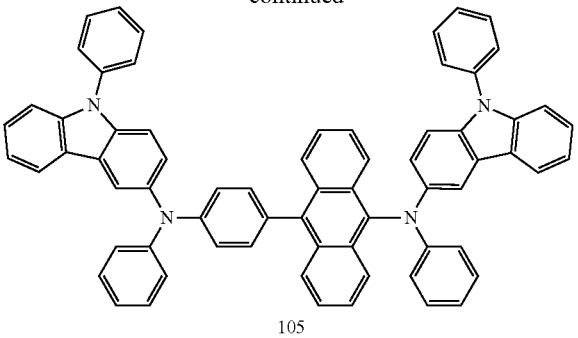

105

Synthesis of Intermediate I 3 g (10 mmol) of 9-bromoanthracene-10-boric acid, 4.24 g (15 mmol) of 4-bromoiodobenzene, 580 mg (0.5 mmol) of Pd(PPh$_3$)$_4$, and 6.9 g (50 mmol) of K$_2$CO$_3$ were dissolved in 50 ml of a THF/H$_2$O (2:1) mixed solution, and stirred for 5 hours at 80° C. The reactant solution was extracted 3 times with 50 ml of diethyl ether. The collected organic layer was dried with magnesium sulfate, and the residue obtained by evaporating the solvent was recrystallized with dichloromethane and normal hexane to obtain 2.47 g of Intermediate I (yield: 60%). The structure of the product was confirmed by $^1$H and $^{13}$C NMR. ($^1$H NMR (CDCl$_3$, 400 MHz) δ (ppm) –8.61 (d, 2H), 7.72 (d, 2H), 7.62-7.57 (m, 4H), 7.41-7.37 (m, 2H), 7.29-7.25 (m, 2H); $^{13}$C NMR (CDCl$_3$, 100 MHz) δ (ppm) –137.3, 136.2, 132.8, 131.7, 130.8, 130.2, 128.0, 127.0, 125.8, 123.2, 122.1).

Synthesis of Compound 105

2.06 g (5 mmol) of Intermediate I, 3.68 g (11 mol) of Intermediate C, 1.44 g (15 mmol) of t-BuONA, 183 mg (0.2 mmol) of Pd$_2$(dba)$_3$, and 40 mg (0.2 mmol) of P(t-Bu)$_3$ were dissolved in 40 ml of toluene, and stirred for 3 hours at 90° C. After the reaction was complete, the product was cooled to room temperature, and then extracted 3 times with deionized water and 40 ml of diethyl ether. The collected organic layer was dried with magnesium sulfate, and the residue obtained by evaporating the solvent was separated and purified by silica gel column chromatography to obtain 3.9 g of Compound 105 (yield: 85%). The structure of the product was confirmed by $^1$H and $^{13}$C NMR. ($^1$H NMR (CDCl$_3$, 400 MHz) δ (ppm) –8.55 (d, 2H), 8.04 (d, 2H), 7.93 (d, 2H), 7.63-7.23 (m, 32H), 6.64-6.59 (m, 2H), 6.41-6.38 (m, 2H), 5.69 (dd, 2H), 5.64 (dd, 2H); $^{13}$C NMR (CDCl$_3$, 100 MHz) δ (ppm) –154.1, 153.2, 149.8, 148.3, 142.5, 137.9, 137.7, 137.6, 136.7, 136.4, 133.4, 133.2, 131.7, 130.7, 129.8, 129.4, 127.4, 127.1, 126.3, 126.2, 124.6, 124.3, 124.1, 123.6, 123.4, 123.2, 122.9, 121.7, 120.4, 118.1, 117.5, 117.4, 117.0, 116.8, 114.4, 111.9, 111.5, 108.4).

SYNTHESIS EXAMPLE 6

Preparation of Compound 153

Compound 153 was synthesized through the reaction pathway represented by Reaction Scheme 6 below.

Reaction Scheme 6

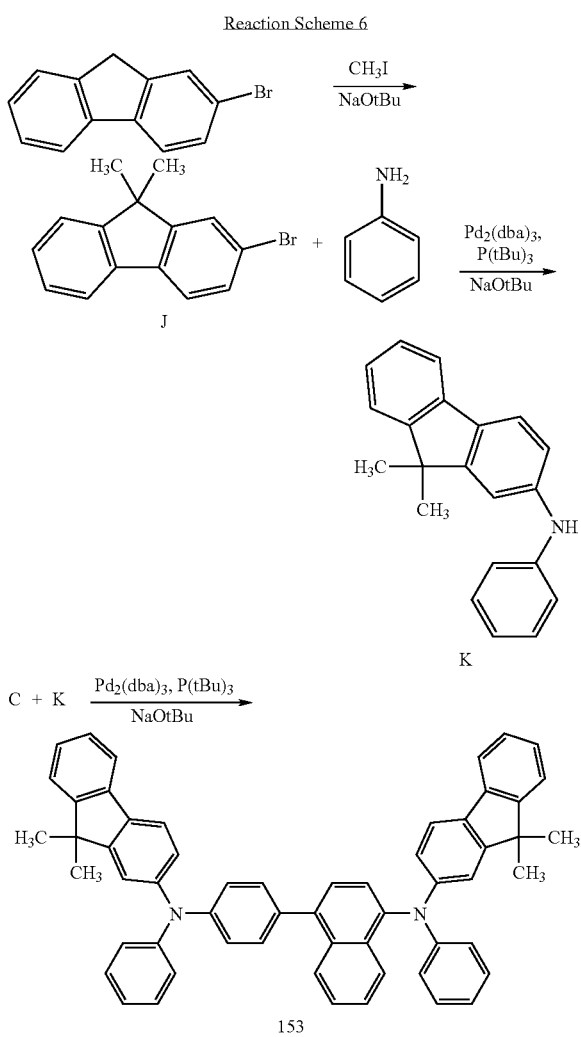

Synthesis of Intermediate J 27.3 g (100 mmol) of 1-bromofluorene was dissolved in 300 ml of tetrahydrofuran, and maintained at 0° C. 31.4 g (110 mmol) of NaOtBu was slowly added to the solution, and 14 ml (220 mmol) of iodomethane was added at the same temperature. After the addition, the mixture was incubated for 5 hours at room temperature. After the reaction was complete, an aqueous solution was added to the solution to extract the organic layer. The collected organic layer was dried with magnesium sulfate, and the residue obtained by evaporating the solvent was separated and purified by silica gel column chromatography to obtain 24.6 g of Intermediate J (yield 90%). The structure of the product was confirmed by $^1$H and $^{13}$C NMR. ($^1$H NMR (CDCl$_3$, 400 MHz) δ (ppm) −7.88 (d, 1H), 7.73 (d, 1H), 7.58 (d, 1H), 7.49-7.46 (m, 1H), 7.40 (d, 1H), 7.24-7.20 (m, 1H), 6.97-6.93 (m, 1H), 1.85 (s, 6H); $^{13}$C NMR (CDCl$_3$, 100 MHz) δ (ppm) −151.6, 150.2, 142.6, 141.1, 132.2, 129.2, 127.8, 127.3, 126.8, 121.2, 119.9, 48.4, 24.5).

Synthesis of Intermediate K 8.2 g (30 mmol) of Intermediate J, 4.1 mL (45 mmol) of aniline, 4.3 g (45 mmol) of t-BuONa, 0.55 g (0.6 mmol) of Pd$_2$(dba)$_3$, and 0.12 g (0.6 mmol) of P(t-Bu)$_3$ were dissolved in 100 ml of toluene, and stirred for 3 hours at 90° C. After the reaction was complete, the product was cooled to room temperature, and then extracted 3 times with deionized water and 100 ml of diethyl ether. The collected organic layer was dried with magnesium sulfate, and the residue obtained by evaporating the solvent was separated and purified by silica gel column chromatography to obtain 7.87 g of Intermediate K (yield: 92%). The structure of the product was confirmed by $^1$H and $^{13}$C NMR. ($^1$H NMR (CDCl$_3$, 400 MHz) δ (ppm) −7.82 (d, 1H), 7.54-7.49 (m, 2H), 7.27-7.21 (m, 3H), 7.12-7.08 (m, 3H), 6.97-6.93 (m, 1H), 6.90-6.86 (m, 1H), 6.59-6.56 (m, 1H), 5.44(NH), 1.85(s, 6H); $^{13}$C NMR (CDCl$_3$, 100 MHz) δ (ppm) −149.1, 146.8, 142.2, 140.0, 134.6, 133.5, 129.4, 127.8, 127.1, 126.8, 120.4, 119.7, 119.1, 117.4, 109.0, 107.5, 44.9, 24.5).

Synthesis of Compound 153

3.62 g (10 mmol) of Intermediate C, 6.28 g (22 mmol) of Intermediate K, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 6.55 g of Compound 153 (yield: 85%). The structure of the product was confirmed by $^1$H and $^{13}$C NMR. ($^1$H NMR (CDCl$_3$, 400 MHz) δ (ppm) −8.19 (d, 2H), 7.98 (d, 1H), 7.69-7.57 (m, 5H), 7.49-7.08 (m, 14H), 6.97-6.93 (m, 2H), 6.64-6.60 (m, 2H), 6.43-6.39 (m, 2H), 6.34-6.32 (m, 2H), 5.68-5.61 (m, 4H), 1.85 (s, 6H), 1.77 (s, 6H); $^{13}$C NMR (CDCl$_3$, 100 MHz) δ (ppm) −158.4, 154.5, 150.4, 148.9, 148.1, 147.9, 147.1, 145.8, 141.3, 140.9, 139.0, 138.0, 136.5, 134.8, 133.9, 131.6, 130.9, 130.8, 129.4, 129.2, 128.1, 127.8, 126.8, 126.5, 126.1, 125.9, 125.6, 124.7, 124.1, 124.0, 123.6, 123.2, 122.9, 121.7, 119.9, 118.7, 117.9, 117.8, 117.4, 117.3, 116.7, 45.3, 44.9, 25.3, 24.5).

SYNTHESIS EXAMPLE 7

Preparation of Compound 173

Compound 173 was synthesized through the reaction pathway represented by Reaction Scheme 7 below.

Reaction scheme 7

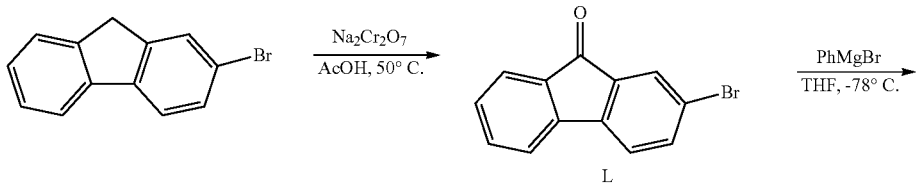

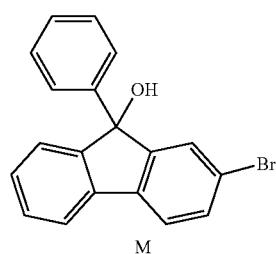 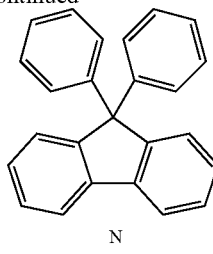 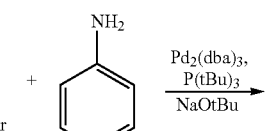

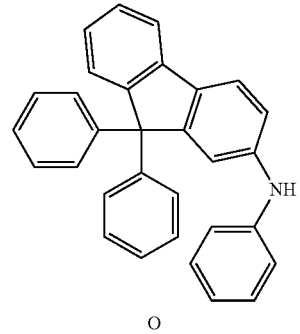

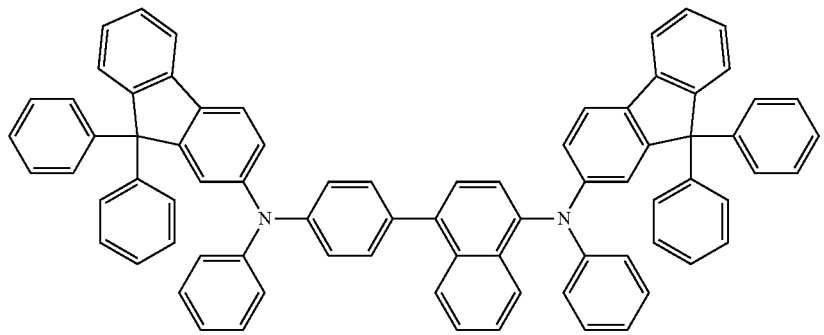

Synthesis of Intermediate L 13 g (53 mmol) of 2-bromofluorene was dissolved in 60 ml of acetic acid, and 60 g (200 mmol) of sodium dichromate was slowly added to the solution at 0° C. After 12 hours, 200 ml of deionized water was added to the mixture, and stirred thoroughly. The resulting yellow solid product was filtered and dried to obtain 10 g of Intermediate L (yield: 78%).

Synthesis of Intermediate M 8 g (31.6 mmol) of Intermediate L was dissolved in 60 ml of THF, and 38 ml (38 mmol) of 1M phenyl magnesium bromide was slowly added to the solution at −78° C. After 2 hours, the temperature was raised to room temperature, and the mixture was stirred for 5 hours. The mixture was diluted with 50 ml ammonium chloride solution, and extracted 3 times with ethyl acetate (40 ml). The collected organic layer was dried with magnesium sulfate, and the residue obtained by evaporating the solvent was separated and purified by silica gel column chromatography to obtain 10 g of Intermediate M (yield: 95%). The structure was confirmed by $^1$H NMR. ($^1$H NMR (CDCl$_3$, 400 MHz) δ (ppm) 7.64 (d, 1H), 7.54-7.47 (m, 2H), 7.44 (d, 1H), 7.39-7.33 (m, 3H), 7.30-7.23 (m, 5H), 2.46 (s, 1H)).

Synthesis of Intermediate N 10 g (30 mmol) of Intermediate M was dissolved in 60 ml of benzene, and 2.4 ml (45 mmol) of concentrated sulfuric acid diluted with a small amount of benzene was added to the solution. The mixture was stirred for 5 hours at 80° C., and after evaporating the benzene, 1 N sodium hydroxide solution was added to the remaining solution to a pH of around 7. The mixture was extracted 3 times with ethyl acetate (40 ml). The collected organic layer was dried with magnesium sulfate, and the residue obtained by evaporating the solvent was separated and purified by silica gel column chromatography to obtain 6 g of Intermediate N (yield: 50%).

Synthesis of Intermediate O 3.97 g (10 mmol) of Intermediate N, 1.37 ml (15 mmol) of aniline, 1.4 g (15 mmol) of t-BuONa, 0.183 g (0.2 mmol) of Pd$_2$(dba)$_3$, and 40 mg (0.2 mmol) of P(t-Bu)$_3$ were dissolved in 30 ml of toluene, and stirred for 3 hours at 90° C. After the reaction was complete, the product was cooled to room temperature, and then extracted 3 times with deionized water and 30 ml of diethyl ether. The collected organic layer was dried with magnesium sulfate, and the residue obtained by evaporating the solvent was separated and purified by silica gel column chromatography to obtain 3.68 g of Intermediate O (yield: 90%). The structure of the product was confirmed by $^1$H and $^{13}$C NMR. ($^1$H NMR (CDCl$_3$, 400 MHz) δ (ppm) −8.05 (d, 1H), 7.90 (d, 1H), 7.69 (d, 1H), 7.58 (d, 1H), 7.48-7.46 (m, 4H), 7.35-7.31 (m, 1H), 7.27-6.98 (m, 10H), 6.90-6.86 (m, 1H), 6.69-6.67 (m, 2H), 5.44(NH); $^{13}$C NMR (CDCl$_3$, 100 MHz) δ (ppm) −150.0, 147.7, 141.8, 141.2, 137.7, 135.8, 134.6, 130.2, 129.4, 128.7, 128.1, 128.0, 126.0, 125.1, 120.8, 119.1, 117.4, 108.7, 108.4, 68.3).

Synthesis of Compound 173

3.62 g (10 mmol) of Intermediate C, 9.0 g (22 mmol) of Intermediate O, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and were stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 7.95 g of Compound 173 (yield: 78%). The structure of the product was confirmed by $^1$H and $^{13}$C NMR. ($^1$H NMR (CDCl$_3$, 400 MHz) δ (ppm) −8.21 (m, 2H), 8.06 (d, 2H), 7.74-7.60 (m, 10H), 7.53-6.98 (m, 28H), 6.64-6.60 (m, 4H), 6.45-6.38 (m, 4H), 5.68-5.64 (m, 4H); $^{13}$C NMR (CDCl$_3$, 100 MHz) δ (ppm) −152.7, 150.9, 150.4, 149.1, 149.0, 148.5, 148.0, 147.6, 145.3, 139.3, 137.8, 135.7, 134.5, 133.9, 131.6, 131.4, 129.4, 129.2, 128.7, 128.1, 127.0, 126.1, 126.0, 125.9, 125.1, 124.8, 124.7, 124.2, 124.0, 123.6, 122.9, 122.8, 121.3, 119.8, 117.9, 117.7, 117.5, 117.1, 113.8, 113.6).

SYNTHESIS EXAMPLE 8

Preparation of Compound 184

Compound 184 was synthesized through the reaction pathway represented by Reaction Scheme 8 below.

Reaction Scheme 8

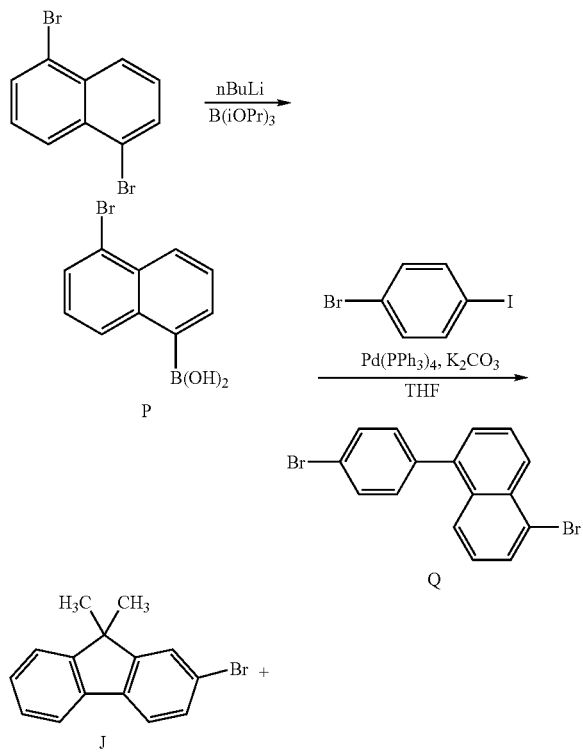

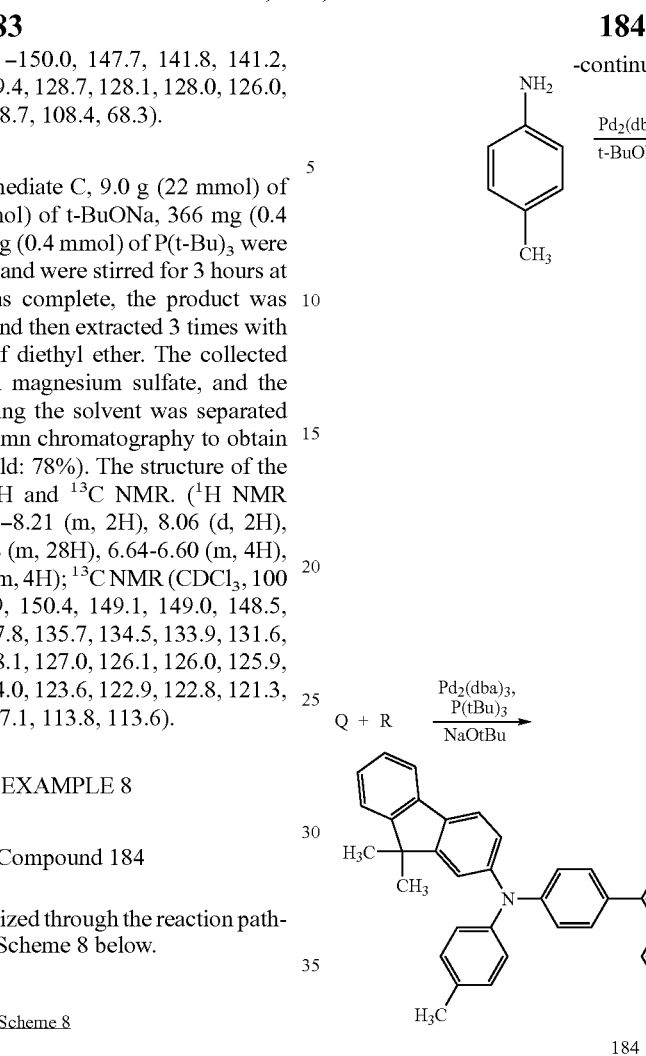

Synthesis of Intermediate P 14.3 g (50 mmol) of 1,5-dibromonaphthalene was dissolved in 150 ml diethyl ether, and held at −78° C. while adding 20 ml (2.5M in hexane) of normal butyl lithium. The temperature was slowly raised to room temperature after 30 minutes. After another 30 minutes, a solution of 23 ml of triisopropylborate (100 mmol) dissolved in 50 ml of diethyl ether was maintained at −78° C. and slowly added to the 1,5-dibromonaphthalene solution. The mixture was stirred for 5 hours at room temperature, and water was added thereto. The mixture was then washed with 200 ml of diethyl ether 3 times. The washed diethyl ether layer was dried with MgSO$_4$, and dried under reduced pressure to obtain a product which was recrystallized with normal hexane to obtain 9.15 g of white solid Intermediate P (yield 73%). The product was confirmed by $^1$H and $^{13}$C NMR. ($^1$H NMR (CDCl$_3$, 400 MHz) δ (ppm) −8.06-8.00 (m, 2H), 7.85 (dd, 1H), 7.65 (dd, 1H), 7.52-7.48 (t, 1H), 7.35 (s, OH), 7.20 (t, 1H); $^{13}$C NMR (CDCl$_3$, 100 MHz) δ (ppm) −141.4, 140.1, 139.6, 139.4, 138.6, 138.4, 137.9, 137.3, 137.1, 136.4, 136.2, 135.6, 130.8, 130.6, 130.4, 129.8, 129.7, 126.2, 101.0).

Synthesis of Intermediate Q 7.53 g (30 mmol) of Intermediate P, 17 g (60 mmol) of 4-bromoiodobenzene, 1.7 g (1.5 mmol) of Pd(PPh$_3$)$_4$ and 20 g of K$_2$CO$_3$ were dissolved in 100 ml of a THF/H$_2$O (2:1) mixed solution, and then stirred for 5 hours at 80° C. The reaction solution was extracted 3 times with 600 ml of diethyl ether. The collected organic layer was dried with magnesium sulfate, and the residue obtained by evaporating the solvent was recrystallized with dichloromethane and normal hexane to obtain 7.06 g of Intermediate Q (yield: 65%). The product was confirmed by $^1$H and $^{13}$C NMR. ($^1$H NMR (CDCl$_3$, 400 MHz) δ (ppm) –8.14 (d, 1H), 7.94 (dd, 1H), 7.79 (dd, 1H), 7.66 (d, 1H), 7.45 (t, 1H), 7.28-7.20 (m, 5H); $^{13}$C NMR (CDCl$_3$, 100 MHz) δ (ppm) –139.1, 136.8, 133.2, 132.8, 132.1, 131.4, 130.4, 128.4, 127.8, 127.2, 126.3, 125.0, 123.5).

Synthesis of Intermediate R 2.73 g (10 mmol) of Intermediate C, 1.65 ml (15 mmol) of para-toluidine, 14 g (15 mmol) of t-BuONa, 183 mg (0.2 mmol) of Pd$_2$(dba)$_3$, and 40 mg (0.2 mmol) of P(t-Bu)$_3$ were dissolved in 30 ml of toluene, and stirred for 3 hours at 90° C. After the reaction was complete, the product was cooled to room temperature, and then extracted 3 times with deionized water and 30 ml of diethyl ether. The collected organic layer was dried with magnesium sulfate, and the residue obtained by evaporating the solvent was separated and purified by silica gel column chromatography to obtain 2.84 g of Intermediate R (yield: 95%). The product was confirmed by $^1$H and $^{13}$C NMR. ($^1$H NMR (CDCl$_3$, 400 MHz) δ (ppm) –7.83-7.81 (m, 1H), 7.54-7.49 (m, 2H), 7.24-7.21 (m, 1H), 7.12 (d, 1H), 7.02-6.93 (m, 3H), 6.87 (d, 2H), 6.58 (dd, 2H), 5.44 (NH), 2.25 (s, 3H), 1.85 (s, 6H); $^{13}$C NMR (CDCl$_3$, 100 MHz) δ (ppm) –149.1, 146.8, 140.0, 137.7, 134.6, 133.5, 129.7, 127.8, 127.1, 126.8, 120.4, 119.7, 119.3, 109.0, 107.5, 44.9, 24.5, 20.4).

Synthesis of Compound 184

3.62 g (10 mmol) of Intermediate Q, 6.59 g (22 mmol) of Intermediate R, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 7.03 g of Compound 184 (yield 88%). The product was confirmed by $^1$H and $^{13}$C NMR. ($^1$H NMR (CDCl$_3$, 400 MHz) δ (ppm) –8.51 (d, 1H), 8.19 (d, 1H), 7.98 (d, 2H), 7.69-7.44 (m, 9H), 7.24-6.93 (m, 10H), 6.43-6.15 (m, 9H), 2.27 (s, 6H), 1.85 (s, 12H); $^{13}$C NMR (CDCl$_3$, 100 MHz) δ (ppm) –151.6, 150.8, 150.0, 149.0, 148.9, 148.1, 147.9, 147.1, 145.4, 138.0, 136.5, 134.8, 134.6, 133.9, 132.7, 131.4, 129.7, 129.2, 128.7, 127.8, 126.8, 126.1, 123.6, 123.5, 122.6, 121.9, 121.7, 121.3, 120.4, 118.7, 118.0, 117.9, 117.8, 116.9, 112.9, 112.7, 44.9, 24.5, 20.4).

SYNTHESIS EXAMPLE 9

Preparation of Compound 213

Compound 213 was synthesized through the reaction pathway represented by Reaction Scheme 9 below.

Reaction Scheme 9

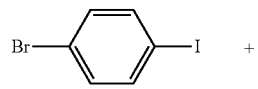

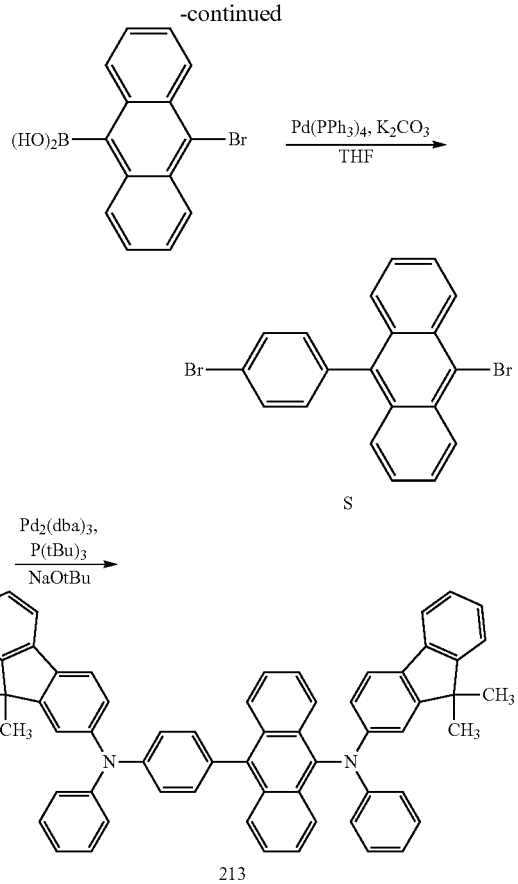

Synthesis of Intermediate S 3 g (10 mmol) of 9-bromoanthracene-10-boric acid, 4.24 g (15 mmol) of 4-bromoiodobenzene, 580 mg (0.5 mmol) of Pd(PPh$_3$)$_4$, and 6.9 g (50 mmol) of K$_2$CO3 were dissolved in 50 ml of a THF/H$_2$O (2:1) mixed solution, and stirred for 5 hours at 80° C. The reactant solution was extracted 3 times with 50 ml of diethyl ether. The collected organic layer was dried with magnesium sulfate, and the residue obtained by evaporating the solvent was recrystallized with dichloromethane and normal hexane to obtain 2.47 g of Intermediate S (yield: 60%). The product was confirmed by $^1$H and $^{13}$C NMR. ($^1$H NMR (CDCl$_3$, 400 MHz) δ (ppm) –8.61 (d, 2H), 7.72 (d, 2H), 7.62-7.57 (m, 4H), 7.41-7.37 (m, 2H), 7.29-7.25 (m, 2H); $^{13}$C NMR (CDCl$_3$, 100 MHz) δ (ppm) –137.3 136.2, 132.8, 131.7, 130.8, 130.2, 128.0, 127.0, 125.8, 123.2, 122.1).

Synthesis of Compound 213

4.12 g (10 mmol) of Intermediate S, 6.28 g (22 mmol) of Intermediate K, 2.9 g (30 mmol) of t-BuONa, 366 mg (0.4 mmol) of Pd$_2$(dba)$_3$, and 80 mg (0.4 mmol) of P(t-Bu)$_3$ were dissolved in 60 ml of toluene, and stirred for 3 hours at 90° C. After the reaction was complete, the product was cooled to room temperature, and then extracted 3 times with deionized water and 50 ml of diethyl ether. The collected organic layer was dried with magnesium sulfate, and the residue obtained by evaporating the solvent was separated and purified by silica gel column chromatography to obtain 5.99 g of Compound 213 (yield: 73%). The product was confirmed by $^1$H and $^{13}$C NMR. ($^1$H NMR (CDCl$_3$, 400 MHz) δ (ppm) –8.55 (d, 2H), 8.01 (dd, 4H), 7.68 (d, 2H), 7.63-7.53 (m, 7H), 7.33-7.21 (m, 7H), 7.15-7.10 (m, 2H), 6.97-6.93 (m, 2H), 6.62 (t, 2H), 6.40-6.27 (m, 4H), 5.68-5.62 (m, 4H), 1.85 (s, 12H); $^{13}$C NMR (CDCl$_3$, 100 MHz) δ (ppm) −155.2, 151.8, 151.7, 150.8, 148.1, 147.9, 147.1, 145.8, 138.0, 137.6, 136.5, 134.3, 133.4, 133.2, 131.7, 130.7, 129.4, 127.8, 126.8, 126.3, 126.2, 126.1, 125.4, 125.0, 124.6, 124.0, 123.6, 123.2, 122.9, 121.7, 118.7, 118.2, 118.1, 117.8, 113.1, 112.7, 44.9, 24.5).

EXAMPLE 1

An anode was prepared by cutting a Corning 15 Ωcm$^2$ (1200 Å) ITO glass substrate to a size of 50 mm×50 mm×0.7 mm, sonicating for 5 minutes using isopropyl alcohol and deionized water, and then irradiating with UV light for 30 minutes and exposing to ozone to clean. Then, the prepared anode was installed on a vacuum deposition apparatus.

Compound 1 was vacuum deposited on the anode to a thickness of 600 Å to form an HIL, and 4,4'-bis[N-(1-naphthyl)-N-phenylamino]biphenyl (NPB) as a hole transporting compound was vacuum deposited on the HIL to a thickness of 300 Å to form a HTL.

Then, a blue fluorescent host (IDE215 from Idemitsu Co.) and a blue fluorescent dopant (IDE118 from Idemitsu Co.) were deposited simultaneously (at a weight ratio of 98:2) on the HTL to form an EML with a thickness of 200 Å.

Next, Alq$_3$ was deposited on the EML to a thickness of 300 Å to form an ETL, and a halogenated alkaline metal LiF was deposited to a thickness of 10 Å on the ETL to form an EIL. Finally, Al was vacuum deposited on the EIL to a thickness of 3000 Å (cathode), thereby completing the manufacture of an organic light emitting device.

The device had a driving voltage of 6.68 V, a high emission brightness of 7,898 cd/m$^2$, color coordinates of (0.144,0.232), and an emission efficiency of 7.9 cd/A, at a current density of 100 mA/cm$^2$,

EXAMPLE 2

An organic light-emitting device was prepared as in Example 1, except that Compound 2 was used instead of Compound 1 when forming the HIL. The device had a driving voltage of 6.72 V, a high emission brightness of 7,733 cd/m$^2$, color coordinates of (0.144,0.236), and an emission efficiency of 7.73cd/A, at a current density of 100 mA/cm$^2$.

EXAMPLE 3

An organic light-emitting device was prepared as in Example 1, except that Compound 3 was used instead of Compound 1 when forming the HIL. The device had a driving voltage of 6.79 V, a high emission brightness of 7,490 cd/m$^2$, color coordinates of (0.143,0.237), and an emission efficiency of 7.49 cd/A, at a current density of 100 mA/cm$^2$.

EXAMPLE 4

An organic light-emitting device was prepared as in Example 1, except that Compound 32 was used instead of Compound 1 when forming the HIL. The device had a driving voltage of 6.64 V, a high emission brightness of 7,289 cd/m$^2$, color coordinates of (0.145,0.241), and an emission efficiency of 7.29 cd/A, at a current density of 100 mA/cm$^2$.

EXAMPLE 5

An organic light-emitting device was prepared as in Example 1, except that Compound 105 was used instead of Compound 1 when forming the HIL. The device had a driving voltage of 6.75 V, a high emission brightness of 7,406 cd/m$^2$, color coordinates of (0.145,0.236), and an emission efficiency of 7.41 cd/A, at a current density of 100 mA/cm$^2$.

EXAMPLE 6

An anode was prepared by cutting a Corning 15 Ωcm$^2$ (1200 Å) ITO glass substrate to a size of 50 mm×50 mm×0.7 mm, sonicating for 5 minutes using isopropyl alcohol and deionized water, and then irradiating with UV light for 30 minutes and exposing to ozone to clean. Then, the prepared anode was installed on a vacuum deposition apparatus.

First, 2-TNATA (shown below) was vacuum deposited on the anode to a thickness of 600 Å to form a HIL, and then Compound 153 was vacuum deposited on the HIL to a thickness of 300 Å to form a HTL.

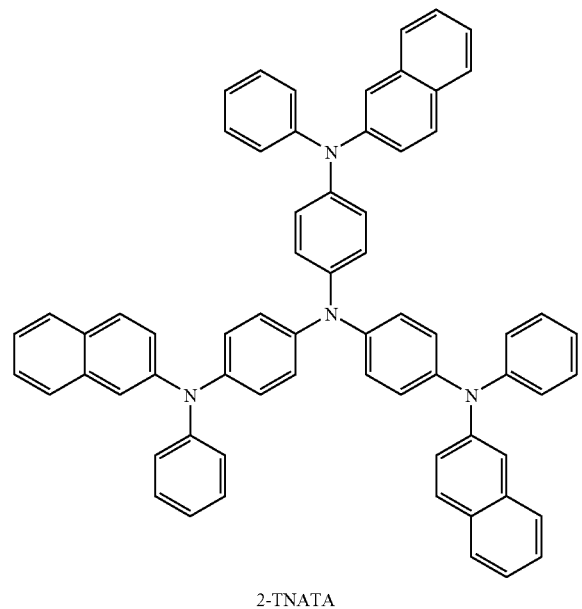 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Then, a blue fluorescent host (IDE215 from Idemitsu Co.) and a blue fluorescent dopant (IDE118 from Idemitsu Co.) were deposited simultaneously (at a weight ratio of 98:2) on the HTL to form an EML with a thickness of 200 Å.

Next, Alq$_3$ was deposited on the EML to a thickness of 300 Å to form an ETL, and a halogenated alkaline metal LiF was deposited on the ETL to a thickness of 10 Å to form an EIL. Finally, Al was vacuum deposited on the EIL to a thickness of 3000 Å (cathode), thereby completing the manufacture of an organic light-emitting device.

The device had a driving voltage of 6.57 V, a high emission brightness of 8,340 cd/m$^2$, color coordinates of (0.144,0.233), and an emission efficiency of 8.34 cd/A, at a current density of 100 mA/cm$^2$.

EXAMPLE 7

An organic light-emitting device was prepared as in Example 6, except that Compound 173 was used instead of Compound 153 when forming the HTL. The device had a driving voltage of 6.72 V, a high emission brightness of 7,950 cd/m$^2$, color coordinates of (0.143,0.231), and an emission efficiency of 7.95 cd/A, at a current density of 100 mA/cm$^2$.

EXAMPLE 8

An organic light emitting device was prepared as in Example 6, except that Compound 184 was used instead of Compound 153 when forming the HTL. The device had a current density of 100 mA/cm$^2$, a driving voltage of 6.83 V, a high emission brightness of 7,890 cd/m$^2$, color coordinates of (0.144,0.229), and an emission efficiency of 7.89 cd/A at a current density of 100 mA/cm$^2$.

EXAMPLE 9

An organic light emitting device was prepared as in Example 6, except that Compound 213 was used instead of Compound 153 when forming the HTL. The device had a driving voltage of 7.05 V, a high emission brightness of 7,896 cd/m$^2$, color coordinates of (0.145,0.234), and an emission efficiency of 7.90 cd/A at a current density of 100 mA/cm$^2$.

COMPARATIVE EXAMPLE 1

An organic light emitting device was prepared as in Example 1, except that a material represented by the structure below was used instead of Compound 1 when forming the HIL.

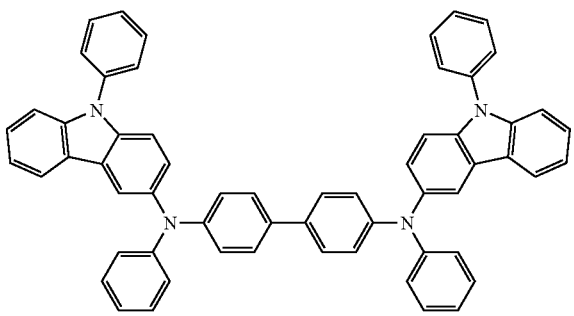 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

The device had a driving voltage of 6.81 V, an emission brightness of 7,134cd/m$^2$, color coordinates of (0.144, 0.237), and an emission efficiency of 7.13 cd/A at a current density of 100 mA/cm$^2$.

COMPARATIVE EXAMPLE 2

An organic light emitting device was prepared as in Example 1, except that 2-TNATA (shown below) was used instead of Compound 1 when forming the HIL.

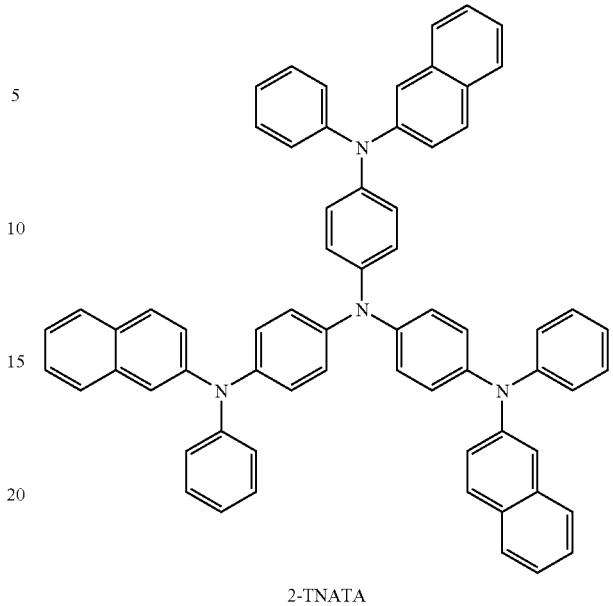

2-TNATA

The device had a driving voltage of 7.45 V, an emission brightness of 6,102 cd/m$^2$, color coordinates of (0.144,0.232), and an emission efficiency of 6.1 cd/A at a current density of 100 mA/cm$^2$.

Figure 2:
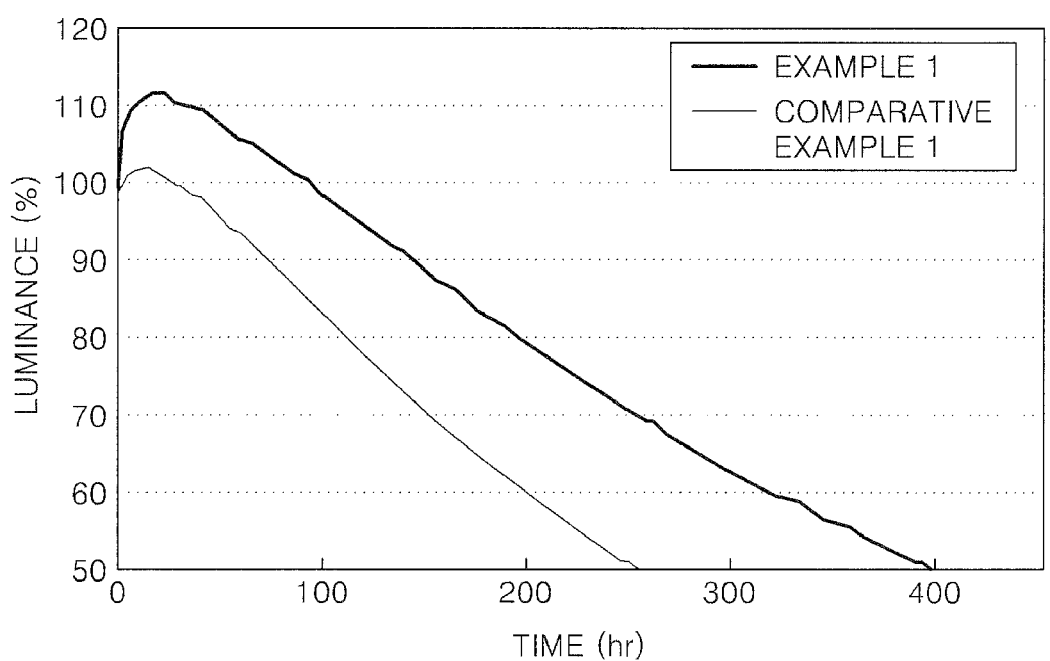
FIG. 2 is a graph comparing the life span of the organic light emitting device prepared according to Example 1 to the life span of the organic light emitting device prepared according to Comparative Example 1.

The compounds represented by Formula 1 according to embodiments of the present invention had superior device properties than the compounds used in the Comparative Examples. In particular, when compared to the compound used in Comparative Example 1 (which had a structure similar to Compound 1, the device prepared with Compound 1 had a lower driving voltage, improved efficiency, and a life span 1.5 times longer (see FIG. 2). This is due to an effect caused by the naphthyl group located in the core structure of Compound 1 (as opposed to a phenyl group), which functions to stabilize the radicals produced during hole injection or transportation.

Figure 3:
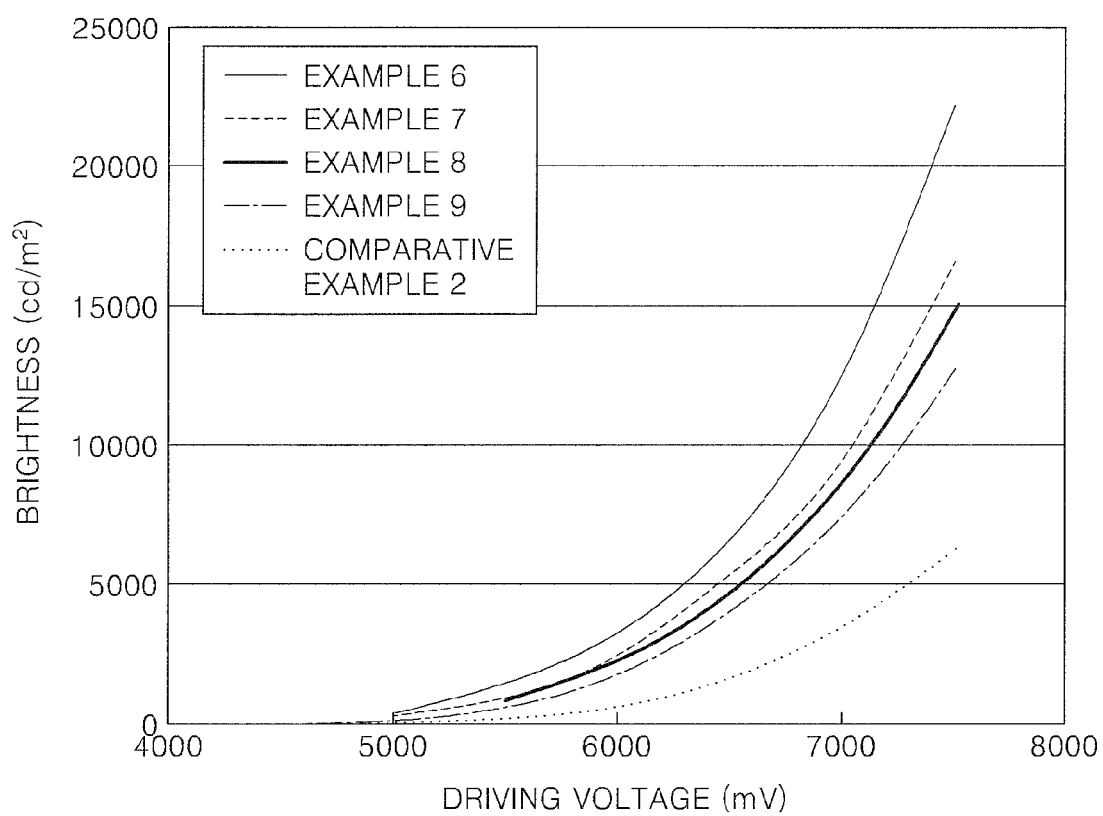
FIG. 3 is a graph comparing the brightness characteristics with respect to driving voltage of the organic light emitting devices prepared according to Examples 6 through 9 to the brightness characteristics with respect to driving voltage of the organic light emitting device prepared according to Comparative Example 2.

Moreover, as can be seen from the results above, when used as hole injection or hole transportation materials of organic light emitting devices, the compounds represented by Formula 1 according to embodiments of the present invention have lower driving voltages compared to the conventional material, 2-TNATA. In particular, based on their superior hole injection and hole transportation characteristics, the compounds represented by Formula 1 according to embodiments of the present invention showed excellent I-V-L properties with 30% or more improved efficiency (See FIG. 3), and can be used to prepare organic light emitting devices with low voltage, high efficiency, high brightness, and long life span.

The compounds represented by Formula 1 according to embodiments of the present invention have excellent electrical properties and charge transporting characteristics, and are therefore useful as materials for hole injection layers, hole transport layers, and emission layers of phosphorescent and fluorescent devices for emitting light of all colors, including red, green, blue, and white. Using these compounds, an organic light-emitting device with high efficiency, low driving voltage, and high brightness can be prepared.

While the present invention has been illustrated and described with reference to certain exemplary embodiments, it is understood by those of ordinary skill in the art that various changes and modifications may be made to the described embodiments without departing from the spirit and scope of the present invention as defined by the following claims.

What is claimed is:

1. A compound comprising a material represented by Formula 1:

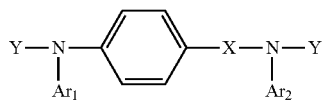

Formula 1 wherein:
X is selected from the group consisting of structures represented by:

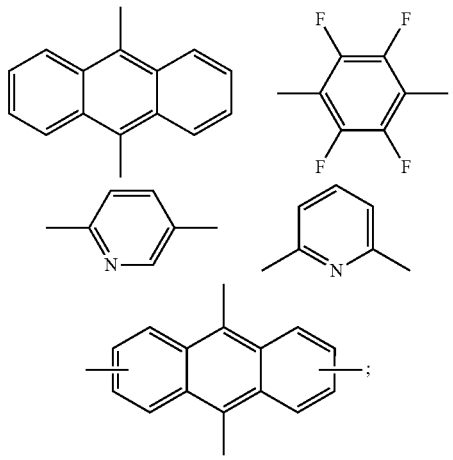

each of $Ar_1$ and $Ar_2$ is independently selected from the group consisting of substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups; and Y is selected from the group consisting of materials represented by Formulae 2 and 3

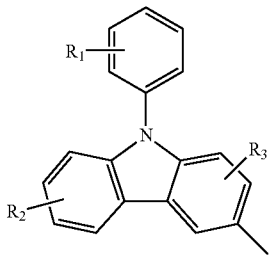

Formula 2

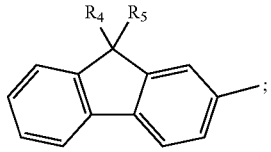

Formula 3 wherein each of $R_1$, $R_2$, $R_3$, $R_4$ and $R_5$ is independently selected from the group consisting of hydrogen, substituted and unsubstituted $C_1$-$C_{10}$ alkyl groups, a substituted or nonsubstituted C6-C20 aryl group, substituted and unsubstituted $C_1$-$C_{10}$ alkoxy groups, fluorine, cyano groups, and amine groups.

2. The compound of claim 1, wherein at least two adjacent R groups selected from the group consisting of $R_1$, $R_2$, $R_3$, $R_4$ and $R_5$ bond with one another to form a saturated or unsaturated carbon ring.

3. The compound of claim 1, wherein the material represented by Formula 1 is a material represented by Formula 5:

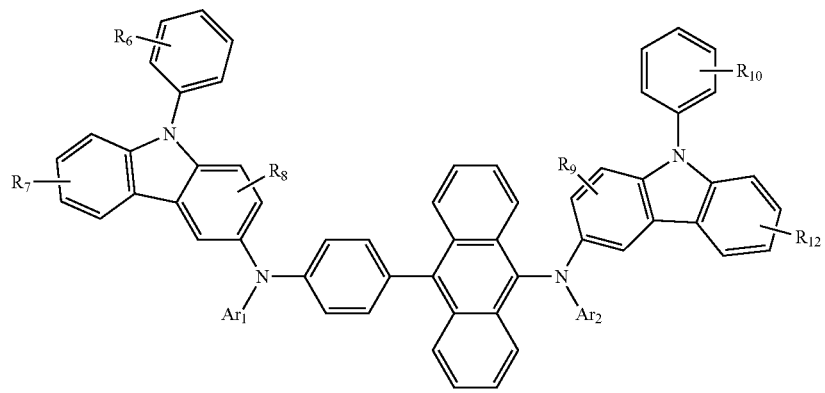

Formula 5 wherein each of $R_6$, $R_7$, $R_8$, $R_9$, $R_{10}$, $R_{11}$ and $R_{12}$ is independently selected from the group consisting of hydrogen, substituted and unsubstituted $C_1$-$C_{10}$ alkyl groups, a substituted or nonsubstituted C6-C20 aryl group, substituted and unsubstituted $C_1$-$C_{10}$ alkoxy groups, fluorine, cyano groups, and amino groups; and each of $Ar_1$ and $Ar_2$ is independently selected from the group consisting of substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups.

4. The compound of claim 3, wherein at least two adjacent R groups selected from the group consisting of $R_6$, $R_7$, $R_8$, $R_9$, $R_{10}$, $R_{11}$ and $R_{12}$ bond with one another to form a saturated or unsaturated carbon ring.

5. A compound comprising a material represented by Formula 8:

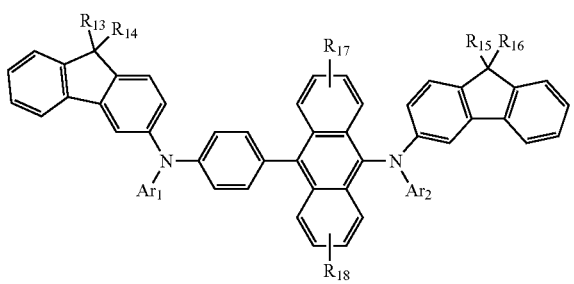

Formula 8 wherein each of $R_{13}$, $R_{14}$, $R_{15}$, $R_{16}$, $R_{17}$ and $R_{18}$ is independently selected from the group consisting of hydrogen, substituted and unsubstituted $C_1$-$C_{10}$ alkyl groups, a substituted or nonsubstituted C6-C20 aryl group, substituted and unsubstituted $C_1$-$C_{10}$ alkoxy groups, fluorine, cyano groups, and amino groups; and each of $Ar_1$ and $Ar_2$ is independently selected from the group consisting of substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups.

6. The compound of claim 5, wherein at least two adjacent R groups selected from the group consisting of $R_{13}$, $R_{14}$, $R_{15}$, $R_{16}$, $R_{17}$ and $R_{18}$ bond with one another to form a saturated or unsaturated carbon ring.

7. The compound of claim 1, wherein each of $Ar_1$ and $Ar_2$ is independently selected from the group consisting of phenyl groups, $C_1$-$C_5$ alkylphenyl groups, $C_1$-$C_5$ alkoxyphenyl groups, cyanophenyl groups, phenoxyphenyl groups, fluorophenyl groups, naphthyl groups, $C_1$-$C_5$ alkylnaphthyl groups, $C_1$-$C_5$ alkoxynaphthyl groups, cyanonaphthyl groups, halonaphthyl groups, fluorenyl groups, carbazolyl groups, $C_1$-$C_5$ alkyl carbazolyl groups, biphenyl groups, $C_1$-$C_5$ alkyl biphenyl groups, $C_1$-$C_5$ alkoxy biphenyl groups and pyridyl groups.

8. The compound of claim 1, wherein each of $Ar_1$ and $Ar_2$ is independently selected from the group consisting of phenyl groups, ethylphenyl groups, ethylbiphenyl groups, o-, m-, p-fluorophenyl groups, dichlorophenyl groups, dicyano groups, trifluorophenyl groups, methoxyphenyl groups, o-, m-, and p-tolyl groups, mesityl groups, phenoxyphenyl groups, (α, α-dimethyl benzene)phenyl groups, (N,N'-dimethyl)aminophenyl groups, (N,N'-diphenyl) aminophenyl groups, pentalenyl groups, naphthyl groups, methylnaphthyl groups, anthracenyl groups, azulenyl groups, heptalenyl groups, acenaphthylenyl groups, fluorenyl groups, anthraquinolyl groups, phenanthryl groups, triphenylene groups, pentaphenyl groups, hexaphenyl groups, and carbazolyl groups.

9. The compound of claim 1, wherein each of $Ar_1$ and $Ar_2$ is independently selected from the group consisting of aryl groups comprising from 1 to 3 rings selected from the group consisting of fluorenyl groups, carbazolyl groups, phenyl groups, naphthyl groups, biphenyl groups, and aromatic rings thereof substituted with one to three groups selected from the group consisting of $C_1$-$C_4$ alkyl groups, $C_1$-$C_5$ alkoxy groups, cyano groups, amino groups, phenoxy groups, phenyl groups, and halogen atoms.

10. The compound of claim 1, wherein the material represented by Formula 1 is selected from the group consisting of Compounds 105 and 213:

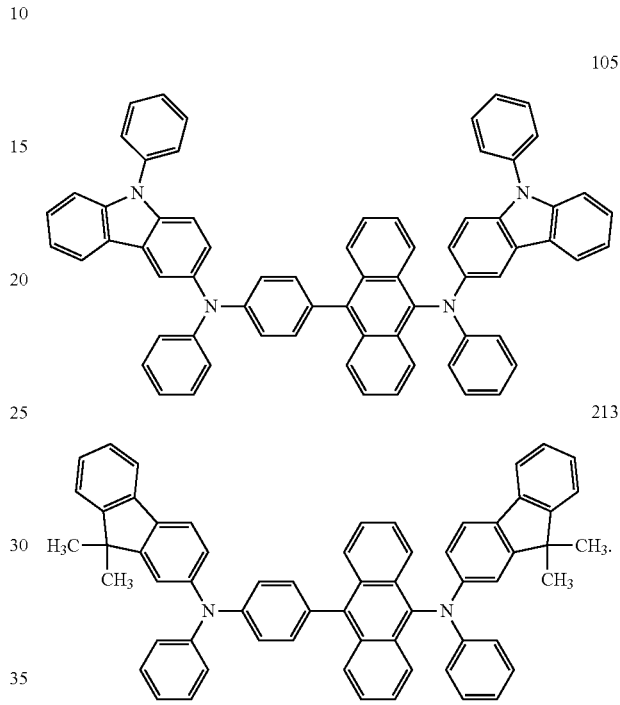

11. An organic light emitting device comprising a first electrode, a second electrode, and an organic film between the first electrode and the second electrode, wherein the organic film comprises the compound of claim 1.

12. The organic light emitting device of claim 11, wherein the organic film comprises a layer selected from the group consisting of hole injection layers and hole transport layers.

13. The organic light emitting device of claim 11, wherein the organic film comprises a single film comprising a hole injection layer and a hole transport layer.

14. The organic light emitting device of claim 11, wherein the organic film comprises an emissive layer.

15. The organic light emitting device of claim 14, wherein the emissive layer comprises the compound of claim 1 as a host, and further comprises a dopant selected from the group consisting of phosphorescent and fluorescent dopants.

16. The organic light emitting device of claim 11, wherein the device comprises a structure selected from the group consisting of first electrode/hole injection layer/emissive layer/second electrode structures, first electrode/hole injection layer/hole transport layer/emissive layer/electron transport layer/second electrode structures, and first electrode/hole injection layer/hole transport layer/emissive layer/electron transport layer/electron injection layer/second electrode structures.

17. The organic light emitting device of claim 16, further comprising at least one of a hole blocking layer and an electron blocking layer.

18. A flat panel display device comprising the organic light emitting device according to claim 11, wherein the first electrode of the organic light emitting device is electrically connected to a source electrode or a drain electrode of a thin film transistor.

19. A compound comprising a material represented by Formula 1:

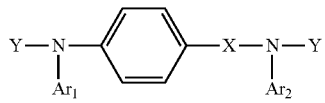

Formula 1 wherein:
X is selected from the group consisting of structures represented by:

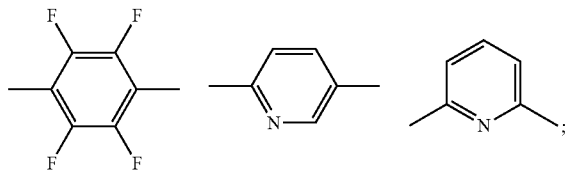

each of Ar₁ and Ar₂ is independently selected from the group consisting of substituted and unsubstituted $C_6$-$C_{20}$ aryl groups, substituted and unsubstituted $C_6$-$C_{20}$ aryloxy groups, substituted and unsubstituted $C_4$-$C_{20}$ heteroaryl groups, and substituted and unsubstituted $C_4$-$C_{20}$ condensed polycyclic groups; and Y is selected from the group consisting of materials represented by Formulae 2 and 3

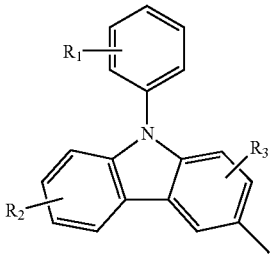

Formula 2

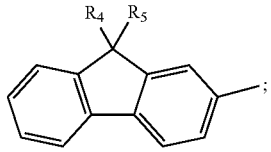

Formula 3 wherein each of $R_1$, $R_2$, $R_3$, $R_4$ and $R_5$ is independently selected from the group consisting of hydrogen, substituted and unsubstituted $C_1$-$C_{10}$ alkyl groups, a substituted or nonsubstituted C6-C20 aryl group, substituted and unsubstituted $C_1$-$C_{10}$ alkoxy groups, fluorine, cyano groups, and amine groups.

* * * * *